US012528845B2

(12) United States Patent
Matsunaga et al.

(10) Patent No.: US 12,528,845 B2
(45) Date of Patent: Jan. 20, 2026

(54) FISH ALLERGY ANTIGEN

(71) Applicant: HOYU CO., LTD., Aichi (JP)

(72) Inventors: Kayoko Matsunaga, Aichi (JP); Akiko Yagami, Aichi (JP); Naoshi Shimojo, Aichi (JP)

(73) Assignee: HOYU CO., LTD., Aichi (JP)

( * ) Notice: Subject to any disclaimer, the term of this patent is extended or adjusted under 35 U.S.C. 154(b) by 139 days.

(21) Appl. No.: 18/491,287

(22) Filed: Oct. 20, 2023

(65) Prior Publication Data

US 2024/0109943 A1 Apr. 4, 2024

Related U.S. Application Data

(62) Division of application No. 16/309,453, filed as application No. PCT/JP2017/017018 on Apr. 28, 2017, now abandoned.

(30) Foreign Application Priority Data

Jun. 16, 2016 (JP) ................................ 2016-119919

(51) Int. Cl.

| | |
|---|---|
| ***C07K 14/46*** | (2006.01) |
| ***A23L 17/00*** | (2016.01) |
| ***A23L 17/30*** | (2016.01) |
| ***A23L 33/00*** | (2016.01) |
| ***A61K 39/00*** | (2006.01) |
| ***A61K 39/35*** | (2006.01) |
| ***A61P 37/08*** | (2006.01) |
| ***C12Q 1/48*** | (2006.01) |
| ***C12Q 1/6888*** | (2018.01) |
| ***G01N 33/53*** | (2006.01) |
| ***G01N 33/68*** | (2006.01) |
| *C07K 14/47* | (2006.01) |
| *C12N 15/09* | (2006.01) |

(52) U.S. Cl.

CPC ........... *C07K 14/461* (2013.01); *A23L 17/00* (2016.08); *A23L 17/30* (2016.08); *A23L 33/40* (2016.08); *A61K 39/00* (2013.01); *A61K 39/35* (2013.01); *A61P 37/08* (2018.01); *C12Q 1/48* (2013.01); *C12Q 1/6888* (2013.01); *G01N 33/53* (2013.01); *G01N 33/6854* (2013.01); *G01N 33/6893* (2013.01); *A23V 2002/00* (2013.01); *C07K 14/47* (2013.01); *C12N 15/09* (2013.01); *G01N 2800/24* (2013.01)

(58) Field of Classification Search

None

See application file for complete search history.

(56) References Cited

U.S. PATENT DOCUMENTS

| | | | |
|---|---|---|---|
| 2006/0121478 | A1 | 6/2006 | North |
| 2011/0071043 | A1 | 3/2011 | Sampson et al. |
| 2019/0256566 | A1 | 8/2019 | Matsunaga et al. |
| 2020/0268877 | A1 | 8/2020 | Matsunaga et al. |
| 2023/0295251 | A1 | 9/2023 | Matsunaga et al. |

FOREIGN PATENT DOCUMENTS

| | | | |
|---|---|---|---|
| CN | 103931936 | A | 7/2014 |
| JP | 2000-125775 | A | 5/2000 |
| JP | 2002-286716 | A | 10/2002 |
| JP | 2005-538710 | A | 12/2005 |
| JP | 2011-033544 | A | 2/2011 |
| JP | 2011-033546 | A | 2/2011 |
| JP | 2011-033547 | A | 2/2011 |
| JP | 2011-033548 | A | 2/2011 |
| JP | 5894695 | B1 | 3/2016 |
| WO | 2002/50269 | A1 | 6/2002 |
| WO | 2009/078806 | A2 | 6/2009 |
| WO | 2015/048340 | A2 | 4/2015 |
| WO | 2015/048342 | A2 | 4/2015 |
| WO | 2016/190376 | A1 | 12/2016 |

OTHER PUBLICATIONS

U.S. Appl. No. 16/309,453, filed Dec. 13, 2018, 2019-0256566, Published.

U.S. Appl. No. 16/608,361, filed Oct. 25, 2019, 2020-0268877, Abandoned.

U.S. Appl. No. 18/147,789, filed Dec. 29, 2022, 2023-0295251, Published.

Abaza et al., Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992; 11(5):433-44.

Agrisera, Product No. AS05 062, HSC70 / salmon heat shock cognate protein 70. www.agrisera.com, 1 page, downloaded Jun. 16, 2022.

An et al., Alpha-actinin is a new type of house dust mite allergen. PLoS One. Dec. 6, 2013;8(12):e81377, 9 pages.

Blumenthal et al., Definition of an Allergen (Immunobiology). Allergens and Allergen Immunotherapy, Third Edition, Revised and Expanded. Marcel Dekker, Inc., New York. Richard F. Lockey (Ed.). Chapter 2, pp. 37-50, (2004).

(Continued)

*Primary Examiner* — Nora M Rooney

(74) *Attorney, Agent, or Firm* — McCarter & English, LLP; Yu Lu; Thao Nguyen

(57) ABSTRACT

The present invention provides novel antigens of an allergy to fish, methods and kits for diagnosing an allergy to fish, a pharmaceutical composition comprising the antigen, fish or fish eggs in which the antigen is eliminated, a processed product of the fish or the fish eggs or fish which lay the fish eggs or have hatched from the eggs, and a tester for determining the presence or absence of a fish antigen in an object of interest.

3 Claims, 5 Drawing Sheets

Specification includes a Sequence Listing.

(56) References Cited

OTHER PUBLICATIONS

Campbell, General properties and applications of monoclonal antibodies. Monoclonal Antibody Technology. Elsevier Science Publishers B.V., Amsterdam. Chapter 1, pp. 1-32, (1985).
Colman et al., Effects of amino acid sequence changes on antibody-antigen interactions. Res Immunol. Jan. 1994; 145(1):33-6.
Elsayed et al., Characterization of a major allergen (cod). Observations on effect of denaturation on the allergenic activity. J Allergy. May 1971;47(5):283-91.
Gamez et al., New shrimp IgE-binding proteins involved in mite-seafood cross-reactivity. Mol Nutr Food Res. Sep. 2014;58(9):1915-25.
Gonzalez-Mancebo et al., Identification of a novel protein allergen in Mediterranean silverside fish species. Ann Allergy Asthma Immunol. Jul. 2014; 113(1):114-5.
Harlow et al., Antibodies, A Laboratory Manual. Cold Spring Harbor Laboratory. Chapters 5-6, pp. 53-157, (1988).
Hart et al., Vertebrate isoforms of actin capping protein beta have distinct functions In vivo. J Cell Biol. Dec. 1, 19993;147(6):1287-98.
Homaei et al., Enzyme immobilization: an update. J Chem Biol. Aug. 29, 2013;6(4):185-205.
Kobayashi et al., Study of the cross-reactivity of fish allergens based on a questionnaire and blood testing. Allergol Int. Jul. 2016;65(3):272-9.
Kobayashi et al., Study of the cross-reactivity of fish allergens based on a questionnaire and blood testing. Allergol Int. Feb. 2016, pp. 1-8, prepublication version.
Kuehn et al., Identification of enolases and aldolases as important fish allergens in cod, salmon and tuna: component resolved diagnosis using parvalbumin and the new allergens. Clin Exp Allergy. Jul. 2013;43(7):811-22.
Lederman et al., A single amino acid substitution in a common African allele of the CD4 molecule ablates binding of the monoclonal antibody, OKT4. Mol Immunol. Nov. 1991;28(11):1171-81.
Lee et al., Proteomic profiling of lymphedema development in mouse model. Cell Biochem Funct. Jul. 2016;34 (5):317-25.
Lee et al., Proteomic profiling of lymphedema development in mouse model. Cell Biochem Funct. Jul. 2016;34 (5):317-25. Published online May 5, 2016, DOI: 10.1002/cbf.3192.
Matsuo et al., Identification of the IgE-binding epitope in omega-5 gliadin, a major allergen in wheat-dependent exercise-induced anaphylaxis. J Biol Chem. Mar. 26, 2004;279(13):12135-40.
Mermelstein, Allergen Detectives. Food Technology. Jan. 2014;68(1):68-71.
Mills et al., Differential expression of the actin-binding proteins, alpha-actinin-2 and -3, in different species: implications for the evolution of functional redundancy. Hum Mol Genet. Jun. 1, 20015;10(13):1335-46.
Nakamura et al., Antigen analysis of shrimp allergy using clinical research system for allergic disease "MINERVA." The Journal of Allergy and Clinical Immunology. Feb. 1, 2020;145(2):Abstract 721, 1 page. DOI: https://doi.org/10.1016/jaci.2019.12.177.
Nilsson et al., Intrasplenic immunization with minute amounts of antigen. Immunol Today. Jan. 1990;11(1):10-2.
Perez-Gordo et al., Epitope mapping of Atlantic salmon major allergen by peptide microarray immunoassay. Int Arch Allergy Immunol. 2012; 157(1):31-40.
Polymeropoulo et al., Growth hormone transgenesis and polyploidy increase metabolic rate, alter the cardiorespiratory response and influence HSP expression in response to acute hypoxia in Atlantic salmon (*Salmo salar*) yolk-sac alevins. The Journal of Experimental Biology. 2014;217:2268-2276.
Sakaguchi et al., IgE antibody to fish gelatin (type I collagen) in patients with fish allergy. J Allergy Clin Immunol. Sep. 2000;106(3):579-84.
Shimojo et al., Occupational fish allergy caused by percutaneous sensitization with a-actinin-3. Contact Dermatitis. May 2017;76(5):322-323.
UniProt Accession No. B5RIA0, Full=Putative uncharacterized protein. 1 page, Nov. 4, 2008.
UniProtKB Accession No. B5X3U6, Heat shock cognate 70 kDa protein. 5 pages, (2018).
UniProtKB Accession No. Q8AW95, 1 page, Mar. 1, 2003.
UniProtKB B5RI29, EEF1A2 binding protein-like. Retrieved online at: https://www.uniprot.org/uniprot/B5RI29. 6 pages, Aug. 12, 2020.
Van Der Ventel et al., Differential responses to natural and recombinant allergens in a murine model of fish allergy. Mol Immunol. Jan. 2011;48(4):637-46.
Van Do et al., Allergy to fish parvalbumins: studies on the cross-reactivity of allergens from 9 commonly consumed fish. J Allergy Clin Immunol. Dec. 2005; 116(6):1314-20.
Virel et al., Molecular evolution and structure of alpha-actinin. Mol Biol Evol. Jun. 2004;21(6):1024-31.
WHO/IUIS Allergen Nomenclature Sub-Committee, Allergen Nomenclature. 3 pages, Jun. 9, 2016.
Xing et al., Effects of atrazine and chlorpyrifos on the mRNA levels of HSP70 and HSC70 in the liver, brain, kidney and gill of common carp (*Cyprinus carpio* L.). Chemosphere. Jan. 2013;90(3):910-6.
Yasuda et al., Allergic study of food urticaria. (1). Allergic food urticaria due to fish. Arerugi. Dec. 1984;33 (12):1016-24.
International Search Report for Application No. PCT/JP2017/017018, dated Aug. 1, 2017, 4 pages.
International Search Report for Application No. PCT/JP2017/045832, dated Mar. 27, 2018, 4 pages.
Supplementary Partial European Search Report for Application No. 17813033.2, dated Oct. 15, 2019, 12 pages.
Supplementary Partial European Search Report for Application No. 17907256.6, dated Feb. 26, 2021, 14 pages.

| Number | Protein name |
|---|---|
| 1 | Alpha-actinin-3 |
| 2 | EEF1A2 binding protein-like |
| 3 | Alpha-1,4-glucan phosphorylase |
| 4 | Elongation factor 2 |
| 5 | Heat shock cognate 70 kDa protein |
| 6 | Serotransferrin |
| 7 | Myosin binding protein H-like |
| 8 | Desmin (Fragment) |
| 9 | Capping protein (Actin filament) muscle Z-line beta |

Fig. 1B

Immunoblot stained with serum of Fish-allergic patient 2

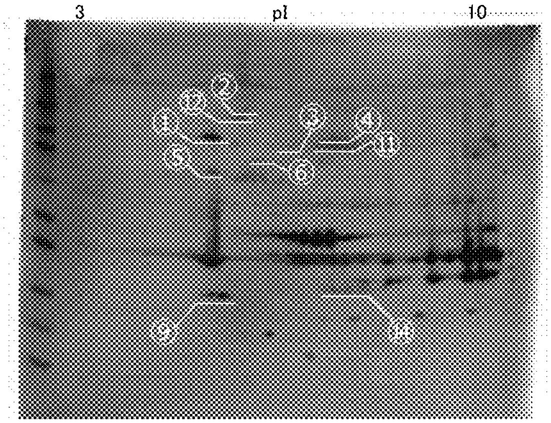

Immunoblot stained with serum of Fish-allergic patient 3

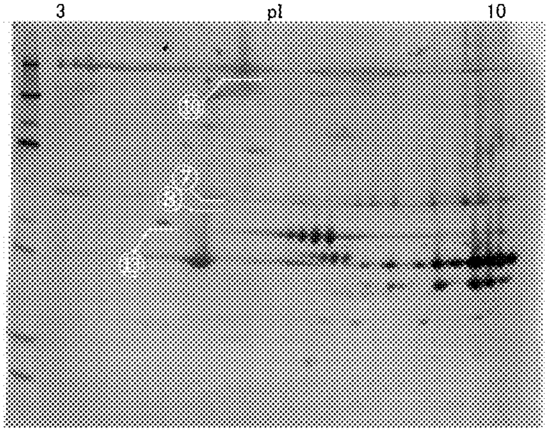

| Number | Protein name |
|---|---|
| 1 | Alpha-actinin-3 |
| 2 | EEF1A2 binding protein-like |
| 3 | Alpha-1,4-glucan phosphorylase |
| 4 | Elongation factor 2 |
| 5 | Heat shock cognate 70 kDa protein |
| 6 | Serotransferrin |
| 7 | Myosin binding protein H-like |
| 8 | Desmin (Fragment) |
| 9 | Capping protein (Actin filament) muscle Z-line beta |
| 10 | Myosin heavy chain, fast skeletal muscle-like |
| 11 | Glycogen phosphorylase, muscle form-like |
| 12 | Myosin-binding protein C, fast-type-like |
| 13 | ATP synthase subunit beta, mitochondrial |
| 14 | L-lactate dehydrogenase A chain-like |

Result of immunoblot of 10 fish species stained with serum of Non-fish-allergic subject Result of immunoblot of 6 fish species stained with serum of Fish-allergic patient 4

SEQUENCE LISTING

```
Sequence total quantity: 149
SEQ ID NO: 1          moltype = DNA  length = 2685
FEATURE               Location/Qualifiers
misc_feature          1..2685
                      note = PREDICTED: alpha-actinin-3
source                1..2685
                      mol_type = other DNA
                      organism = synthetic construct
SEQUENCE: 1
atgacggcaa tcgaaactca ggtgcaatat ggctcctaca tgacttcgga gcaagtctac  60
atgacccaag aggatgattg ggacagggac cttctgttgg accctgcctg ggagaaacag  120
cagcgcaaga ccttcaccgc ctggtgcaac tctcacctgc gtaaagcggg cacacagatt  180
gagaacattg aggaggactt caggaatggg ctcaagctca tgttgctgtt agaggtcatc  240
tcaggtgaaa ggcttcccaa accagacaaa ggcaaaatgc gtttccacaa aatcgccaac  300
gtgaacaagg ccctggattt catctgcagc aagggagtca agctggtgtc catcggtgcc  360
gaggagattg tggatggtaa tgtgaagatg accctgggga tgatctggac catcattctg  420
cgtttcgcca tccaggacat ctctgtagag gagacctctg ctaaggaggg tctgttgctg  480
tggtgccaga ggaagactgc cccctacagg aatgtcaatg tgcagaactt ccacatcagt  540
tggaaggatg gcctggcact gtgtgccctc atccacagac acagacctga cctcattgac  600
tactccaaac tgcgcaagga tgaccccatg ggcaatctca acactgcctt tgaggtggca  660
gagaagtacc tggacatccc caagatgttg gatgcagaag atattgtgaa caccccgaag  720
cccgacgaga aagccatcat gacctatgtg tcctgcttct atcatgcctt cgctggagcc  780
gagcaggccg agacagctgc caataggatc tgcaaggtgt tggctgtcaa ccaggagaac  840
gagaagctca tggaggagta tgagaagctg gccagtgagc tgctggagtg gatccgtcgc  900
accatcccct ggctggagaa ccgcgtggct gagcagacca tgcgcgccat gcagcagaag  960
```

```
ctggaggact tccgtgacta ccgtcgcgtc cacaagcctc ccaaggtgca ggagaagtgt  1020
cagctggaga ttaacttcaa caccctgcag accaagctga ggctgagcaa caggcccgcc  1080
ttcatgccct ccgagggcaa gatggtgtcg gacattgcca atgcctggaa gggtctggag  1140
caggtagaga agggctatga ggagtggctg ctcactgaga tcagacgcct ggagaggctg  1200
gaccacctgg ctgagaagtt caagcagaag tcttccctgc atgagtcctg gacctcaggt  1260
aaggtggagc tgctgtccat gaaggactat gagtctgcct cactgatgga gatccgtgcc  1320
ctgatgagga agcacgaggc gtttgagagc gacctggctg cccaccagga cagagtggag  1380
cagattgctg ccatcgccca ggagctcaat gagctggact atcatgatgc cgtcaccatc  1440
aacgcccgct gccagggtat ttgtgaccag tgggacaacc tgggcacctt gacccagaag  1500
aggagagact cactggagcg tgtggagaag ctgtgggaga ccatcgacca gctgtacctg  1560
gagtttgcca agagagcagc cccctttcaac aactggatgg acggagccat ggaggactta  1620
caggacatgt tcattgtgca cagcattgag gagatccaga gtctgatcac agcccatgac  1680
cagttcaagg ccaccctgcc agaggcagat aaggagcgcg ttgcaaccat gggaatccag  1740
aatgagatcg tgaagatcgc tcagacctac ggcatcaagc tgtcaggagt caacccctac  1800
accaaccttt ccccccagga catcaccgac aaatgggatg ctgtgaaaca cctggtgccc  1860
ctcagggatc agatgctgca ggaggaggtg gccaggcagc agtccaacga gaggctgagg  1920
cgccagttcg ctgcccaggc caacatcatc ggaccctgga tccagaccaa gatggaggag  1980
atcagccatg tgtctgtgga catcgccggc tccctggagg aacagatgag caacctgaag  2040
cagtacgagc agaacatcat caactacaag tgcaacatcg acaagctgga gggagaccac  2100
caactcagcc aggagtccct catctttgac aacaagcaca ccaactacac catggagcat  2160
gtgcgtgtgg gctgggagca gctcctcacc accatcgccc gcaccatcaa cgaggtggag  2220
aaccagatcc tgacccgaga tgccaagggc atcagccagg agcagctcaa cgagttcaga  2280
gcctccttca accactttga caggaagaga aatggtatga tggacccaga tgacttccgt  2340
gcctgtctca tctccatggg ctacgatctg ggtgaggtgg agtttgcccg catcatgacg  2400
ctggtggatt ccaacaacac aggtgtggtg accttccagg ccttcatcga cttcatgacc  2460
cgcgagacgg ccgagacaga caccgccgat caggtcatgg cctcattcaa gatcctggcc  2520
tctgacaaga catacatcac agtggaagaa ctgcgcaggg agctgccccc agagcaggcc  2580
gactactgca tcagccgcat gaccagttac atcggcagcg gcgcaccccc aggcgccctg  2640
gactacatct ccttctccag tgccctgtac ggagagagcg actta                   2685
```

```
SEQ ID NO: 2           moltype = AA  length = 895
FEATURE                Location/Qualifiers
REGION                 1..895
                       note = PREDICTED: alpha-actinin-3
source                 1..895
                       mol_type = protein
                       organism = synthetic construct
SEQUENCE: 2
MTAIETQVQY GSYMTSEQVY MTQEDDWDRD LLLDPAWEKQ QRKTFTAWCN SHLRKAGTQI  60
ENIEEDFRNG LKLMLLLEVI SGERLPKPDK GKMRFHKIAN VNKALDFICS KGVKLVSIGA  120
EEIVDGNVKM TLGMIWTIIL RFAIQDISVE ETSAKEGLLL WCQRKTAPYR NVNVQNFHIS  180
WKDGLALCAL IHRHRPDLID YSKLRKDDPM GNLNTAFEVA EKYLDIPKML DAEDIVNTPK  240
PDEKAIMTYV SCFYHAFAGA EQAETAANRI CKVLAVNQEN EKLMEEYEKL ASELLEWIRR  300
TIPWLENRVA EQTMRAMQQK LEDFRDYRRV HKPPKVQEKC QLEINFNTLQ TKLRLSNRPA  360
FMPSEGKMVS DIANAWKGLE QVEKGYEEWL LTEIRRLERL DHLAEKFKQK SSLHESWTSG  420
KVELLSMKDY ESASLMEIRA LMRKHEAFES DLAAHQDRVE QIAAIAQELN ELDYHDAVTI  480
NARCQGICDQ WDNLGTLTQK RRDSLERVEK LWETIDQLYL EFAKRAAPFN NWMDGAMEDL  540
QDMFIVHSIE EIQSLITAHD QFKATLPEAD KERVATMGIQ NEIVKIAQTY GIKLSGVNPY  600
TNLSPQDITD KWDAVKHLVP LRDQMLQEEV ARQQSNERLR RQFAAQANII GPWIQTKMEE  660
ISHVSVDIAG SLEEQMSNLK QYEQNIINYK CNIDKLEGDH QLSQESLIFD NKHTNYTMEH  720
VRVGWEQLLT TIARTINEVE NQILTRDAKG ISQEQLNEFR ASFNHFDRKR NGMMDPDDFR  780
ACLISMGYDL GEVEFARIMT LVDSNNTGVV TFQAFIDFMT RETAETDTAD QVMASFKILA  840
SDKTYITVEE LRRELPPEQA DYCISRMTSY IGSGAPPGAL DYISFSSALY GESDL       895
```

```
SEQ ID NO: 3           moltype = AA  length = 14
FEATURE                Location/Qualifiers
REGION                 1..14
                       note = PREDICTED: alpha-actinin-3 fragment
source                 1..14
                       mol_type = protein
                       organism = synthetic construct
SEQUENCE: 3
ERVATMGIQN EIVK                                                     14
```

```
SEQ ID NO: 4           moltype = DNA  length = 3591
FEATURE                Location/Qualifiers
misc_feature           1..3591
                       note = EEF1A2 binding protein-like
source                 1..3591
                       mol_type = other DNA
                       organism = synthetic construct
SEQUENCE: 4
atgtggaaaa agaaatcaaa gctcacggac cagacggcca ctggccaagt tgggatcaag  60
aagagatcaa aagtccctgg agttatgatc acgcagtatg tggagaaaat accagatggg  120
aaaagccacc ctgacttcac ccgcaagcct atcgcgttga ccattcagga gggtaaattc  180
gccttcttca aagccctggt tattggagat ccagaaccaa ccgtgacatg gggcagaaat  240
aatggagatg tgtcagatac atcaaaatat gtgacaaaat atgaccctgc tacacgtgag  300
cacttatttg agatggccaa tgtaaaacca gaacaagcag acacctacaa atgctttgca  360
gctaatgagt ttggaagagc agtggtcaca gtggtcctca atgttattga agttgggttc  420
```

```
aagaaagcac aagcggactc acaggtgcaa ccagaggcag ctgttgcaga ttttaaatct  480
gtattgaaga gaaaaagtaa aattcagccc aaaatggaaa agaaagaaga tggagaaata  540
gatccaagat tttgggaact cttgataagt gctgacaaga aagactatga gagcctcatg  600
ttggagtttg gagtcactga cttccgcttt atgctgaaga cactgaatga gattaagaag  660
gaaagagagg aagagcaagc acagttcatt gaaaacctag ctaacctgaa acctattgaa  720
gttggacccg atggctgtgc aaccttttca atagacatgg atctcattga acaaagcagc  780
aggatcttcc tctacaagga tggagtgatg attccataca gcaaggagtt gggagataca  840
atcaaacaca gcctaaagat agtgggccga aagtatcagt tcagcataag ggatctgttt  900
cctgatgatg ctgggctcta ccaggtggat gttgaggacg taaatgtatt ctccaccgat  960
tttaagattc ccatggtgga cttcctggtc aagattcagg agtgtaaggc catggagaga  1020
gaggatgctg tgtttgagtg tgtcctgtca cagcccttcg gcaagatcat gtgggttggc  1080
aagaacttac cattggaggc aggggataaa tatgatattg aggtttcaga agacaagctc  1140
atccacagac taatcattaa agacgttgct atggtggaca aaggcatcta tgccgctgtg  1200
gcaggaatca aatcttgcaa tgcctttctt gtggttgaag ccgacaaggg tgaacccggc  1260
aaaaagaaac aacgtaaaac cacaagggca ggaggagctg gagttgacct gacggcgatt  1320
gcccaagagc aggcagttaa aaacacggca gacagagagg tgctgaagga gaaggtgaaa  1380
gcaatcaatg acgagagagc ggctaatgcc actgcagcac ctgagacttc agctgaagct  1440
aaagctaaag ttaaggtggt agaggcttcc caaacaggag ctccaaaaca gggaccggca  1500
gttaaagggt ctgaccataa atccgtggat aatgagggat acagcattaa gagtggactc  1560
tcagatgtct ttgctctccg tggcaagaaa ggtgaactgg tttgtgagat gagccatgaa  1620
gttgatgggg cctggttcaa ggatggagag aagttatcca ccacagatgg aatagccata  1680
gtgaaagatg gaacgagaca cacgatgacc attcatagca gtagtgaaga cgacactgga  1740
gtctatcaca ttgaagcggg gggatttaaa tcagaggcaa aagtcactgt gggagaatta  1800
cctgccattg atgctgatga cctccacaag ttttctaagc ctgtgacaat aaaagtgggc  1860
cagaatgcat cctggaagat gccttataca ccacaggaca acttggaggt gaaatggttt  1920
aaggatggca aagagttgaa ggatggtggt ggggtgaagt tggtgaagga ggtcaagcac  1980
agccggctgc tgctccggga gtgtctgcgt tctgacgctg gggagatcaa gattcaactc  2040
aaaaaccccct ttggcactat agaggccaca tctcgactga ttgtccttga caagcccggc  2100
ccaccagaag gcccggtgga aatcttggag accacctcca ctgtgattga gctgcagtgg  2160
ggcgctccta aggacgacgg tggctccccg gtgactaact acatcattga gcgccagcag  2220
ctgggacaga ccgtgtggaa gaagatgggt gatgtcgcag ctgacaaaac cacctacagg  2280
gacaggaatg tggtccatgg gaaactgtac atctacaata tctacgcagt gaacccagag  2340
gggaccagtg atgcactgca gactgaggaa acaatggctg gcgtattgat atttgctggc  2400
cgacctggag caccaaaagt ggtcagcgca tcaaagacct gcatcaacct gaaatgggag  2460
cccccagaag atgacggagg aattaagatt gatggctatc aactggaaaa acgcaaaaag  2520
gacacagctc agtggattgc tttgaaccca gtaactgagc ctattgaagt gctggagtac  2580
gcagtgaagg atgttgttga gggggcggag tatgagttca gggtatcggc catcaacgtt  2640
tctggggcgg gagagttcag tctcccctct gtgatggtga ctgcaaagaa tcccaacatg  2700
aggcctacat tcaaagatcc agaggacttc atggtgatca gggcgggaaa ctctgtgaga  2760
atcaaagttc tctatgaggc tgagcctcca ccggagatca cttggatgaa ggacaatgag  2820
cctgtatcca gttttataca gatcatcaac acagagggct gttcccagct tgtgatcccc  2880
tcaacaaaac gctctgattc aggaaattac accattgtgg ctaagaataa agttggagag  2940
gccagctttg acattgaggt cctagtcaca gatgagccaa agcctcctgg tgcagtggag  3000
ctggagcaga ttgtccatgg caaagttatt gtgtcctggg aggcctctcc agaccaggag  3060
ctggacaaca ggctgtatta catggtggcc gagcacgact ccagcacacg catgtggcac  3120
actgtggcag accgcatctt tgacaattca tacacagcca ataacatcat gcctggaagg  3180
gagtaccact tcaaaatcta tgccaagaac gacatgggca tgtcagaccc ctccatgtca  3240
cccacctggg gcatcaacag caacagaatt cctataaaca caaacacgcc agtggaagtc  3300
agctttgaga aaccaccatc tgtcctggtc cctctgaaga tgcactcgcc accaaaagga  3360
ttccagatgt acatgacctg cgccatccgg ggatgcccca cacccagcgt cacgtggcac  3420
ctgaacaacg tctgcatcaa tggtgacagc aactactaca tcaccaactc gtatggcgtg  3480
tgctccatgt acatccttag ggtcaggccc aaggacgccg gagaatacaa agttgtcgca  3540
gttaactcct tcggcaaggc agaatgctcc actaaacttg ttgttaaaga c           3591

SEQ ID NO: 5            moltype = AA  length = 1197
FEATURE                 Location/Qualifiers
REGION                  1..1197
                        note = EEF1A2 binding protein-like
source                  1..1197
                        mol_type = protein
                        organism = synthetic construct
SEQUENCE: 5
MWKKKSKLTD QTATGQVGIK KRSKVPGVMI TQYVEKIPDG KSHPDFTRKP IALTIQEGKF  60
AFFKALVIGD PEPTVTWGRN NGDVSDTSKY VTKYDPATRE HLFEMANVKP EQADTYKCFA  120
ANEFGRAVVT VVLNVIEVGF KKAQADSQVQ PEAAVADFKS VLKRKSKIQP KMEKKEDGEI  180
DPRFWELLIS ADKKDYESLM LEFGVTDFRF MLKTLNEIKK EREEEQAQFI ENLANLKPIE  240
VGPDGCATFS IDMDLIEQSS RIFLYKDGVM IPYSKELGDT IKHSLKIVGR KYQFSIRDLF  300
PDDAGLYQVD VEDVNVFSTD FKIPMVDFLV KIQECKAMER EDAVFECVLS QPFGKIMWVG  360
KNLPLEAGDK YDIEVSEDKL IHRLIIKDVA MVDKGIYAAV AGIKSCNAFL VVEADKGEPG  420
KKKQRKTTRA GGAGVDLTAI AQEQAVKNTA DREVLKEKVK AINDERAANA TAAPETSAEA  480
KAKVKVVEAS QTGAPKQGPA VKGSDHKSVD NEGYSIKSGL SDVFALRGKK GELVCEMSHE  540
VDGAWFKDGE KLSTTDGIAI VKDGTRHTMT IHSSSEDDTG VYHIEAGGFK SEAKVTVGEL  600
PAIDADDLHK FSKPVTIKVG QNASWKMPYT PQDNLEVKWF KDGKELKDGG GVKLVKEVKH  660
SRLLLRECLR SDAGEIKIQL KNPFGTIEAT SRLIVLDKPG PPEGPVEILE TTSTVIELQW  720
GAPKDDGGSP VTNYIIERQQ LGQTVWKKMG DVAADKTTYR DRNVVHGKLY IYNIYAVNPE  780
GTSDALQTEE TMAGVLIFAG RPGAPKVVSA SKTCINLKWE PPEDDGGIKI DGYQLEKRKK  840
DTAQWIALNP VTEPIEVLEY AVKDVVEGAE YEFRVSAINV SGAGEFSLPS VMVTAKNPNM  900
RPTFKDPEDF MVIRAGNSVR IKVLYEAEPP PEITWMKDNE PVSSFIQIIN TEGCSQLVIP  960
STKRSDSGNY TIVAKNKVGE ASFDIEVLVT DEPKPPGAVE LEQIVHGKVI VSWEASPDQE  1020
```

```
LDNRLYYMVA EHDSSTRMWH TVADRIFDNS YTANNIMPGR EYHFKIYAKN DMGMSDPSMS  1080
PTWGINSNRI PINTNTPVEV SFEKPPSVLV PLKMHSPPKG FQMYMTCAIR GCPTPSVTWH  1140
LNNVCINGDS NYYITNSYGV CSMYILRVRP KDAGEYKVVA VNSFGKAECS TKLVVKD     1197

SEQ ID NO: 6           moltype = AA  length = 17
FEATURE                Location/Qualifiers
REGION                 1..17
                       note = EEF1A2 binding protein-like fragment
source                 1..17
                       mol_type = protein
                       organism = synthetic construct
SEQUENCE: 6
AQADSQVQPE AAVADFK                                                 17

SEQ ID NO: 7           moltype = AA  length = 10
FEATURE                Location/Qualifiers
REGION                 1..10
                       note = EEF1A2 binding protein-like fragment
source                 1..10
                       mol_type = protein
                       organism = synthetic construct
SEQUENCE: 7
GIYAAVAGIK                                                         10

SEQ ID NO: 8           moltype = AA  length = 21
FEATURE                Location/Qualifiers
REGION                 1..21
                       note = EEF1A2 binding protein-like fragment
source                 1..21
                       mol_type = protein
                       organism = synthetic construct
SEQUENCE: 8
TTRAGGAGVD LTAIAQEQAV K                                            21

SEQ ID NO: 9           moltype = DNA  length = 2532
FEATURE                Location/Qualifiers
misc_feature           1..2532
                       note = Alpha-1,4 glucan phosphorylase
source                 1..2532
                       mol_type = other DNA
                       organism = synthetic construct
SEQUENCE: 9
atgtcaaaac cgttgtcaga tcacgataga aagaagcaga tctccgtgag aggtcttgct  60
ggtgtggaaa atgtggcaga actgaaggtc gctttcaaca ggcatctcca ttttacgctg  120
gtcaaggaca gaaatgtggc atccaaacgg gattactact ttgctctcgc caacaccgtg  180
cgtgaccact tggtgggcag gtggatcaga acccagcaat actactatga gaaagatccc  240
aaacgtgtgt actacatctc cctggagttc tacatgggtc gcaccctgca gaacaccatg  300
gtgaacctgg cgctggaaaa cgcctgtgat gaggccatat accagctggg tctggacatg  360
gaggagctgg aggacatgga ggaggacgca ggcctgggaa acggtggtct tggacgtctt  420
gccgcctgct tcctggactc tatggcttct ctgggtctgg ctgcgtatgg ctacggtatc  480
cgctatgagt ttggcatctt taaccagaag atcgtcaatg gatggcaggt tgaggaggct  540
gatgactggc tgcgttacgg caacccctgg gagaaggccc gacccgagta catgcgcccc  600
gtcaagttct atggcagaac cgagcacacc ccagagggtg tgaaatgggt tgacactcag  660
gtagtgttgg ctctgccata tgacacccct atccccgggt acagaaacaa cattgtcaac  720
accatgagac tgtggtctgc aaaggcccca tgcgacttca acctgaaaga cttcaacgtt  780
ggtgggtaca ttcaggctgt gttggacaga aacctatgcg agaacatttc ccgtgtgctg  840
taccccaatg ataacttctt tgagggcaag gagctgcgtc tgaagcagga gtactttgtg  900
gtggccgcca cccttcagga catcgtccgt cgtttcaagg cctctaagtt tggctccaga  960
gagatcgtcc gcacagactt cgcccagctg cccaacaaag ttgccatcca gctgaatgac  1020
actcaccctg ccatggccat tcctgagctg atgagggtac tggttgatga ggagaagctg  1080
gagtgggaca aggcctggga cgtgtgtgtc cgtacctgtg cctacacaaa ccacaccgtg  1140
ctgcctgagg ccctggagcg ctggcccatt gacctgttcc atcacctgct gccccgtcac  1200
ctggagatta tctacgagat caaccgtcgc ttcctgcagt acgtcgcctc gaagttccct  1260
ggcgacaacg accgtctgcg ccgcatgtcc ctgattgagg agggagaatg caagaaagtc  1320
aacatggctc atatgtgtat cgttggatcc catgctgtca acggcgtggc ccgcatccac  1380
tcggagatcc tcgtcgccac tctgttcaag gacttttatg agttggaccc acacaagttc  1440
cagaacaaga ccaatggcat caccccccgt cgctggctgg ttatgtgcaa ccccggcttg  1500
gctgaggtca tcgcagagag aattggagag gagtttgtcc gtgaccttga ccagctgaag  1560
aaactgttga agttcattga tgatgatgct ttcatccgtg acatagccaa agtcaagcag  1620
gagaacaagc tgaagttcgc tgtgcacctg gaagaacact acaaagtaaa gatcaacccc  1680
cagtccatgt ttgacttcca agtcaaaaga atccacgagt acaagagaca gctgctcaac  1740
tgtctgcaca tgatcaccta ctacaaccgt atcaagaagg agccaaacaa gcactggacc  1800
ccaagaacca tcatggtcgg aggaaaggct gccccaggct accacacagc caagatgatc  1860
attcgtctca tcaccgctat cggtgaggtt gtcaaccacg accccgtgat cggcgaccgc  1920
ctcaaagtca tcttcttgga gaactacaga gtcaccctgg ctgagaaagc catcccctct  1980
gctgacctgt ctgagcagat ctctacagct ggcactgagg cctctggcac tggcaacatg  2040
aagttcatgc tgaatggcgc tctgaccatc ggcaccatgg acggagccaa cgtggagatg  2100
gccgaggagg ccggagagaa gaacctcttc atcttcggca tgagagtgga ggaagtggac  2160
gcaatggacg ccggcaaagg ataccacgcc tctgagtact acaaccgtat tcccgagctg  2220
```

```
aaacaggcca tggaccagat ctctggtggc ttcttcagcc ataagcagcc agacctcttc  2280
aaggaacttg tggacctgct gatgcaccac gacaggttca aggtgtttgc tgactacgaa  2340
gcctacatca aaagtcagga taaggtcaac gaactgtaca agaaacccaa ggaatggacc  2400
aagatggtga tccataacat tgcaggctgt ggtaaattct ccagcgaccg caccatttcc  2460
cagtacgccc gggagatctg gggcatggag cccagcctgg agaagatccc tgcccccgat  2520
gagcaactca aa                                                     2532

SEQ ID NO: 10          moltype = AA  length = 844
FEATURE                Location/Qualifiers
REGION                 1..844
                       note = Alpha-1,4 glucan phosphorylase
source                 1..844
                       mol_type = protein
                       organism = synthetic construct
SEQUENCE: 10
MSKPLSDHDR KKQISVRGLA GVENVAELKV AFNRHLHFTL VKDRNVASKR DYYFALANTV  60
RDHLVGRWIR TQQYYYEKDP KRVYYISLEF YMGRTLQNTM VNLALENACD EAIYQLGLDM  120
EELEDMEEDA GLGNGGLGRL AACFLDSMAS LGLAAYGYGI RYEFGIFNQK IVNGWQVEEA  180
DDWLRYGNPW EKARPEYMRP VKFYGRTEHT PEGVKWVDTQ VVLALPYDTP IPGYRNNIVN  240
TMRLWSAKAP CDFNLKDFNV GGYIQAVLDR NLCENISRVL YPNDNFFEGK ELRLKQEYFV  300
VAATLQDIVR RFKASKFGSR EIVRTDFAQL PNKVAIQLND THPAMAIPEL MRVLVDEEKL  360
EWDKAWDVCV RTCAYTNHTV LPEALERWPI DLFHHLLPRH LEIIYEINRR FLQYVASKFP  420
GDNDRLRRMS LIEEGECKKV NMAHMCIVGS HAVNGVARIH SEILVATLFK DFYELDPHKF  480
QNKTNGITPR RWLVMCNPGL AEVIAERIGE EFVRDLDQLK KLLKFIDDDA FIRDIAKVKQ  540
ENKLKFAVHL EEHYKVKINP QSMFDFQVKR IHEYKRQLLN CLHMITYYNR IKKEPNKHWT  600
PRTIMVGGKA APGYHTAKMI IRLITAIGEV VNHDPVIGDR LKVIFLENYR VTLAEKAIPS  660
ADLSEQISTA GTEASGTGNM KFMLNGALTI GTMDGANVEM AEEAGEKNLF IFGMRVEEVD  720
AMDAGKGYHA SEYYNRIPEL KQAMDQISGG FFSHKQPDLF KELVDLLMHH DRFKVFADYE  780
AYIKSQDKVN ELYKKPKEWT KMVIHNIAGC GKFSSDRTIS QYAREIWGME PSLEKIPAPD  840
EQLK                                                              844

SEQ ID NO: 11          moltype = AA  length = 9
FEATURE                Location/Qualifiers
REGION                 1..9
                       note = Alpha-1,4 glucan phosphorylase fragment
source                 1..9
                       mol_type = protein
                       organism = synthetic construct
SEQUENCE: 11
IPAPDEQLK                                                         9

SEQ ID NO: 12          moltype = AA  length = 17
FEATURE                Location/Qualifiers
REGION                 1..17
                       note = Alpha-1,4 glucan phosphorylase fragment
source                 1..17
                       mol_type = protein
                       organism = synthetic construct
SEQUENCE: 12
QISVRGLAGV ENVAELK                                                17

SEQ ID NO: 13          moltype = AA  length = 25
FEATURE                Location/Qualifiers
REGION                 1..25
                       note = Alpha-1,4 glucan phosphorylase fragment
source                 1..25
                       mol_type = protein
                       organism = synthetic construct
SEQUENCE: 13
AIPSADLSEQ ISTAGTEASG TGNMK                                       25

SEQ ID NO: 14          moltype = AA  length = 9
FEATURE                Location/Qualifiers
REGION                 1..9
                       note = Alpha-1,4 glucan phosphorylase fragment
source                 1..9
                       mol_type = protein
                       organism = synthetic construct
SEQUENCE: 14
DFYELDPHK                                                         9

SEQ ID NO: 15          moltype = AA  length = 10
FEATURE                Location/Qualifiers
REGION                 1..10
                       note = Alpha-1,4 glucan phosphorylase fragment
source                 1..10
                       mol_type = protein
                       organism = synthetic construct
SEQUENCE: 15
```

```
FAVHLEEHYK                                                         10

SEQ ID NO: 16          moltype = AA  length = 15
FEATURE                Location/Qualifiers
REGION                 1..15
                       note = Alpha-1,4 glucan phosphorylase fragment
source                 1..15
                       mol_type = protein
                       organism = synthetic construct
SEQUENCE: 16
GYHASEYYNR IPELK                                                   15

SEQ ID NO: 17          moltype = AA  length = 9
FEATURE                Location/Qualifiers
REGION                 1..9
                       note = Alpha-1,4 glucan phosphorylase fragment
source                 1..9
                       mol_type = protein
                       organism = synthetic construct
SEQUENCE: 17
IPAPDEQLK                                                          9

SEQ ID NO: 18          moltype = DNA  length = 2574
FEATURE                Location/Qualifiers
misc_feature           1..2574
                       note = Elongation factor 2
source                 1..2574
                       mol_type = other DNA
                       organism = synthetic construct
SEQUENCE: 18
atggtgaact ttacagtgga ccagatccgt gccatcatgg acaagaaatc caacattcgt  60
aacatgtctg tgatcgctca cgtggaccac ggcaagtcca cgctgaccga ctccctggtg  120
tctaaagccg ggatcatcgc ggggtctcgc gccggagaga cacgcttcac agacactcgc  180
aaagacgagc aggagcgctg tattaccatc aagtccacgg ctatctcgat gtactatgag  240
ctgggggaaa acgacatggc cttcatcaag cagtctaagg atgggcttgg cttcctcatc  300
aacctgattg actcaccggg ccatgtggac ttctcctctg aggtcacagc cgcccttagg  360
gtcaccgacg gcgccctggt ggtggttgac tgcgtctcag gtgtgtgtgt gcagacagag  420
accgtgttga ggcaggccat tgctgagcgc atcaagccag tgctgatgat gaacaagatg  480
gaccgggccc tgctggagct gcagctggag cctgaggacc tgttccagac cttccagcgc  540
atcgtggaga atgtcaacgt catcattgcc acctacggag aggatgaagc gggaccaatg  600
ggtgccatca tgattgaccc tgtgattggt accgtggggt ttgggtctgg cctccacggc  660
tgggccttca ctctaaagca gtttgctgag atgtacgtga caaagttttc tgccggcaaa  720
gacacccagc tgggatcggc ggagaggtgt aagaaggtgg aggacatgat gaagaagctg  780
tggggggaga ggttttttga cccagccact gggaagttca gtaagtccaa cctcggccct  840
gacggtaaga agctgccccg caccttctct cagctggtcc tggaccctat cttcaaggta  900
tttgatgcca tcatgaactt caagaaggat gagacagcca agctgataga gaagctggac  960
atcaagctgg actctgagga caaggagaag gagggcaagc ccctgttgaa ggcagtgatg  1020
cgtcgctggc tcccagccgg agaagccctg ctccagatga tcaccatcca cctgccctcc  1080
cccgtcacgg cccagaagta ccgctgtgag ctgctctacg agggaccagg agacgacgag  1140
gccgccatgg gtatcaagaa ctgcgacccc aaggctcccc tgatgatgta catatctaag  1200
atggtgccca ccacagacaa gggtcgcttc tatgcctttg gccgtgtgtt ctctggctgt  1260
gtgtccaccg gtctgaaggt gcgcatcatg ggaccaaact tcacccctgg gaagaaggaa  1320
gacctctaca tcaagcccat ccagaggacc attctgatga tggggcgtta tgtggagccc  1380
attgaggatg taccatgtgg gaacatcgtt gggctggttg gagttgacca gtatctgatt  1440
aagactggga ccatcaccac ctttgaacag gcccacaaca tgcgtgtgat gaagttcagc  1500
gtcagccctg tggtgagggt ggctgtggag gccaagaacc ctgctgacct gcccaagctg  1560
gtggaggggc tgaagcgtct ggccaagtct gaccccatgg tgcagtgtat catcgaggag  1620
tctggagagc acatcatcgc cggggccgga gagcttcatc tggagatctg tctcaaggat  1680
ctggaggagg accacgccgg cattcccctg aagaaatctg atccagtggt gtcctacagg  1740
gagactgtgt ctgaggagtc tgaagtgatg tgtctatcca agtcccctaa caagcacaac  1800
cgtctgtaca tgcgggctaa acctttccct gacggcctgg ccgaggacat cgagaagggg  1860
gacgtcagcc cccgacagga gctgaaaatc cgcgcccgtt tcctggctga caagtacgag  1920
tgggacgtgt cggaggcccg taagatctgg tgcttcggcc ctgacggtac cggtcccaac  1980
ctgctgatgg atgttaccaa gggagtccag tacctgaatg agatcaagga cagtgttgtg  2040
gctggcttcc agtgggctgt caaggagggt gtgttgtgtg aggagaacat gcgtgcagtc  2100
cgcttcgaca tccacgacgt gaccctgcac acagacgcaa ttcaccgcgg tggcggacag  2160
atcatcccca cggcccgcag agtgctgtat gcctgccagc tcaccgccca gccacgactc  2220
atggagccgg tctacttagt ggagatccag tgcccagagc aggtagtggg tgggatctac  2280
ggcgtgctga acaggaagcg aggccatgtg ttcgaggagt cccaggtgat gggcacgccc  2340
atgttcatcg tcaaggccta cctgcctgtc aacgagtcat ttgggttcac cgctgacctg  2400
cgctccaaca cgggcggcca ggctttcccc cagtgtgtgt ttgatcactg gcagatcctc  2460
cagggagatc cccaggaccc caccaccaag accgccattg tggtggccga gaccaggaaa  2520
cgcaaggggc tgaaagaggg catcccggcc ctggacaact acctggacaa attg        2574

SEQ ID NO: 19          moltype = AA  length = 858
FEATURE                Location/Qualifiers
REGION                 1..858
                       note = Elongation factor 2
source                 1..858
```

```
                        mol_type = protein
                        organism = synthetic construct
SEQUENCE: 19
MVNFTVDQIR AIMDKKSNIR NMSVIAHVDH GKSTLTDSLV SKAGIIAGSR AGETRFTDTR  60
KDEQERCITI KSTAISMYYE LGENDMAFIK QSKDGLGFLI NLIDSPGHVD FSSEVTAALR  120
VTDGALVVVD CVSGVCVQTE TVLRQAIAER IKPVLMMNKM DRALLELQLE PEDLFQTFQR  180
IVENVNVIIA TYGEDEAGPM GAIMIDPVIG TVGFGSGLHG WAFTLKQFAE MYVTKFSAGK  240
DTQLGSAERC KKVEDMMKKL WGERFFDPAT GKFSKSNLGP DGKKLPRTFS QLVLDPIFKV  300
FDAIMNFKKD ETAKLIEKLD IKLDSEDKEK EGKPLLKAVM RRWLPAGEAL LQMITIHLPS  360
PVTAQKYRCE LLYEGPGDDE AAMGIKNCDP KAPLMMYISK MVPTTDKGRF YAFGRVFSGC  420
VSTGLKVRIM GPNFTPGKKE DLYIKPIQRT ILMMGRYVEP IEDVPCGNIV GLVGVDQYLI  480
KTGTITTFEQ AHNMRVMKFS VSPVVRVAVE AKNPADLPKL VEGLKRLAKS DPMVQCIIEE  540
SGEHIIAGAG ELHLEICLKD LEEDHAGIPL KKSDPVVSYR ETVSEESEVM CLSKSPNKHN  600
RLYMRAKPFP DGLAEDIEKG DVSPRQELKI RARFLADKYE WDVSEARKIW CFGPDGTGPN  660
LLMDVTKGVQ YLNEIKDSVV AGFQWAVKEG VLCEENMRAV RFDIHDVTLH TDAIHRGGGQ  720
IIPTARRVLY ACQLTAQPRL MEPVYLVEIQ CPEQVVGGIY GVLNRKRGHV FEESQVMGTP  780
MFIVKAYLPV NESFGFTADL RSNTGGQAFP QCVFDHWQIL QGDPQDPTTK TAIVVAETRK  840
RKGLKEGIPA LDNYLDKL                                                858

SEQ ID NO: 20           moltype = AA  length = 10
FEATURE                 Location/Qualifiers
REGION                  1..10
                        note = Elongation factor 2 fragment
source                  1..10
                        mol_type = protein
                        organism = synthetic construct
SEQUENCE: 20
TAIVVAETRK                                                         10

SEQ ID NO: 21           moltype = AA  length = 12
FEATURE                 Location/Qualifiers
REGION                  1..12
                        note = Elongation factor 2 fragment
source                  1..12
                        mol_type = protein
                        organism = synthetic construct
SEQUENCE: 21
DLEEDHAGIP LK                                                      12

SEQ ID NO: 22           moltype = AA  length = 13
FEATURE                 Location/Qualifiers
REGION                  1..13
                        note = Elongation factor 2 fragment
source                  1..13
                        mol_type = protein
                        organism = synthetic construct
SEQUENCE: 22
DLEEDHAGIP LKK                                                     13

SEQ ID NO: 23           moltype = AA  length = 12
FEATURE                 Location/Qualifiers
REGION                  1..12
                        note = Elongation factor 2 fragment
source                  1..12
                        mol_type = protein
                        organism = synthetic construct
SEQUENCE: 23
DSVVAGFQWA VK                                                      12

SEQ ID NO: 24           moltype = AA  length = 10
FEATURE                 Location/Qualifiers
REGION                  1..10
                        note = Elongation factor 2 fragment
source                  1..10
                        mol_type = protein
                        organism = synthetic construct
SEQUENCE: 24
GDVSPRQELK                                                         10

SEQ ID NO: 25           moltype = DNA  length = 1989
FEATURE                 Location/Qualifiers
misc_feature            1..1989
                        note = Heat shock cognate 70 kDa protein
source                  1..1989
                        mol_type = other DNA
                        organism = synthetic construct
SEQUENCE: 25
atgtcaaagg gaccagcagt tggcattgac ctgggcacca cctactcctg tgtgggtgtg  60
tttcagcatg gcaaagtgga gatcatagcc aacgaccagg gaaacaggac cacacccagt  120
```

```
tatgtcgcct tcacagacac agaaaggctg attggggacg cagccaagaa ccaagtggcc  180
atgaacccca caaacacagt gtttgatgct aagcggctga tagggcggaa gtttgacgac  240
agtgtcgtcc aggcagacat gaaacactgg ccgtttacag tgatcaacga ctcgacacgg  300
cccaaggtcc aagtggagta caagggagag accaaggcct tctacccaga ggagatctcc  360
tccatggtgc tggtcaagat gaaggagatt gcagaggcct acctgggcaa gactataacc  420
aatgcagtgg tcactgtgcc agcttacttc aacgactctc agcgccaggc caccaaagat  480
gcagggacta tctcaggact caacgtactc cgcatcatca atgagccaac tgctgctgct  540
atcgcctatg gcctggacaa gaaggtggga gtggagagaa acgtcctaat ctttgaccta  600
ggcggaggta cgtttgatgt gtctatcctg accatcgaag acgggatctt tgaggtgaag  660
tccacggccg gagacaccca tcttggagga gaggacttcg acaaccgcat ggtcaaccac  720
ttcatctctg agttcaagcg caaatacaag aaggacatca gcgataacaa gagggccgtg  780
cgtcgtctgc gcaccgcctg tgaacgtgcc aagcgcaccc tgtcctccag tacccaggcc  840
agcattgaga ttgactctct gtatgagggc gtcgacttct acacctccat caccagggct  900
cgctttgagg agctgaacgc tgacctgttc agaggcaccc tggaccccgt ggagaagtct  960
ctgagggacg ccaagatgga caaggcccag gttcacgaca tcgtcctagt gggaggctcc  1020
acacgcatcc ccaagatcca aaagttgctg caggacttct tcaatgggaa ggagctcaac  1080
aagagcatca accctgatga ggcggttgcc tatggtgcag ctgttcaggc ggccatcttg  1140
tccggagaca agtctgagaa cgtgcaggac ctgctgctgc tggacgtcac gccactgtcc  1200
ctgggcattg agacggccgg aggggtcatg accgtgctca tcaagaggaa caccaccatc  1260
cccaccaagc agacgcagac cttcacaaca tactcagaca accagcctgg ggtgctcatt  1320
caggtatatg agggggaaag agccatgacc aaagacaaca acctactggg gaagtttgag  1380
ttgtgtggga ttccaccagc cccccggggt gtgcctcaga tcgaggtcac ctttgacatt  1440
gacgccaacg gcatcatgaa cgtgtctgcc gctgacaaga gcaccggcaa ggagaataag  1500
atcaccatca ccaatgacaa aggtcgtctg agtaaggagg acatagagcg catggtccag  1560
gaggctgaac agtacaaagc tgcggacgat gtccagaggg acaaggtggc gtccaagaat  1620
ggcctggagt catacgcctt caacatgaag tccaccgtgg aggacgagaa gctcaagggc  1680
aagctcagcg acgaggacaa acagaagatc ctggacaaat gcaatgaggt catcagctgg  1740
ctggacaaga accagtctgc agagaaggag gagtttgagc accaccagaa ggagctggag  1800
aaggtctgta accccatcat caccaagctg taccagggtg ctgggggggat gcctggaggg  1860
atgcctggag ggatgcctgg agggatgcct ggagggatgc ctgggggggat gcctggaggg  1920
atgcccgggg ctggtggtgc cgcacccgga ggaggtggat cctctggacc aacaattgag  1980
gaagtcgac                                                          1989

SEQ ID NO: 26          moltype = AA  length = 663
FEATURE                Location/Qualifiers
REGION                 1..663
                       note = Heat shock cognate 70 kDa protein
source                 1..663
                       mol_type = protein
                       organism = synthetic construct
SEQUENCE: 26
MSKGPAVGID LGTTYSCVGV FQHGKVEIIA NDQGNRTTPS YVAFTDTERL IGDAAKNQVA  60
MNPTNTVFDA KRLIGRKFDD SVVQADMKHW PFTVINDSTR PKVQVEYKGE TKAFYPEEIS  120
SMVLVKMKEI AEAYLGKTIT NAVVTVPAYF NDSQRQATKD AGTISGLNVL RIINEPTAAA  180
IAYGLDKKVG VERNVLIFDL GGGTFDVSIL TIEDGIFEVK STAGDTHLGG EDFDNRMVNH  240
FISEFKRKYK KDISDNKRAV RRLRTACERA KRTLSSSTQA SIEIDSLYEG VDFYTSITRA  300
RFEELNADLF RGTLDPVEKS LRDAKMDKAQ VHDIVLVGGS TRIPKIQKLL QDFFNGKELN  360
KSINPDEAVA YGAAVQAAIL SGDKSENVQD LLLLDVTPLS LGIETAGGVM TVLIKRNTTI  420
PTKQTQTFTT YSDNQPGVLI QVYEGERAMT KDNNLLGKFE LCGIPPAPRG VPQIEVTFDI  480
DANGIMNVSA ADKSTGKENK ITITNDKGRL SKEDIERMVQ EAEQYKAADD VQRDKVASKN  540
GLESYAFNMK STVEDEKLKG KLSDEDKQKI LDKCNEVISW LDKNQSAEKE EFEHHQKELE  600
KVCNPIITKL YQGAGGMPGG MPGGMPGGMP GGMPGGMPGG MPGAGGAAPG GGGSSGPTIE  660
EVD                                                                663

SEQ ID NO: 27          moltype = AA  length = 14
FEATURE                Location/Qualifiers
REGION                 1..14
                       note = Heat shock cognate 70 kDa protein fragment
source                 1..14
                       mol_type = protein
                       organism = synthetic construct
SEQUENCE: 27
AFYPEEISSM VLVK                                                    14

SEQ ID NO: 28          moltype = AA  length = 14
FEATURE                Location/Qualifiers
REGION                 1..14
                       note = Heat shock cognate 70 kDa protein fragment
source                 1..14
                       mol_type = protein
                       organism = synthetic construct
SEQUENCE: 28
EDIERMVQEA EQYK                                                    14

SEQ ID NO: 29          moltype = AA  length = 14
FEATURE                Location/Qualifiers
REGION                 1..14
                       note = Heat shock cognate 70 kDa protein fragment
source                 1..14
```

```
                        mol_type = protein
                        organism = synthetic construct
SEQUENCE: 29
HWPFTVINDS TRPK                                                      14

SEQ ID NO: 30           moltype = AA  length = 14
FEATURE                 Location/Qualifiers
REGION                  1..14
                        note = Heat shock cognate 70 kDa protein fragment
source                  1..14
                        mol_type = protein
                        organism = synthetic construct
SEQUENCE: 30
NQSAEKEEFE HHQK                                                      14

SEQ ID NO: 31           moltype = AA  length = 22
FEATURE                 Location/Qualifiers
REGION                  1..22
                        note = Heat shock cognate 70 kDa protein fragment
source                  1..22
                        mol_type = protein
                        organism = synthetic construct
SEQUENCE: 31
TITNAVVTVP AYFNDSQRQA TK                                             22

SEQ ID NO: 32           moltype = DNA  length = 2061
FEATURE                 Location/Qualifiers
misc_feature            1..2061
                        note = Serotransferrin
source                  1..2061
                        mol_type = other DNA
                        organism = synthetic construct
SEQUENCE: 32
atgaaactgc ttctcgtctc agcgctgctg ggtgcttcg ctacggtgta tgctgcccca  60
gctgagggaa tggttagatg gtgcgtaaag tcggaaaaag agctgaagaa atgccacgat  120
ctcgcagcca atgtggcggg gttttcatgc gtgaggaggg acgactctct tgaatgcatc  180
caagccatca agagggaaga ggctgatgct atcactctgg atggaggaga tatttacata  240
gctggcctcc acaactacaa cctgcagccc atcattgcag aggactatgg tgaggactct  300
gacacctgct attatgctgt ggccgtggcc aaaaagggca ctgaatttgg gttcctcgac  360
ctccgtggca agaagtcctg ccacaccggg ttgggcaaat ctgcaggctg gaacattccc  420
atcggtaccc tggtgactgt gggccagatc caatgggccg gcatcgagga cagacctgtg  480
gagtcggcgg tgagcgactt cttcaatgcc agctgtgctc caggagccaa tagggattct  540
caactgtgcc agttgtgtat gggagactgc tccagatctc acaacgagcc ctactatgac  600
tattccgggg ccttccagtg cctgaaggat ggagcaggag aggttgcctt catcaagcac  660
ctgactgtac ctgccgcaga gaaggcaagc tatgagttgc tgtgcaagga taacaccaga  720
gctcccatcg acagctacaa gacctgccac ctggccagag tacccgccca cgctgtggtc  780
agccgcaagg accccaggct ggccaatctc atctacagca agctgatggc cgtcacgaac  840
ttcaacctgt tctcctccga tggttatgct gccaagaacc tgatgttcaa ggactccact  900
cagaatctag tacagctgcc aatgaccacc gactccttcc tctacctggg agctgagtac  960
atgagcacta tacgctccct gacaaaagcg caggccacag gtgtcacctc cagggccatc  1020
aaatggtgtg ccgtgggcca taaggagaag gtcaagtgtg acgcctggac aatcaacagc  1080
ttcacagatg gtgactccag gatcgaatgc caggacgcac ccacagtgga tgaatgcatc  1140
aagaagatca tgcgtaaaga ggcagatgcc atagcggtgg atggtgggga ggtgttcact  1200
gctggaaaat gtggtctggt ccctgtcatg gtggagcagt atgatgaagt tcggtgcagc  1260
gcccctggtg aggcgtcatc ctactttgcg gtggcggtgg caaagagggg atctgggttg  1320
acctggacaa ccctgaaggg caagaggtca tgccacaccg gcttgggcag gaccgcaggc  1380
tggaacatac ccatgggtct tatccatagg aggactatga actgcgactt caccacatac  1440
ttcagtaagg gctgtgctcc tggatttgag gtggactctc ccttctgtgc ccagtgtaag  1500
ggcagtggga agtccgtggg aggagatggg tccaagtgca aagccagctc tgaagagcag  1560
tactacggct ataacggagc attcagatgt ctggttgaag atgctggaga tgttgccttc  1620
attaaacaca ctattgtacc agagatgact gatggtagtg gtccagtttg ggcacagaac  1680
ctgatgtcct ctgactttga actactctgc caggatggta ctaccaagcc agtcacacat  1740
ttccgtgagt gccacctggc caaggtgccc gcccatgctg tgataacacg cccagagtcc  1800
cgtggagagg ttgtgtccat ccttctggag cagcaggcca ggttcggctc aagcggcagc  1860
gattcctcat ttaatatgtt caagccagat tttggaaaga acttgctctt caaggattcc  1920
acaaagtgtc tccaggagat cccaagcggc accaaattcc agggtttcct tggggaagag  1980
tacatgatcg ccatgcaatc gctcagggag tgctccaaca gtacctcaga tttggagaag  2040
gcatgcactt tccattcctg c                                              2061

SEQ ID NO: 33           moltype = AA  length = 687
FEATURE                 Location/Qualifiers
REGION                  1..687
                        note = Serotransferrin
source                  1..687
                        mol_type = protein
                        organism = synthetic construct
SEQUENCE: 33
MKLLLVSALL GCFATVYAAP AEGMVRWCVK SEKELKKCHD LAANVAGFSC VRRDDSLECI  60
QAIKREEADA ITLDGGDIYI AGLHNYNLQP IIAEDYGEDS DTCYYAVAVA KKGTEFGFLD  120
```

-continued

```
LRGKKSCHTG LGKSAGWNIP IGTLVTVGQI QWAGIEDRPV ESAVSDFFNA SCAPGANRDS  180
QLCQLCMGDC SRSHNEPYYD YSGAFQCLKD GAGEVAFIKH LTVPAAEKAS YELLCKDNTR  240
APIDSYKTCH LARVPAHAVV SRKDPRLANL IYSKLMAVTN FNLFSSDGYA AKNLMFKDST  300
QNLVQLPMTT DSFLYLGAEY MSTIRSLTKA QATGVTSRAI KWCAVGHKEK VKCDAWTINS  360
FTDGDSRIEC QDAPTVDECI KKIMRKEADA IAVDGGEVFT AGKCGLVPVM VEQYDEVRCS  420
APGEASSYFA VAVAKRGSGL TWTTLKGKRS CHTGLGRTAG WNIPMGLIHR RTMNCDFTTY  480
FSKGCAPGFE VDSPFCAQCK GSGKSVGGDG SKCKASSEEQ YYGYNGAFRC LVEDAGDVAF  540
IKHTIVPEMT DGSGPVWAQN LMSSDFELLC QDGTTKPVTH FRECHLAKVP AHAVITRPES  600
RGEVVSILLE QQARFGSSGS DSSFNMFKPD FGKNLLFKDS TKCLQEIPSG TKFQGFLGEE  660
YMIAMQSLRE CSNSTSDLEK ACTFHSC                                      687

SEQ ID NO: 34          moltype = AA  length = 12
FEATURE                Location/Qualifiers
REGION                 1..12
                       note = Serotransferrin fragment
source                 1..12
                       mol_type = protein
                       organism = synthetic construct
SEQUENCE: 34
AQATGVTSRA IK                                                     12

SEQ ID NO: 35          moltype = AA  length = 10
FEATURE                Location/Qualifiers
REGION                 1..10
                       note = Serotransferrin fragment
source                 1..10
                       mol_type = protein
                       organism = synthetic construct
SEQUENCE: 35
ATGVTSRAIK                                                        10

SEQ ID NO: 36          moltype = AA  length = 11
FEATURE                Location/Qualifiers
REGION                 1..11
                       note = Serotransferrin fragment
source                 1..11
                       mol_type = protein
                       organism = synthetic construct
SEQUENCE: 36
DPRLANLIYS K                                                      11

SEQ ID NO: 37          moltype = AA  length = 12
FEATURE                Location/Qualifiers
REGION                 1..12
                       note = Serotransferrin fragment
source                 1..12
                       mol_type = protein
                       organism = synthetic construct
SEQUENCE: 37
GTEFGFLDLR GK                                                     12

SEQ ID NO: 38          moltype = AA  length = 13
FEATURE                Location/Qualifiers
REGION                 1..13
                       note = Serotransferrin fragment
source                 1..13
                       mol_type = protein
                       organism = synthetic construct
SEQUENCE: 38
KGTEFGFLDL RGK                                                    13

SEQ ID NO: 39          moltype = AA  length = 14
FEATURE                Location/Qualifiers
REGION                 1..14
                       note = Serotransferrin fragment
source                 1..14
                       mol_type = protein
                       organism = synthetic construct
SEQUENCE: 39
KGTEFGFLDL RGKK                                                   14

SEQ ID NO: 40          moltype = AA  length = 18
FEATURE                Location/Qualifiers
REGION                 1..18
                       note = Serotransferrin fragment
source                 1..18
                       mol_type = protein
                       organism = synthetic construct
SEQUENCE: 40
```

```
LMAVTNFNLF SSDGYAAK                                            18

SEQ ID NO: 41          moltype = AA  length = 11
FEATURE                Location/Qualifiers
REGION                 1..11
                       note = Serotransferrin fragment
source                 1..11
                       mol_type = protein
                       organism = synthetic construct
SEQUENCE: 41
RGSGLTWTTL K                                                   11

SEQ ID NO: 42          moltype = DNA  length = 1518
FEATURE                Location/Qualifiers
misc_feature           1..1518
                       note = Myosin binding protein H-like
source                 1..1518
                       mol_type = other DNA
                       organism = synthetic construct
SEQUENCE: 42
atgcctgcga agcctgcccc tatcaagaag gcagccccga aagagcctgc tcctaagaag  60
gaggaagcac ctgcacctgc acccgcggag gcggctcctg ctgaagttgc tccccctgcc  120
gaggtcgaag ctccaccggc agaggctgcc cctgccgaag cagctgcccc tgctgaggca  180
gctccaaccg aagaaaaggc tcccgcagaa cccgcgcctg agcagcccaa agcacccaca  240
cccccctcctc cagatgagcc caccagtgag cccctggaag tgacagtgga cgacaagagc  300
gacacttcag tgaccatcac ctggaggcct ccaaagacta ttccagccaa ctctggcctg  360
gatggataca ctgtggaaat caccaaggag ggaactgaag actggaaagc agccaacgag  420
gatctgaccg tgtcctgccg ttatgtcatc aagaaccaga ctaccggcga ccgtctgctg  480
atccgagtgg ttgctgtaaa ccctggtggc cgcagccccc ctgctaccat cgccgacccc  540
gttctggtca aggaggttgg ggctcgcccc aaagtccgcc tccctcgttt cctgaggcag  600
aggtatgtca agaaagtcgg cgagaagatc aacattgtca tcccgtactc tggcaaacct  660
aagccagtgg ttagctggtt aaaggatgga cagcccctcg actcaaagag ggccaacatc  720
cgtacatctg acagagacag catcctgttc atccgtcaag cagagagggt ggactctggc  780
tcatacgaaa tgtgcgtgaa ggtggacgac tttgaggaca aagctgctat catcatccag  840
attattgagt tacccgggcc accagccagc attaagattg tggatgtctg gggattcaac  900
gttgctttgg agtggaccgt acccaaagat aatggaaaca cagagatcac aggctacact  960
gtccagaaag ctgacaagaa gaccggggac tggttcaaca ttttggagca ctacgccaga  1020
ctaaatgcca ccatctcaga cctcattatg ggcaacacct acaccttcag ggtctttgca  1080
gagaacaagt gcggactcag tgaggaatgt gccgtgacca agggagaagc caccattgtg  1140
aaggaggtta ttgactacaa acctaccccg ttcgtggagc atgacttcac cgaggctccc  1200
aagttcacca ctgttctgaa cgacaggtcc accactgttg gctacagcac caagctgctg  1260
tgttctgtga ggggatgccc caagcctaag attatgtgga tgaagaacaa gatgattctc  1320
aacaacatgg acaaccccaa gtacaggatg atcagcacag gggcatctg caccctggag  1380
atccgtaagc ctggcccata cgacggtggt gagtatgtct gcagagccga gaatacactg  1440
gggaaggtcg acaccggctg caagctggag gtcagaaagc ctgggcaagc agatgctgac  1500
aaagacaaga aggaacag                                            1518

SEQ ID NO: 43          moltype = AA  length = 506
FEATURE                Location/Qualifiers
REGION                 1..506
                       note = Myosin binding protein H-like
source                 1..506
                       mol_type = protein
                       organism = synthetic construct
SEQUENCE: 43
MPAKPAPIKK AAPKEPAPKK EEAPAPAPAE AAPAEVAPPA EVEAPPAEAA PAEAAAPAEA  60
APTEEKAPAE PAPEQPKAPT PPPPDEPTSE PLEVTVDDKS DTSVTITWRP PKTIPANSGL  120
DGYTVEITKE GTEDWKAANE DLTVSCRYVI KNQTTGDRLL IRVVAVNPGG RSPPATIADP  180
VLVKEVGARP KVRLPRFLRQ RYVKKVGEKI NIVIPYSGKP KPVVSWLKDG QPLDSKRANI  240
RTSDRDSILF IRQAERVDSG SYEMCVKVDD FEDKAAIIIQ IIELPGPPAS IKIVDVWGFN  300
VALEWTVPKD NGNTEITGYT VQKADKKTGD WFNILEHYAR LNATISDLIM GNTYTFRVFA  360
ENKCGLSEEC AVTKGEATIV KEVIDYKPTP FVEHDFTEAP KFTTVLNDRS TTVGYSTKLL  420
CSVRGCPKPK IMWMKNKMIL NNMDNPKYRM ISTGGICTLE IRKPGPYDGG EYVCRAENTL  480
GKVDTGCKLE VRKPGQADAD KDKKEQ                                   506

SEQ ID NO: 44          moltype = AA  length = 18
FEATURE                Location/Qualifiers
REGION                 1..18
                       note = Myosin binding protein H-like fragment
source                 1..18
                       mol_type = protein
                       organism = synthetic construct
SEQUENCE: 44
AAIIIQIIEL PGPPASIK                                            18

SEQ ID NO: 45          moltype = AA  length = 18
FEATURE                Location/Qualifiers
REGION                 1..18
                       note = Myosin binding protein H-like fragment
```

```
source                  1..18
                        mol_type = protein
                        organism = synthetic construct
SEQUENCE: 45
AAPAEAAAPA EAAPTEEK                                              18

SEQ ID NO: 46           moltype = AA  length = 11
FEATURE                 Location/Qualifiers
REGION                  1..11
                        note = Myosin binding protein H-like fragment
source                  1..11
                        mol_type = protein
                        organism = synthetic construct
SEQUENCE: 46
APAEPAPEQP K                                                     11

SEQ ID NO: 47           moltype = AA  length = 14
FEATURE                 Location/Qualifiers
REGION                  1..14
                        note = Myosin binding protein H-like fragment
source                  1..14
                        mol_type = protein
                        organism = synthetic construct
SEQUENCE: 47
DNGNTEITGY TVQK                                                  14

SEQ ID NO: 48           moltype = AA  length = 20
FEATURE                 Location/Qualifiers
REGION                  1..20
                        note = Myosin binding protein H-like fragment
source                  1..20
                        mol_type = protein
                        organism = synthetic construct
SEQUENCE: 48
EVIDYKPTPF VEHDFTEAPK                                            20

SEQ ID NO: 49           moltype = AA  length = 17
FEATURE                 Location/Qualifiers
REGION                  1..17
                        note = Myosin binding protein H-like fragment
source                  1..17
                        mol_type = protein
                        organism = synthetic construct
SEQUENCE: 49
FTTVLNDRST TVGYSTK                                               17

SEQ ID NO: 50           moltype = AA  length = 10
FEATURE                 Location/Qualifiers
REGION                  1..10
                        note = Myosin binding protein H-like fragment
source                  1..10
                        mol_type = protein
                        organism = synthetic construct
SEQUENCE: 50
INIVIPYSGK                                                       10

SEQ ID NO: 51           moltype = AA  length = 19
FEATURE                 Location/Qualifiers
REGION                  1..19
                        note = Myosin binding protein H-like fragment
source                  1..19
                        mol_type = protein
                        organism = synthetic construct
SEQUENCE: 51
INIVIPYSGK PKPVVSWLK                                             19

SEQ ID NO: 52           moltype = AA  length = 33
FEATURE                 Location/Qualifiers
REGION                  1..33
                        note = Myosin binding protein H-like fragment
source                  1..33
                        mol_type = protein
                        organism = synthetic construct
SEQUENCE: 52
NQTTGDRLLI RVVAVNPGGR SPPATIADPV LVK                             33

SEQ ID NO: 53           moltype = AA  length = 13
FEATURE                 Location/Qualifiers
REGION                  1..13
```

```
                        note = Myosin binding protein H-like fragment
source                  1..13
                        mol_type = protein
                        organism = synthetic construct
SEQUENCE: 53
SDTSVTITWR PPK                                                    13

SEQ ID NO: 54           moltype = AA  length = 17
FEATURE                 Location/Qualifiers
REGION                  1..17
                        note = Myosin binding protein H-like fragment
source                  1..17
                        mol_type = protein
                        organism = synthetic construct
SEQUENCE: 54
TIPANSGLDG YTVEITK                                                17

SEQ ID NO: 55           moltype = DNA  length = 1377
FEATURE                 Location/Qualifiers
misc_feature            1..1377
                        note = Desmin (fragment)
source                  1..1377
                        mol_type = other DNA
                        organism = synthetic construct
SEQUENCE: 55
atttcctctt accgccgcac tttcggttct ggtattggat ccaccccagg catgtcctcc  60
atgttctccc acggtggacg cggctcctcc ggctcggccc acatgtcctc cagagtctac  120
gagatgacca aaagctccgc ccgccccagc tactcctccg gcagtattcg ctcctcctcc  180
ggcggcgcga tgcgctcgta cgccgggatg ggcgagaagc tggacttcaa cctggccgac  240
gccactaacc gcgacttcct ggacaccaga accaatgaga aggcagagtt gcagcacctg  300
aacgaccggt tcgccagcta catcgagaag gtccgtttcc tggagcagca gaacgctact  360
ctggtggtgg agatcgagag gctgaggggt cacgagccga cccgcgtggc cgagatgtac  420
gaggaggaga tgagagagct gaggcgtcag gtggacggca tgtccaatga ccgagcccgc  480
atggaggtgg agagagacaa cttggctgac gacctgcaga aactcaaact cagactgcag  540
gaggtgatcc accagaggga agaggcagag aacaacctgt ctgccttcag agctgacgtg  600
gactctgcca cgctggccag gctggacctg gagagacgca ttgaaagcct gcaggaggag  660
atcaccttcc tcaagaagat ccacgaggag gagatccatg agctgacgag ccagatgcag  720
gagacctcgg tgcaggtcca gatggacatg tccaaaccag acctgaccgt tgccctcagg  780
gacatccgta tgcagtacga gggtatcgca gccaagaaca tctctgaggc agaggactgg  840
tacaagtcca aggtgtcaga cctgaaccag gctgtgaaca agaacaacga tgctctgaga  900
caggccaaac aggagagcat ggagttcagg catcagatcc agtcctacac ctgtgagatc  960
gactctctca agggaaccaa cgagtctctg ctgaggcaga tgagggagat ggaggatcgt  1020
ctgggaaacg aggctggagg ttaccaggac tccgtcaccc gtctggaggc tgagatcgcc  1080
aagatgaagg atgagatggc tcgtcacctc agagagtacc aggacctcct caatgtcaag  1140
atggccctgg atatagagat cgctacctac aggaagctac tggagggaga ggagagccga  1200
atcactgtat ctggctccaa gtcttctcac tctggctccc actctgctgc ctcattatat  1260
tccactgttg gattcagaga gaccagccca gacgtcggac gatcagcaga ggtccactcc  1320
aagaagactg tcctgatcaa gaccatcgag acccgcgatg gagaggtcgt cagcgag     1377

SEQ ID NO: 56           moltype = AA  length = 459
FEATURE                 Location/Qualifiers
REGION                  1..459
                        note = Desmin (fragment)
source                  1..459
                        mol_type = protein
                        organism = synthetic construct
SEQUENCE: 56
ISSYRRTFGS GIGSTPGMSS MFSHGGRGSS GSAHMSSRVY EMTKSSARPS YSSGSIRSSS  60
GGAMRSYAGM GEKLDFNLAD ATNRDFLDTR TNEKAELQHL NDRFASYIEK VRFLEQQNAT  120
LVVEIERLRG HEPTRVAEMY EEEMRELRRQ VDGMSNDRAR MEVERDNLAD DLQKLKLRLQ  180
EVIHQREEAE NNLSAFRADV DSATLARLDL ERRIESLQEE ITFLKKIHEE EIHELTSQMQ  240
ETSVQVQMDM SKPDLTVALR DIRMQYEGIA AKNISEAEDW YKSKVSDLNQ AVNKNNDALR  300
QAKQESMEFR HQIQSYTCEI DSLKGTNESL LRQMREMEDR LGNEAGGYQD SVTRLEAEIA  360
KMKDEMARHL REYQDLLNVK MALDIEIATY RKLLEGEESR ITVSGSKSSH SGSHSAASLY  420
STVGFRETSP DVGRSAEVHS KKTVLIKTIE TRDGEVVSE                        459

SEQ ID NO: 57           moltype = AA  length = 17
FEATURE                 Location/Qualifiers
REGION                  1..17
                        note = A part of Desmin (fragment)
source                  1..17
                        mol_type = protein
                        organism = synthetic construct
SEQUENCE: 57
DEMARHLREY QDLLNVK                                                17

SEQ ID NO: 58           moltype = AA  length = 21
FEATURE                 Location/Qualifiers
REGION                  1..21
```

```
                         note = A part of Desmin (fragment)
source                   1..21
                         mol_type = protein
                         organism = synthetic construct
SEQUENCE: 58
LDFNLADATN RDFLDTRTNE K                                        21

SEQ ID NO: 59            moltype = AA  length = 10
FEATURE                  Location/Qualifiers
REGION                   1..10
                         note = A part of Desmin (fragment)
source                   1..10
                         mol_type = protein
                         organism = synthetic construct
SEQUENCE: 59
NISEAEDWYK                                                     10

SEQ ID NO: 60            moltype = DNA  length = 822
FEATURE                  Location/Qualifiers
misc_feature             1..822
                         note = Capping protein (Actin filament) muscle Z-line beta
source                   1..822
                         mol_type = other DNA
                         organism = synthetic construct
SEQUENCE: 60
atgaatgacc agcagctgga ctgtgctctg gacctgatga ggcgtcttcc tccccagcag  60
atcgagaaga atctcagtga cctcatcgac ctggtgccca gtctgtgtga ggacctactc  120
tcctctgtgg accagcctct gaagatcgcc cgggacaagg tagtggggaa agactacctg  180
ctctgtgact ataacagaga cggtgactcc tacagatccc catggagtaa taagtatgag  240
ccacccatcg acgatggtgc catgccatct gcccgcctgc gcaaactaga ggtggaagcc  300
aacaatgcct ttgaccagta tagagacctg tactttgagg gtggcgtatc gtctgtgtat  360
ctgtgggact tggatcatgg ctttgctggg gtcatcctca tcaagaaggc tggagacggc  420
tccaagaaga tcaaaggctg ctgggactcc atccatgtgg tggaggtgca ggagaagtcc  480
agcggacgga ccgctcacta caaactcacc tccaccgtca tgctgtggct ccagacgacc  540
aaggccgggt ctggaaccat gaacctgggt ggcagtctga caagacagat ggagaaagac  600
gagacagttg gagagtcttc cccacatatt gccaacatcg gccgcctggt ggaggatatg  660
gagaataaga ttcgctccac tctcaacgag atctactttg ggaagaccaa ggacatcgtc  720
aatggtttaa gatctattga ctctctgcct gataaccaaa agtaccggca gctccagaag  780
gagctgtctc aggtccttac ccagcgccag atcttcattg ac                 822

SEQ ID NO: 61            moltype = AA  length = 274
FEATURE                  Location/Qualifiers
REGION                   1..274
                         note = Capping protein (Actin filament) muscle Z-line beta
source                   1..274
                         mol_type = protein
                         organism = synthetic construct
SEQUENCE: 61
MNDQQLDCAL DLMRRLPPQQ IEKNLSDLID LVPSLCEDLL SSVDQPLKIA RDKVVGKDYL  60
LCDYNRDGDS YRSPWSNKYE PPIDDGAMPS ARLRKLEVEA NNAFDQYRDL YFEGGVSSVY  120
LWDLDHGFAG VILIKKAGDG SKKIKGCWDS IHVVEVQEKS SGRTAHYKLT STVMLWLQTT  180
KAGSGTMNLG GSLTRQMEKD ETVGESSPHI ANIGRLVEDM ENKIRSTLNE IYFGKTKDIV  240
NGLRSIDSLP DNQKYRQLQK ELSQVLTQRQ IFID                          274

SEQ ID NO: 62            moltype = AA  length = 24
FEATURE                  Location/Qualifiers
REGION                   1..24
                         note = Capping protein (Actin filament) muscle Z-line beta
                          fragment
source                   1..24
                         mol_type = protein
                         organism = synthetic construct
SEQUENCE: 62
DETVGESSPH IANIGRLVED MENK                                     24

SEQ ID NO: 63            moltype = AA  length = 17
FEATURE                  Location/Qualifiers
REGION                   1..17
                         note = Capping protein (Actin filament) muscle Z-line beta
                          fragment
source                   1..17
                         mol_type = protein
                         organism = synthetic construct
SEQUENCE: 63
DIVNGLRSID SLPDNQK                                             17

SEQ ID NO: 64            moltype = AA  length = 14
FEATURE                  Location/Qualifiers
REGION                   1..14
```

```
                        note = Capping protein (Actin filament) muscle Z-line beta
                         fragment
source                  1..14
                        mol_type = protein
                        organism = synthetic construct
SEQUENCE: 64
ELSQVLTQRQ IFID                                                           14

SEQ ID NO: 65           moltype = AA  length = 12
FEATURE                 Location/Qualifiers
REGION                  1..12
                        note = Capping protein (Actin filament) muscle Z-line beta
                         fragment
source                  1..12
                        mol_type = protein
                        organism = synthetic construct
SEQUENCE: 65
IRSTLNEIYF GK                                                             12

SEQ ID NO: 66           moltype = AA  length = 13
FEATURE                 Location/Qualifiers
REGION                  1..13
                        note = Capping protein (Actin filament) muscle Z-line beta
                         fragment
source                  1..13
                        mol_type = protein
                        organism = synthetic construct
SEQUENCE: 66
LTSTVMLWLQ TTK                                                            13

SEQ ID NO: 67           moltype = AA  length = 10
FEATURE                 Location/Qualifiers
REGION                  1..10
                        note = Capping protein (Actin filament) muscle Z-line beta
                         fragment
source                  1..10
                        mol_type = protein
                        organism = synthetic construct
SEQUENCE: 67
SIDSLPDNQK                                                                10

SEQ ID NO: 68           moltype = AA  length = 17
FEATURE                 Location/Qualifiers
REGION                  1..17
                        note = Capping protein (Actin filament) muscle Z-line beta
                         fragment
source                  1..17
                        mol_type = protein
                        organism = synthetic construct
SEQUENCE: 68
YEPPIDDGAM PSARLRK                                                        17

SEQ ID NO: 69           moltype = DNA  length = 5799
FEATURE                 Location/Qualifiers
misc_feature            1..5799
                        note = myosin heavy chain, fast skeletal muscle-like
source                  1..5799
                        mol_type = other DNA
                        organism = synthetic construct
SEQUENCE: 69
atgagtacgg acgcggagat gcaagtctac ggcaaggctg ccatatacct tcgtaagtct  60
gagaaggaga ggatggaggc acaagccatg ccctttgatt caaagaacgc ctgctatgtg  120
acagacaagg tggagctgta ccttaagggt ttagtcactg ccagggccga cgggaagtgt  180
actgtgacag ctttagactt tcgtgaagga aaagagttca aagatgcaga catctatgag  240
atgaaccccc ctaagtacga caagattgag gacatggcca tgatgaccta cctgaatgaa  300
gcctctgtgt tgtataacct caaagagcgt tatgcagcat ggatgatcta tacctactct  360
gggctcttct gtgccacggt gaacccctac aagtggctcc cagtgtacga cgaagaggtt  420
gtcaacgcct acagagggaa gaagagggtg gaggctccac cacatatctt ctccgtctct  480
gacaacgcct ttcagttcat gatgattgat aaggagaacc agtccgtcct gattactgga  540
gaatccggtg caggaaagac tgtcaacacc aagcgtgtca tccagtactt tgccaccatt  600
gcagtgtctg gtggcaagaa ggaagcagac cccaacaaaa tgcaggggtc tcttgaggat  660
cagatcattg cagctaaccc tctgctagag tcttacggta atgccaagac agtgaggaac  720
gacaactcgt ctcgctttgg taaattcatc aggattcact tccaagctgg taaactggct  780
aaagctgaca ttgagaccta cctgctggag aagtccagag tgtccttcca actgcccgat  840
gagagaggct accacatctt cttccagatg atgacaggcc acaaacctga gctagttgaa  900
ttggcactcc tcaccaccaa cccctacgac ttccccatgt gcagccaggg tcagattgct  960
gtggccagca tcaacgacaa tgaagagctg gatgccacag atgaagccat tacaatcctg  1020
ggcttcacta atgaggagaa gcttggaata tacaagctga caggagctgt agtgcaccat  1080
ggcaacttga aattcaagca gaagcagcgt gaggagcagg ccgagccaga cggcacagag  1140
```

```
gtggctgata aaatcgccta cctgctgggc ctgaactcag ctgagatgtt gaaagctctg  1200
tgctacccca gagtgaaggt cggcaacgag tatgtgacca agggacagac tgtggctcag  1260
gttaataact cagtcagtgc tctggccaag tccatctatg agaggatgtt cttgtggatg  1320
gtcatccgta tcaatgagat gttggacacc aagaatccaa ggcagttcta tatcggtgtg  1380
cttgacattg ccgggtttga gatctttgat tacaacagca tggagcagct gtgcatcaac  1440
ttcaccaatg agaaactgca acagtttttc aaccacacca tgttcgtcct ggagcaagag  1500
gagtacaaga aggagggaat cgtctgggcc ttcattgact tcggcatgga tttggctgcc  1560
tgcattgagc ttattgagaa gccattgggc atcttctcca tccttgaaga ggagtgcatg  1620
ttccccaagt cttcagacac taccttcaag gacaagctgt acgcccagca tcttggtaaa  1680
acaaaggcgt ttgagaagcc caagcctgcc aaaggcaagg cagaggccca cttctccctg  1740
gtgcattacg ccggtactgt ggactacaac atcactggct ggctggagaa gaacaaggac  1800
cccttgaacg actcagtttg tcaactgtat gggaagtccg gagtcaaaat tttggctgcc  1860
ctgtatcccc ctccccctcc tgaggataaa gccaagaaag gaggcaagaa gaagggtggt  1920
tccatgcaga ctgtgtcctc ccagttcagg gagaacttac ataagctgat gaccaacttg  1980
aggagcactc atcctcactt tgtgcgctgc ctgatcccca acgagtcaaa gactccaggt  2040
ctgatggaga acttcctggt tatccaccag ctcaggtgta atggtgtact ggagggtatc  2100
aggatctgca gaaagggctt ccccagcaga atcatctatg ctgacttcaa gcaaaggtac  2160
aaagtactga atgccagcgt catccctgag ggccagttca tggacaacaa gaaggcttct  2220
gagaagctgc ttggatccat tgatgtgaat cacgaggatt acaagtttgg acacaccaag  2280
gtgttcttca aagccggtct gctgggtgtc ctggaggaga tgagagatga gaagctggcc  2340
tctctagtcg gcatgctcca ggctctcagc cgtggattcc tcatgaggag agagttcacc  2400
aagatgatgg agaggagaga atcaatttac tccatccagt acaacatccg ctcattcatg  2460
aatgtgaaaa cctggccatg gatgaagttg tacttcaaga tcaagcccct gctgcagagc  2520
gctgagactg agaaggagct ggccaacatg aaggagaact atgagaaaat gaagacagac  2580
ctggccaagg ctctgtctac aaagaagcaa atggaggaga agttggtgtc cctgacgcag  2640
gagaagaacg acctggcact ccaagtcgca tctgaaggag agagtctgaa cgatgctgag  2700
gaaaggtgcg aggggctcat caagagcaag atccagcagg aggccaaact caaagagacg  2760
accgagaggc tggaggatga ggaggagatc aatgctgagt tgactgccaa gaagaggaag  2820
ctggaggatg agtgctctga gctgaagaag gacattgatg atctggagct caccctggcc  2880
aaagtggaga aggagaagca cgccactgaa aacaaggtta aaaacctgac agaggagatg  2940
gcgtctatgg atgagagtgt tgccaagctg accaaggaga agaaagccct acaagaggcc  3000
caccagcaga cactggatga cctgcaggca gaggaggaca aagtcaacac tctgaccaag  3060
gccaagacca agctggaaca gcaagtggac gaccttgagg gttctctgga gcaagagaag  3120
aagctccgca tggaccttga gagatccaag agaaagctgg agggagatct gaaactggcc  3180
caggagtcca taatggacct ggagaatgac aagcagcaag ctgatgagaa aatcaagaag  3240
aaggagtttg agaccactca gctcctcagc aaggttgagg atgagcagtc tctgggagct  3300
cagctgcaga agaagatcaa ggaactccag gcccgtattg aggaactgga ggaggaaatt  3360
gaggctgagc gtgctgccag ggctaaggtt gagaagcaga gggctgatct ctccagggaa  3420
cttgaggaga tcagcgagag gctggaggag gccggaggcg ccactgctgc tcagattgag  3480
atgaacaaga agcgtgaggc tgagttccag aagctgcgtc gtgatcttga agagtccacc  3540
ctgcagcatg aggccacagc cgccgctctg cgcaagaagc aggccgacag tgtggctgag  3600
ctcggggagc agatcgacaa cctgcagcgc gtcaagcaga agctggagaa ggagaagagc  3660
gagtacaaga tggagattga tgacctctcc agcaacatgg aggccgttgc caaggctaag  3720
ggcaatctag agaagatgtg ccgtactctt gaggaccagc tgagcgagct caagactaag  3780
aatgatgaga atgttcgcca ggtcaacgac atcagcggac agagggccag actcctgaca  3840
gaaaatggtg agtttggtag gcagctggag gagaaggaag ccctggtgtc tcagctgacc  3900
agaggcaaac aggccttcac ccagcaggtg gaggagctga agagggcgat tgaggaggag  3960
gtcaaggcta aaaatgcact ggcccacgga gttcagtctg cccgccatga ctgtgacctc  4020
ctgagggagc agtttgagga ggagcaggag gccaaggcag agctgcaacg cggcatgtcc  4080
aaggccaata gtgaggtggc tcagtggagg actaagtatg aaactgatgc catccagcgc  4140
acagaggagc tggaggaggc caagaagaag ctggcccagc gtctgcagga tgccgaggag  4200
accattgagg cgaccaactc caagtgcgcc tccctggaga agaccaagca gagactacag  4260
ggagaggtgg aggacctcat gattgatgtt gagagagcca acgcattggc cgccaacctc  4320
gacaagaagc agaggaactt tgacaaggtt ctggcagagt ggaagcagaa gtatgaggag  4380
ggtcaggctg agctggaagg agctcagaag gaggctcgct ctatgagcac tgagctcttc  4440
aagatgaaga actcctacga ggaggctctg gatcatctgg agactctgaa gagagagaac  4500
aagaacctgc aacaggagat ctctgacctt actgagcaga ttggagagac tggcaagagc  4560
atccatgagc tggagaaggc caagaagacc gtggagacag agaagtctga gatccagacc  4620
gctctggagg aggctgaggg cacactggag cacgaggaat ccaagattct gcgtgtgcag  4680
ctggagctga accagatcaa gggtgaggtg gacaggaaga tcgctgagaa ggacgaggag  4740
atggagcaga tcaagaggaa cagccagagg atggttgact ccatgcagag caccctggac  4800
tctgaggtca ggagcaggaa tgatgccctg agggtgaaga agaagatgga gggagacctg  4860
aacgagatgg agatccagct gagccactcc aacaggcagg ccgctgaggc ccagaaacag  4920
ctgaggaatg tccagggaca gctcaaggat gcccaattgc accttgatga tgccgtccgt  4980
gtcgcagagg acatgaagga gcaggcagcc atggtggagc gcagaaacgg tctgatggtg  5040
gctgagatcg aggagctgag agttgctctg gagcagacag agagaggccg caaagtggct  5100
gagactgagc tggtagacgc cagcgagcgt gttggactgc tgcactccca gaacaccagc  5160
cttctgaaca ccaagaagaa gctggagact gacctggtgc aggtgcaggg agaggtggat  5220
gacatcgtcc aggaggccag gaatgcagaa gagaaggcca agaaggcaat cactgatgcg  5280
gcaatgatgg ctgaggagct gaagaaggag caggacacca gctctcacct ggagagaatg  5340
aagaagaacc tggagatcac agtcaaggac ctgcagcacc gcctggatga ggctgagaat  5400
ctggccatga agggaggcaa gaaacaactc cagaaactgg aatccagggt gcgtgagctt  5460
gagactgagg tggaggctga gcagagaaga ggtgtagacg cggtaaaggg agtccgcaag  5520
tatgagcgca gagtcaagga gctcacttac cagactgagg aggataagaa gaatgttaac  5580
agacttcagg acctggtaga taagctgcag atgaaagtga aggcctacaa gaggcacgct  5640
gaggaagcgg aggaagcagc aaaccagcac atgtctaagt tcaggaaggt tcagcatgag  5700
ctggaggagg ctgaggagcg tgctgacatc gctgagactc aggtcaacaa gctcagagcc  5760
aagacccgtg actctggaaa gggaaaagaa gttgctgaa                        5799
```

```
SEQ ID NO: 70          moltype = AA  length = 1933
FEATURE                Location/Qualifiers
REGION                 1..1933
                       note = myosin heavy chain, fast skeletal muscle-like
source                 1..1933
                       mol_type = protein
                       organism = synthetic construct
SEQUENCE: 70
MSTDAEMQVY GKAAIYLRKS EKERMEAQAM PFDSKNACYV TDKVELYLKG LVTARADGKC  60
TVTALDFREG KEFKDADIYE MNPPKYDKIE DMAMMTYLNE ASVLYNLKER YAAWMIYTYS  120
GLFCATVNPY KWLPVYDEEV VNAYRGKKRV EAPPHIFSVS DNAFQFMMID KENQSVLITG  180
ESGAGKTVNT KRVIQYFATI AVSGGKKEAD PNKMQGSLED QIIAANPLLE SYGNAKTVRN  240
DNSSRFGKFI RIHFQAGKLA KADIETYLLE KSRVSFQLPD ERGYHIFFQM MTGHKPELVE  300
LALLTTNPYD FPMCSQGQIA VASINDNEEL DATDEAITIL GFTNEEKLGI YKLTGAVVHH  360
GNLKFKQKQR EEQAEPDGTE VADKIAYLLG LNSAEMLKAL CYPRVKVGNE YVTKGQTVAQ  420
VNNSVSALAK SIYERMFLWM VIRINEMLDT KNPRQFYIGV LDIAGFEIFD YNSMEQLCIN  480
FTNEKLQQFF NHTMFVLEQE EYKKEGIVWA FIDFGMDLAA CIELIEKPLG IFSILEEECM  540
FPKSSDTTFK DKLYAQHLGK TKAFEKPKPA KGKAEAHFSL VHYAGTVDYN ITGWLEKNKD  600
PLNDSVCQLY GKSGVKILAA LYPPPPPEDK AKKGGKKKGG SMQTVSSQFR ENLHKLMTNL  660
RSTHPHFVRC LIPNESKTPG LMENFLVIHQ LRCNGVLEGI RICRKGFPSR IIYADFKQRY  720
KVLNASVIPE GQFMDNKKAS EKLLGSIDVN HEDYKFGHTK VFFKAGLLGV LEEMRDEKLA  780
SLVGMLQALS RGFLMRREFT KMMERRESIY SIQYNIRSFM NVKTWPWMKL YFKIKPLLQS  840
AETEKELANM KENYEKMKTD LAKALSTKKQ MEEKLVSLTQ EKNDLALQVA SEGESLNDAE  900
ERCEGLIKSK IQQEAKLKET TERLEDEEEI NAELTAKKRK LEDECSELKK DIDDLELTLA  960
KVEKEKHATE NKVKNLTEEM ASMDESVAKL TKEKKALQEA HQQTLDDLQA EEDKVNTLTK  1020
AKTKLEQQVD DLEGSLEQEK KLRMDLERSK RKLEGDLKLA QESIMDLEND KQQADEKIKK  1080
KEFETTQLLS KVEDEQSLGA QLQKKIKELQ ARIEELEEEI EAERAARAKV EKQRADLSRE  1140
LEEISERLEE AGGATAAQIE MNKKREAEFQ KLRRDLEEST LQHEATAAAL RKKQADSVAE  1200
LGEQIDNLQR VKQKLEKEKS EYKMEIDDLS SNMEAVAKAK GNLEKMCRTL EDQLSELKTK  1260
NDENVRQVND ISGQRARLLT ENGEFGRQLE EKEALVSQLT RGKQAFTQQV EELKRAIEEE  1320
VKAKNALAHG VQSARHDCDL LREQFEEEQE AKAELQRGMS KANSEVAQWR TKYETDAIQR  1380
TEELEEAKKK LAQRLQDAEE TIEATNSKCA SLEKTKQRLQ GEVEDLMIDV ERANALAANL  1440
DKKQRNFDKV LAEWKQKYEE GQAELEGAQK EARSMSTELF KMKNSYEEAL DHLETLKREN  1500
KNLQQEISDL TEQIGETGKS IHELEKAKKT VETEKSEIQT ALEEAEGTLE HEESKILRVQ  1560
LELNQIKGEV DRKIAEKDEE MEQIKRNSQR MVDSMQSTLD SEVRSRNDAL RVKKKMEGDL  1620
NEMEIQLSHS NRQAAEAQKQ LRNVQGQLKD AQLHLDDAVR VAEDMKEQAA MVERRNGLMV  1680
AEIEELRVAL EQTERGRKVA ETELVDASER VGLLHSQNTS LLNTKKKLET DLVQVQGEVD  1740
DIVQEARNAE EKAKKAITDA AMMAEELKKE QDTSSHLERM KKNLEITVKD LQHRLDEAEN  1800
LAMKGGKKQL QKLESRVREL ETEVEAEQRR GVDAVKGVRK YERRVKELTY QTEEDKKNVN  1860
RLQDLVDKLQ MKVKAYKRHA EEAEEAANQH MSKFRKVQHE LEEAEERADI AETQVNKLRA  1920
KTRDSGKGKE VAE                                                 1933

SEQ ID NO: 71          moltype = AA  length = 7
FEATURE                Location/Qualifiers
REGION                 1..7
                       note = myosin heavy chain, fast skeletal muscle-like
                        fragment
source                 1..7
                       mol_type = protein
                       organism = synthetic construct
SEQUENCE: 71
AAIYLRK                                                        7

SEQ ID NO: 72          moltype = AA  length = 10
FEATURE                Location/Qualifiers
REGION                 1..10
                       note = myosin heavy chain, fast skeletal muscle-like
                        fragment
source                 1..10
                       mol_type = protein
                       organism = synthetic construct
SEQUENCE: 72
ADIETYLLEK                                                     10

SEQ ID NO: 73          moltype = AA  length = 19
FEATURE                Location/Qualifiers
REGION                 1..19
                       note = myosin heavy chain, fast skeletal muscle-like
                        fragment
source                 1..19
                       mol_type = protein
                       organism = synthetic construct
SEQUENCE: 73
ALQEAHQQTL DDLQAEEDK                                           19

SEQ ID NO: 74          moltype = AA  length = 11
FEATURE                Location/Qualifiers
REGION                 1..11
                       note = myosin heavy chain, fast skeletal muscle-like
```

```
                          fragment
source                   1..11
                         mol_type = protein
                         organism = synthetic construct
SEQUENCE: 74
DIDDLELTLA K                                                11

SEQ ID NO: 75            moltype = AA  length = 11
FEATURE                  Location/Qualifiers
REGION                   1..11
                         note = myosin heavy chain, fast skeletal muscle-like
                          fragment
source                   1..11
                         mol_type = protein
                         organism = synthetic construct
SEQUENCE: 75
EALVSQLTRG K                                                11

SEQ ID NO: 76            moltype = AA  length = 10
FEATURE                  Location/Qualifiers
REGION                   1..10
                         note = myosin heavy chain, fast skeletal muscle-like
                          fragment
source                   1..10
                         mol_type = protein
                         organism = synthetic construct
SEQUENCE: 76
EFETTQLLSK                                                  10

SEQ ID NO: 77            moltype = AA  length = 10
FEATURE                  Location/Qualifiers
REGION                   1..10
                         note = myosin heavy chain, fast skeletal muscle-like
                          fragment
source                   1..10
                         mol_type = protein
                         organism = synthetic construct
SEQUENCE: 77
ELTYQTEEDK                                                  10

SEQ ID NO: 78            moltype = AA  length = 15
FEATURE                  Location/Qualifiers
REGION                   1..15
                         note = myosin heavy chain, fast skeletal muscle-like
                          fragment
source                   1..15
                         mol_type = protein
                         organism = synthetic construct
SEQUENCE: 78
ENQSVLITGE SGAGK                                            15

SEQ ID NO: 79            moltype = AA  length = 19
FEATURE                  Location/Qualifiers
REGION                   1..19
                         note = myosin heavy chain, fast skeletal muscle-like
                          fragment
source                   1..19
                         mol_type = protein
                         organism = synthetic construct
SEQUENCE: 79
ETTERLEDEE EINAELTAK                                        19

SEQ ID NO: 80            moltype = AA  length = 10
FEATURE                  Location/Qualifiers
REGION                   1..10
                         note = myosin heavy chain, fast skeletal muscle-like
                          fragment
source                   1..10
                         mol_type = protein
                         organism = synthetic construct
SEQUENCE: 80
FIRIHFQAGK                                                  10

SEQ ID NO: 81            moltype = AA  length = 12
FEATURE                  Location/Qualifiers
REGION                   1..12
                         note = myosin heavy chain, fast skeletal muscle-like
                          fragment
source                   1..12
```

```
                        mol_type = protein
                        organism = synthetic construct
SEQUENCE: 81
GFPSRIIYAD FK                                                     12

SEQ ID NO: 82           moltype = AA  length = 10
FEATURE                 Location/Qualifiers
REGION                  1..10
                        note = myosin heavy chain, fast skeletal muscle-like
                         fragment
source                  1..10
                        mol_type = protein
                        organism = synthetic construct
SEQUENCE: 82
GLVTARADGK                                                        10

SEQ ID NO: 83           moltype = AA  length = 16
FEATURE                 Location/Qualifiers
REGION                  1..16
                        note = myosin heavy chain, fast skeletal muscle-like
                         fragment
source                  1..16
                        mol_type = protein
                        organism = synthetic construct
SEQUENCE: 83
GQTVAQVNNS VSALAK                                                 16

SEQ ID NO: 84           moltype = AA  length = 12
FEATURE                 Location/Qualifiers
REGION                  1..12
                        note = myosin heavy chain, fast skeletal muscle-like
                         fragment
source                  1..12
                        mol_type = protein
                        organism = synthetic construct
SEQUENCE: 84
IKPLLQSAET EK                                                     12

SEQ ID NO: 85           moltype = AA  length = 14
FEATURE                 Location/Qualifiers
REGION                  1..14
                        note = myosin heavy chain, fast skeletal muscle-like
                         fragment
source                  1..14
                        mol_type = protein
                        organism = synthetic construct
SEQUENCE: 85
ILAALYPPPP PEDK                                                   14

SEQ ID NO: 86           moltype = AA  length = 12
FEATURE                 Location/Qualifiers
REGION                  1..12
                        note = myosin heavy chain, fast skeletal muscle-like
                         fragment
source                  1..12
                        mol_type = protein
                        organism = synthetic construct
SEQUENCE: 86
ILRVQLELNQ IK                                                     12

SEQ ID NO: 87           moltype = AA  length = 18
FEATURE                 Location/Qualifiers
REGION                  1..18
                        note = myosin heavy chain, fast skeletal muscle-like
                         fragment
source                  1..18
                        mol_type = protein
                        organism = synthetic construct
SEQUENCE: 87
LAQRLQDAEE TIEATNSK                                               18

SEQ ID NO: 88           moltype = AA  length = 16
FEATURE                 Location/Qualifiers
REGION                  1..16
                        note = myosin heavy chain, fast skeletal muscle-like
                         fragment
source                  1..16
                        mol_type = protein
                        organism = synthetic construct
```

```
SEQUENCE: 88
LEQQVDDLEG SLEQEK                                                 16

SEQ ID NO: 89          moltype = AA  length = 24
FEATURE                Location/Qualifiers
REGION                 1..24
                       note = myosin heavy chain, fast skeletal muscle-like
                        fragment
source                 1..24
                       mol_type = protein
                       organism = synthetic construct
SEQUENCE: 89
LESRVRELET EVEAEQRRGV DAVK                                        24

SEQ ID NO: 90          moltype = AA  length = 13
FEATURE                Location/Qualifiers
REGION                 1..13
                       note = myosin heavy chain, fast skeletal muscle-like
                        fragment
source                 1..13
                       mol_type = protein
                       organism = synthetic construct
SEQUENCE: 90
LLGSIDVNHE DYK                                                    13

SEQ ID NO: 91          moltype = AA  length = 21
FEATURE                Location/Qualifiers
REGION                 1..21
                       note = myosin heavy chain, fast skeletal muscle-like
                        fragment
source                 1..21
                       mol_type = protein
                       organism = synthetic construct
SEQUENCE: 91
LRRDLEESTL QHEATAAALR K                                           21

SEQ ID NO: 92          moltype = AA  length = 12
FEATURE                Location/Qualifiers
REGION                 1..12
                       note = myosin heavy chain, fast skeletal muscle-like
                        fragment
source                 1..12
                       mol_type = protein
                       organism = synthetic construct
SEQUENCE: 92
LTGAVVHHGN LK                                                     12

SEQ ID NO: 93          moltype = AA  length = 32
FEATURE                Location/Qualifiers
REGION                 1..32
                       note = myosin heavy chain, fast skeletal muscle-like
                        fragment
source                 1..32
                       mol_type = protein
                       organism = synthetic construct
SEQUENCE: 93
NDENVRQVND ISGQRARLLT ENGEFGRQLE EK                               32

SEQ ID NO: 94          moltype = AA  length = 7
FEATURE                Location/Qualifiers
REGION                 1..7
                       note = myosin heavy chain, fast skeletal muscle-like
                        fragment
source                 1..7
                       mol_type = protein
                       organism = synthetic construct
SEQUENCE: 94
NLEITVK                                                           7

SEQ ID NO: 95          moltype = AA  length = 18
FEATURE                Location/Qualifiers
REGION                 1..18
                       note = myosin heavy chain, fast skeletal muscle-like
                        fragment
source                 1..18
                       mol_type = protein
                       organism = synthetic construct
SEQUENCE: 95
NLQQEISDLT EQIGETGK                                               18
```

-continued

```
SEQ ID NO: 96          moltype = AA  length = 14
FEATURE                Location/Qualifiers
REGION                 1..14
                       note = myosin heavy chain, fast skeletal muscle-like
                        fragment
source                 1..14
                       mol_type = protein
                       organism = synthetic construct
SEQUENCE: 96
NSYEEALDHL ETLK                                                    14

SEQ ID NO: 97          moltype = AA  length = 19
FEATURE                Location/Qualifiers
REGION                 1..19
                       note = myosin heavy chain, fast skeletal muscle-like
                        fragment
source                 1..19
                       mol_type = protein
                       organism = synthetic construct
SEQUENCE: 97
QADSVAELGE QIDNLQRVK                                               19

SEQ ID NO: 98          moltype = AA  length = 11
FEATURE                Location/Qualifiers
REGION                 1..11
                       note = myosin heavy chain, fast skeletal muscle-like
                        fragment
source                 1..11
                       mol_type = protein
                       organism = synthetic construct
SEQUENCE: 98
QAFTQQVEEL K                                                       11

SEQ ID NO: 99          moltype = AA  length = 16
FEATURE                Location/Qualifiers
REGION                 1..16
                       note = myosin heavy chain, fast skeletal muscle-like
                        fragment
source                 1..16
                       mol_type = protein
                       organism = synthetic construct
SEQUENCE: 99
QREEQAEPDG TEVADK                                                  16

SEQ ID NO: 100         moltype = AA  length = 8
FEATURE                Location/Qualifiers
REGION                 1..8
                       note = myosin heavy chain, fast skeletal muscle-like
                        fragment
source                 1..8
                       mol_type = protein
                       organism = synthetic construct
SEQUENCE: 100
RAIEEEVK                                                           8

SEQ ID NO: 101         moltype = AA  length = 20
FEATURE                Location/Qualifiers
REGION                 1..20
                       note = myosin heavy chain, fast skeletal muscle-like
                        fragment
source                 1..20
                       mol_type = protein
                       organism = synthetic construct
SEQUENCE: 101
SEIQTALEEA EGTLEHEESK                                              20

SEQ ID NO: 102         moltype = AA  length = 12
FEATURE                Location/Qualifiers
REGION                 1..12
                       note = myosin heavy chain, fast skeletal muscle-like
                        fragment
source                 1..12
                       mol_type = protein
                       organism = synthetic construct
SEQUENCE: 102
TVRNDNSSRF GK                                                      12

SEQ ID NO: 103         moltype = AA  length = 27
```

```
FEATURE                 Location/Qualifiers
REGION                  1..27
                        note = myosin heavy chain, fast skeletal muscle-like
                         fragment
source                  1..27
                        mol_type = protein
                        organism = synthetic construct
SEQUENCE: 103
VAETELVDAS ERVGLLHSQN TSLLNTK                                      27

SEQ ID NO: 104          moltype = AA  length = 13
FEATURE                 Location/Qualifiers
REGION                  1..13
                        note = myosin heavy chain, fast skeletal muscle-like
                         fragment
source                  1..13
                        mol_type = protein
                        organism = synthetic construct
SEQUENCE: 104
VEDEQSLGAQ LQK                                                     13

SEQ ID NO: 105          moltype = AA  length = 8
FEATURE                 Location/Qualifiers
REGION                  1..8
                        note = myosin heavy chain, fast skeletal muscle-like
                         fragment
source                  1..8
                        mol_type = protein
                        organism = synthetic construct
SEQUENCE: 105
VGNEYVTK                                                           8

SEQ ID NO: 106          moltype = AA  length = 21
FEATURE                 Location/Qualifiers
REGION                  1..21
                        note = myosin heavy chain, fast skeletal muscle-like
                         fragment
source                  1..21
                        mol_type = protein
                        organism = synthetic construct
SEQUENCE: 106
VQHELEEAEE RADIAETQVN K                                            21

SEQ ID NO: 107          moltype = AA  length = 13
FEATURE                 Location/Qualifiers
REGION                  1..13
                        note = myosin heavy chain, fast skeletal muscle-like
                         fragment
source                  1..13
                        mol_type = protein
                        organism = synthetic construct
SEQUENCE: 107
YEEGQAELEG AQK                                                     13

SEQ ID NO: 108          moltype = AA  length = 16
FEATURE                 Location/Qualifiers
REGION                  1..16
                        note = myosin heavy chain, fast skeletal muscle-like
                         fragment
source                  1..16
                        mol_type = protein
                        organism = synthetic construct
SEQUENCE: 108
YETDAIQRTE ELEEAK                                                  16

SEQ ID NO: 109          moltype = DNA  length = 2532
FEATURE                 Location/Qualifiers
misc_feature            1..2532
                        note = glycogen phosphorylase, muscle form-like
source                  1..2532
                        mol_type = other DNA
                        organism = synthetic construct
SEQUENCE: 109
atgtcaaaac cattgtcaga ccacgataaa aggaagcaga tctccgtgag aggtcttgct  60
ggtgtggaaa atgtcgcaga actgaaggtc gctttcaaca ggcatctcca ttttacactg  120
gtcaaggaca gaaatgtggc aaacaaacgg gattactact ttgctctcgc caacaccgtg  180
cgtgaccact tggtgggcag gtggatcaga acccagcagt actactatga gaaagatccc  240
aaacgtgtgt actacatctc cctggagttt tatatgggtc gcaccctgca gaacactatg  300
gtgaacctgg ccctggagaa cgcttgtgat gaggccatat accagctggg tctggacatg  360
```

```
gaggagctgg aggacatgga agaggatgct ggcctgggaa acggtggtct tggccgtctt  420
gccgcatgct tcctggactc aatggcttct ctaggccttg ctgcctatgg ctatggtatc  480
cgctatgagt ttggcatctt caatcagaag atcgtcaatg gctggcaggt tgaggaggcc  540
gatgattggt tgcgttacgg caacccctgg gagaaggccc gccctgagta catgcgcccc  600
gtcaagttct atggcaggac cgagcacacc ccagatggtg tgaaatgggt tgacactcag  660
gtagtgttgg ctctgccata tgacacccct attcccggct acagaaacaa cattgtcaac  720
accatgagac tgtggtctgc taaggcccca tgcgacttca acctgaaaga cttcaacgtt  780
ggtggctaca ttcaggctgt gttggacaga aacttgtgtg agaacatttc ccgcgtgctg  840
taccccaatg ataatttctt tgagggcaag gagctgcgtc tgaagcagga gtactttgtg  900
gtggccgcca ctctgcagga cgtcgtccgt cgtttcaagg cctctaagtt tggctccaga  960
gagattgtcc gcacagactt cgccgagcta ccaaacaaag ttgccatcca gctgaatgac  1020
actcaccctg ccatggctat tcctgagctg atgagggtcc tggttgatga ggagaagctg  1080
ggttgggaca aggcctggga cgtgtgtgtc cgtacctgtg cctacacaaa ccacaccgtg  1140
ctgcctgagg ccctggagcg ctggcccatt gacctgttcc atcacctgct gccacgtcac  1200
ctggagatca tctacgagat caaccgtcgc ttcatggagt atgttgcctc gaagttccct  1260
ggagacaacg accgtctgcg tcgcatgtcc ctgattgagg agggaggatg caagaaagtc  1320
aacatggctc atctgtgtat cgttggttcc catgctgtca acggcgtggc ccgcatccac  1380
tctgagatcc tcatcgccac tctgttcaag gacttctatg agttggaccc acacaagttt  1440
cagaacaaga ccaatgggat caccccccgt cgctggctgg ttatgtgcaa ccccggcttg  1500
gcggaggtca tcgcagagaa aattggagag gagtttatcc gtgaccttga ccagcttaag  1560
cgactgttga agttcgttaa tgatgatgct ttcatccgtg acatcgccaa agtcaagcag  1620
gagaacaagc tgaagttcgc tgtgcacctg gaagagcact acaaggtcaa gatcaacccc  1680
cagtccatgt ttgacttcca agtcaaaaga atccacgagt acaaaagaca gctgctcaac  1740
tgtctgcaca tgatcaccta ctacaaccgt atcaagaagg agcccaacaa gcactggacc  1800
ccaagaacca tcatggtcgg aggaaaggct gcaccaggct accacacagc caagatgatc  1860
atccgtctca tcacagctat cggtgaggtt gtcaaccacg accccgttgt cggcgaccgc  1920
ctcaaagtta tcttcctgga gaactacaga gtcaccctgg ctgagaaagc catcccctct  1980
gccgacctgt ctgagcagat ctctacagct ggcaccgagg cctctggcac tggtaacatg  2040
aagttcatgc tgaacggtgc tcttaccatt ggcaccatgg atggagccaa tgtggagatg  2100
gccgaggagg ccggagagga aaacttcttc atcttcggta tgagagtgga ggatgtggac  2160
gcaatggacg ccggcaaagg ataccacgcc tctgagtact acaaccgtat tcccgagctg  2220
aagcaggcca tggaccagat tgctggcggc ttcttcagtc ccaagcagcc tgacctcttc  2280
aaggaacttg tggacctgct gatgcaccat gacaggttca aggtgtttgc tgactacgaa  2340
gcctacatca aatgccagga caaggtcaac caactgtaca agaatcccaa ggaatggacc  2400
aagatggtga tccataacat tgcgggctgt ggtaaattct ccagcgaccg caccattgcc  2460
cagtacgccc gagagatctg gggcatggag cccagcctgg agaagatccc tgcccccgat  2520
gagaaactca aa                                                      2532
```

```
SEQ ID NO: 110          moltype = AA  length = 844
FEATURE                 Location/Qualifiers
REGION                  1..844
                        note = glycogen phosphorylase, muscle form-like
source                  1..844
                        mol_type = protein
                        organism = synthetic construct
SEQUENCE: 110
MSKPLSDHDK RKQISVRGLA GVENVAELKV AFNRHLHFTL VKDRNVANKR DYYFALANTV  60
RDHLVGRWIR TQQYYYEKDP KRVYYISLEF YMGRTLQNTM VNLALENACD EAIYQLGLDM  120
EELEDMEEDA GLGNGGLGRL AACFLDSMAS LGLAAYGYGI RYEFGIFNQK IVNGWQVEEA  180
DDWLRYGNPW EKARPEYMRP VKFYGRTEHT PDGVKWVDTQ VVLALPYDTP IPGYRNNIVN  240
TMRLWSAKAP CDFNLKDFNV GGYIQAVLDR NLCENISRVL YPNDNFFEGK ELRLKQEYFV  300
VAATLQDVVR RFKASKFGSR EIVRTDFAEL PNKVAIQLND THPAMAIPEL MRVLVDEEKL  360
GWDKAWDVCV RTCAYTNHTV LPEALERWPI DLFHHLLPRH LEIIYEINRR FMEYVASKFP  420
GDNDRLRRMS LIEEGGCKKV NMAHLCIVGS HAVNGVARIH SEILIATLFK DFYELDPHKF  480
QNKTNGITPR RWLVMCNPGL AEVIAEKIGE EFIRDLDQLK RLLKFVNDDA FIRDIAKVKQ  540
ENKLKFAVHL EEHYKVKINP QSMFDFQVKR IHEYKRQLLN CLHMITYYNR IKKEPNKHWT  600
PRTIMVGGKA APGYHTAKMI IRLITAIGEV VNHDPVVGDR LKVIFLENYR VTLAEKAIPS  660
ADLSEQISTA GTEASGTGNM KFMLNGALTI GTMDGANVEM AEEAGEENFF IFGMRVEDVD  720
AMDAGKGYHA SEYYNRIPEL KQAMDQIAGG FFSPKQPDLF KELVDLLMHH DRFKVFADYE  780
AYIKCQDKVN QLYKNPKEWT KMVIHNIAGC GKFSSDRTIA QYAREIWGME PSLEKIPAPD  840
EKLK                                                               844
```

```
SEQ ID NO: 111          moltype = AA  length = 9
FEATURE                 Location/Qualifiers
REGION                  1..9
                        note = glycogen phosphorylase, muscle form-like fragment
source                  1..9
                        mol_type = protein
                        organism = synthetic construct
SEQUENCE: 111
DFYELDPHK                                                          9
```

```
SEQ ID NO: 112          moltype = AA  length = 10
FEATURE                 Location/Qualifiers
REGION                  1..10
                        note = glycogen phosphorylase, muscle form-like fragment
source                  1..10
                        mol_type = protein
                        organism = synthetic construct
```

```
SEQUENCE: 112
FAVHLEEHYK                                                  10

SEQ ID NO: 113          moltype = AA  length = 13
FEATURE                 Location/Qualifiers
REGION                  1..13
                        note = glycogen phosphorylase, muscle form-like fragment
source                  1..13
                        mol_type = protein
                        organism = synthetic construct
SEQUENCE: 113
FYGRTEHTPD GVK                                              13

SEQ ID NO: 114          moltype = AA  length = 15
FEATURE                 Location/Qualifiers
REGION                  1..15
                        note = glycogen phosphorylase, muscle form-like fragment
source                  1..15
                        mol_type = protein
                        organism = synthetic construct
SEQUENCE: 114
GYHASEYYNR IPELK                                            15

SEQ ID NO: 115          moltype = AA  length = 13
FEATURE                 Location/Qualifiers
REGION                  1..13
                        note = glycogen phosphorylase, muscle form-like fragment
source                  1..13
                        mol_type = protein
                        organism = synthetic construct
SEQUENCE: 115
IGEEFIRDLD QLK                                              13

SEQ ID NO: 116          moltype = AA  length = 14
FEATURE                 Location/Qualifiers
REGION                  1..14
                        note = glycogen phosphorylase, muscle form-like fragment
source                  1..14
                        mol_type = protein
                        organism = synthetic construct
SEQUENCE: 116
QAMDQIAGGF FSPK                                             14

SEQ ID NO: 117          moltype = AA  length = 17
FEATURE                 Location/Qualifiers
REGION                  1..17
                        note = glycogen phosphorylase, muscle form-like fragment
source                  1..17
                        mol_type = protein
                        organism = synthetic construct
SEQUENCE: 117
QISVRGLAGV ENVAELK                                          17

SEQ ID NO: 118          moltype = AA  length = 10
FEATURE                 Location/Qualifiers
REGION                  1..10
                        note = glycogen phosphorylase, muscle form-like fragment
source                  1..10
                        mol_type = protein
                        organism = synthetic construct
SEQUENCE: 118
VFADYEAYIK                                                  10

SEQ ID NO: 119          moltype = AA  length = 14
FEATURE                 Location/Qualifiers
REGION                  1..14
                        note = glycogen phosphorylase, muscle form-like fragment
source                  1..14
                        mol_type = protein
                        organism = synthetic construct
SEQUENCE: 119
VIFLENYRVT LAEK                                             14

SEQ ID NO: 120          moltype = DNA  length = 3399
FEATURE                 Location/Qualifiers
misc_feature            1..3399
                        note = myosin-binding protein C, fast-type-like
source                  1..3399
                        mol_type = other DNA
```

organism = synthetic construct
SEQUENCE: 120
atgcctgaag ccgctgatgc agtgaagccg gagggcgagg agggagaagc accagcagaa 60
gccgaagaaa atactgcaga agatgatgag ccactgcctg aaggagagga gggtgcccat 120
cagtcacagg agattacagg actgtttctt cagcaccctg agactacggt tgccataaca 180
ggtacggaca ttgtgtttac tgccaaagtg gactctacta cactatcaag gaaacccacc 240
attaaatggc tgaaggggaa gtggctggac ctgggcagca aagcaggaaa acacatgcag 300
ttcaaagaga cttttgacag agccacaaag atctacacct gggacatgaa gataatcaag 360
gtggtccctg gtgacgctgg ggcctacagg tgtgaggtca cctccaaaga caagtgtgac 420
agcagcgctt tcgacatctc cgtggaggct gtgcaaattg aggaggaaca tgattctttg 480
gccgcattca aaagaacgga tgctggagag gatgaaggca gtttggattt cagtgctttg 540
ctgaaagcta ccaagaagaa gaagaagcca gtcgtagatg aggagaaggc agacgtgtgg 600
gaaatcctga agaacgctca acccagcgag tatgagaaga ttgcttttga gtacggcatt 660
acagacctga ggggtctgct caagcgactg aagaagatga agactgttga gcccaagcac 720
agcgacgctt tcctaaagag aatggagtct gcctactctg tggataaggg caagaaaatc 780
gtactgcagg tggaagtggt tgacccaaat gcccaggtca aatggttgaa gaacggtcag 840
gagataaaat catcagccaa gtacatcata gaatcagttg gcaacatcag gacgctcacc 900
atcaacaagt gtagcctggc tgacgacgct gcgtacgagt gtgtgattgg ggaagagaag 960
tccttcacag aggtgtttgt caaagagccc ccggtcacca tcaccaagct gctggatgat 1020
taccacgtgg tggtgggaga gagagtggag tttgaggtgg aggtgtctgt ggagggagca 1080
cacgttaact ggatgtttga ggaccaagaa ctctccaggg acacccataa gtaccgcttt 1140
aagaaggacg ggttgaagca catgctcatc atccaagagg ctacgctgga tgacattgga 1200
atgtactggt gcttcaccaa cggcgggcga accaaaggag agctagaagt tgaagagaaa 1260
gaactggagg tgttgcagaa catcgctgac ctgacggtga aggccgagga ccaggccatg 1320
ttcaagtgtg aggtgtctga tgagaaggta acagggaaat ggctcaaaga tggcgtggag 1380
gtgctgccca gcagtcgcat caagctgacc cacatcggaa gaatccatcg gcttaccata 1440
gacgacgtca agcccgagga cgctggagac tatacctta tcccagacgg atatgccctc 1500
tcactgtccg ccaaactcaa cttcctggaa attaagatcg actatgtccc ccgccaagag 1560
ccacccaaga tccatctaga caccaccggc aacatggttt cccagaacac catcattgtg 1620
gtggctggca acaagctgcg cctggacgtg gagatctctg gagagcctcc tcccactgtc 1680
gtctgggcaa agggagacac ggcaatcaca gctgtggagg ggcgtgtgag gactgagagc 1740
cggaaggacc tgagctgctt cgtcatagag ggggcagaga gagaggatga gggcaactac 1800
accatcattg tcaccaaccc tgccggagag gacaaggctc atctgtttgt caagattgtt 1860
gatgtgcctg actgccctga gaatgtaaag tgtacctcgg tgggagaaga ctgtgccacc 1920
atggtctggg acccacccaa gttcgacgga ggcgcaccag tcacaggcta tctcatggag 1980
aggaagaaga agggctccac caggtggacg aagctcaact ttgacgtgta cgagggggtg 2040
acgtacgaag ccaagaggat gattgagggc gtgctctacg agatgagagt gtacgccgtc 2100
aatggcattg gcatgtccca gcccagcctc aattccaaac ccttcatgcc catcgctgca 2160
accagtgagc ctctgggcct caaggtgcat gatgtcacag acaccacatg taccctgaag 2220
tggctggccc ctgagaagat cggtgccgga ggcctggacg gatacgttat tgagtactgc 2280
aaggagggag acacggagtg ggtggtggcg aacactgagc tggtggagag acagaattac 2340
acagtccgca acctccccac cgcggagaag atcaacttca gagtggtggc cgtgaacatt 2400
gctggacgca gcccccctac cggcctgagc cagcccgtca ctatccgcga gatcgtggaa 2460
ctgcccaaga tccgcctccc tcgctacttg agacagaagt acattagaag agtgggcgac 2520
aaaatcaacc tgaccatccc cttccagggt aagccacgtc ccaaagtgca atggtacaag 2580
gatggggaag agcttgacac tcgagttgcc agcatacgca attccgaagt ggactctatc 2640
ctgttcatcc gctcggctga gagatcccac tctgggaagt acgagttggt cctgcagatt 2700
gagaacatgg aggccagggc tattctggaa atcaggatcg tagaggcacc tgggcctccc 2760
gaggtagtga aggtcacaga cgtttggggc ttcaacgctg cgctggagtg gaagccaccg 2820
aaggacgacg gcaactgcga gatcaccggt tacacaatac agaaggcgga caagaagaca 2880
aatgaatggt tcactatcta cgagcacaac aggaggacaa actgcacagc ctcagacctg 2940
atcatgggaa atgagtacat gttccgtgtc ttcagcgaga acctcgttgg aaagagtgag 3000
gatttctgcc tcagcaagga cacagccatc atacctaaga taggattgga gtacaaccca 3060
cctccattca aggagaagga tatgcaaagc gcccccaagt tcatacagcc cctgcttgac 3120
aggtctgtgg tggcaggcta cagtaccacc atcagctctg ctgtcaagac ttgtcctaaa 3180
cctaagatca ggtggttgag gaataagatt cccctggacg agaaccctag gttcctgatg 3240
cagaacaacc aggggttttt gaccctgaac atccgcaagc ccagtcagta tgacgggggc 3300
aagttcacct gcaaggctat caactctttg gggaggacg tcgtggagtg caccctactc 3360
gtacgagctc tcaaggacaa ggaagatgga gacgagaaa 3399

SEQ ID NO: 121 moltype = AA length = 1133
FEATURE Location/Qualifiers
REGION 1..1133
note = myosin-binding protein C, fast-type-like
source 1..1133
mol_type = protein
organism = synthetic construct
SEQUENCE: 121
MPEAADAVKP EGEEGEAPAE AEENTAEDDE PLPEGEEGAH QSQEITGLFL QHPETTVAIT 60
GTDIVFTAKV DSTTLSRKPT IKWLKGKWLD LGSKAGKHMQ FKETFDRATK IYTWDMKIIK 120
VVPGDAGAYR CEVTSKDKCD SSAFDISVEA VQIEEEHDSL AAFKRTDAGE DEGSLDFSAL 180
LKATKKKKKP VVDEEKADVW EILKNAQPSE YEKIAFEYGI TDLRGLLKRL KKMKTVEPKH 240
SDAFLKRMES AYSVDKGKKI VLQVEVVDPN AQVKWLKNGQ EIKSSAKYII ESVGNIRTLT 300
INKCSLADDA AYECVIGEEK SFTEVFVKEP PVTITKLLDD YHVVVGERVE FEVEVSVEGA 360
HVNWMFEDQE LSRDTHKYRF KKDGLKHMLI IQEATLDDIG MYWCFTNGGR TKGELEVEEK 420
ELEVLQNIAD LTVKAEDQAM FKCEVSDEKV TGKWLKDGVE VLPSSRIKLT HIGRIHRLTI 480
DDVKPEDAGD YTFIPDGYAL SLSAKLNFLE IKIDYVPRQE PPKIHLDTTG NMVSQNTIIV 540
VAGNKLRLDV EISGEPPPTV VWAKGDTAIT AVEGRVRTES RKDLSCFVIE GAEREDEGNY 600
TIIVTNPAGE DKAHLFVKIV DVPDCPENVK CTSVGEDCAT MVWDPPKFDG GAPVTGYLME 660

```
RKKKGSTRWT KLNFDVYEGV TYEAKRMIEG VLYEMRVYAV NGIGMSQPSL NSKPFMPIAA  720
TSEPLGLKVH DVTDTTCTLK WLAPEKIGAG GLDGYVIEYC KEGDTEWVVA NTELVERQNY  780
TVRNLPTAEK INFRVVAVNI AGRSPPTGLS QPVTIREIVE LPKIRLPRYL RQKYIRRVGD  840
KINLTIPFQG KPRPKVQWYK DGEELDTRVA SIRNSEVDSI LFIRSAERSH SGKYELVLQI  900
ENMEARAILE IRIVEAPGPP EVVKVTDVWG FNAALEWKPP KDDGNCEITG YTIQKADKKT  960
NEWFTIYEHN RRTNCTASDL IMGNEYMFRV FSENLVGKSE DFCLSKDTAI IPKIGLEYNP  1020
PPFKEKDMQS APKFIQPLLD RSVVAGYSTT ISSAVKTCPK PKIRWLRNKI PLDENPRFLM  1080
QNNQGVLTLN IRKPSQYDGG KFTCKAINSL GEDVVECTLL VRALKDKEDG DEK         1133

SEQ ID NO: 122         moltype = AA  length = 8
FEATURE                Location/Qualifiers
REGION                 1..8
                       note = myosin-binding protein C, fast-type-like fragment
source                 1..8
                       mol_type = protein
                       organism = synthetic construct
SEQUENCE: 122
ADVWEILK                                                           8

SEQ ID NO: 123         moltype = AA  length = 14
FEATURE                Location/Qualifiers
REGION                 1..14
                       note = myosin-binding protein C, fast-type-like fragment
source                 1..14
                       mol_type = protein
                       organism = synthetic construct
SEQUENCE: 123
ELEVLQNIAD LTVK                                                    14

SEQ ID NO: 124         moltype = AA  length = 8
FEATURE                Location/Qualifiers
REGION                 1..8
                       note = myosin-binding protein C, fast-type-like fragment
source                 1..8
                       mol_type = protein
                       organism = synthetic construct
SEQUENCE: 124
EPPVTITK                                                           8

SEQ ID NO: 125         moltype = AA  length = 8
FEATURE                Location/Qualifiers
REGION                 1..8
                       note = myosin-binding protein C, fast-type-like fragment
source                 1..8
                       mol_type = protein
                       organism = synthetic construct
SEQUENCE: 125
GELEVEEK                                                           8

SEQ ID NO: 126         moltype = AA  length = 7
FEATURE                Location/Qualifiers
REGION                 1..7
                       note = myosin-binding protein C, fast-type-like fragment
source                 1..7
                       mol_type = protein
                       organism = synthetic construct
SEQUENCE: 126
HSDAFLK                                                            7

SEQ ID NO: 127         moltype = AA  length = 15
FEATURE                Location/Qualifiers
REGION                 1..15
                       note = myosin-binding protein C, fast-type-like fragment
source                 1..15
                       mol_type = protein
                       organism = synthetic construct
SEQUENCE: 127
IAFEYGITDL RGLLK                                                   15

SEQ ID NO: 128         moltype = AA  length = 11
FEATURE                Location/Qualifiers
REGION                 1..11
                       note = myosin-binding protein C, fast-type-like fragment
source                 1..11
                       mol_type = protein
                       organism = synthetic construct
SEQUENCE: 128
IGLEYNPPPF K                                                       11
```

```
SEQ ID NO: 129          moltype = AA  length = 14
FEATURE                 Location/Qualifiers
REGION                  1..14
                        note = myosin-binding protein C, fast-type-like fragment
source                  1..14
                        mol_type = protein
                        organism = synthetic construct
SEQUENCE: 129
INLTIPFQGK PRPK                                                           14

SEQ ID NO: 130          moltype = AA  length = 15
FEATURE                 Location/Qualifiers
REGION                  1..15
                        note = myosin-binding protein C, fast-type-like fragment
source                  1..15
                        mol_type = protein
                        organism = synthetic construct
SEQUENCE: 130
IVLQVEVVDP NAQVK                                                          15

SEQ ID NO: 131          moltype = AA  length = 14
FEATURE                 Location/Qualifiers
REGION                  1..14
                        note = myosin-binding protein C, fast-type-like fragment
source                  1..14
                        mol_type = protein
                        organism = synthetic construct
SEQUENCE: 131
LNFDVYEGVT YEAK                                                           14

SEQ ID NO: 132          moltype = AA  length = 7
FEATURE                 Location/Qualifiers
REGION                  1..7
                        note = myosin-binding protein C, fast-type-like fragment
source                  1..7
                        mol_type = protein
                        organism = synthetic construct
SEQUENCE: 132
LNFLEIK                                                                   7

SEQ ID NO: 133          moltype = AA  length = 9
FEATURE                 Location/Qualifiers
REGION                  1..9
                        note = myosin-binding protein C, fast-type-like fragment
source                  1..9
                        mol_type = protein
                        organism = synthetic construct
SEQUENCE: 133
NAQPSEYEK                                                                 9

SEQ ID NO: 134          moltype = AA  length = 18
FEATURE                 Location/Qualifiers
REGION                  1..18
                        note = myosin-binding protein C, fast-type-like fragment
source                  1..18
                        mol_type = protein
                        organism = synthetic construct
SEQUENCE: 134
RTDAGEDEGS LDFSALLK                                                       18

SEQ ID NO: 135          moltype = AA  length = 8
FEATURE                 Location/Qualifiers
REGION                  1..8
                        note = myosin-binding protein C, fast-type-like fragment
source                  1..8
                        mol_type = protein
                        organism = synthetic construct
SEQUENCE: 135
SFTEVFVK                                                                  8

SEQ ID NO: 136          moltype = AA  length = 13
FEATURE                 Location/Qualifiers
REGION                  1..13
                        note = myosin-binding protein C, fast-type-like fragment
source                  1..13
                        mol_type = protein
                        organism = synthetic construct
SEQUENCE: 136
VDSTTLSRKP TIK                                                            13
```

```
SEQ ID NO: 137          moltype = DNA  length = 1551
FEATURE                 Location/Qualifiers
misc_feature            1..1551
                        note = ATP synthase subunit beta, mitochondrial
source                  1..1551
                        mol_type = other DNA
                        organism = synthetic construct
SEQUENCE: 137
atgttaggag ctgtgggacg ctgctgcacc ggggctctcc aggcacttaa gcctggggtc  60
cagcccctga aggcccttgt aggatcgcca tctgtccttg gacgcagaga ctactctgca  120
cctgctgctg ctgccgcctt cgcccatggc aggatcgtag cggtcatcgg tgccgtcgtc  180
gacgtccagt tcgatgaggg cctcccaccc atcctcaatg ccctggaagt tgctgggcgt  240
gagtccaggc tagttctgga ggtggcacag catcttggtg agaacactgt gcgtaccatt  300
gccatggatg gtactgaagg tcttgtccgt ggacagaagg ttgtggacac tggcgatccc  360
atcagaatcc cagtgggtcc cgagacccta ggcagaatca tgaatgtcat tggagagccc  420
attgatgaga gggggccaat ctccaccaag cagactgccg ccatccacgc tgaggcccca  480
gagttcactg acatgagtgt ggagcaggag atcctggtaa ctggcatcaa ggtggtagat  540
ctgctggctc cctatgccaa gggaggcaaa atcggtctgt tcggtggtgc tggtgtgggc  600
aagactgtgt tgatcatgga gctgatcaac aatgtggcca aggcccatgg tggttactct  660
gtgtttgccg gagtgggaga gcgtacccgc gagggaaatg acttgtacca cgagatgatt  720
gagtcgggtg tcatcaacct gaaggatgac acctccaagg tggcgctggt gtacggacaa  780
atgaacgagc ccccaggcgc ccgtgcccgt gtggctctga ctggtctgac cgtggcagag  840
tatttccgtg accaggaggg tcaggatgtg ctgctcttca tcgataacat cttccgtttc  900
acccaggctg gctccgaggt gtctgccctg ctgggtcgta tcccctccgc tgtgggttac  960
cagcccaccc tggccactga catgggtacc atgcaggaga gaatcaccac caccaagaag  1020
ggttccatca cctctgtgca ggccatctat gtgccggctg acgatttgac tgatcccgcc  1080
cctgccacca ccttcgctca cttggacgcc accactgtgc tgtcccgtgc aatcgctgag  1140
ctgggtatct accctgctgt ggatcccctg gattccacct cccgtatcat ggaccccaac  1200
attgtcggcg ctgagcacta tgatgttgct cgtggcgtgc agaagatcct ccaggactac  1260
aagtccctgc aggatatcat tgccatcctg ggtatggatg agttgtctga ggaggacaag  1320
ctgattgtct ctcgcgcccg caagatccag cgtttcctgt cccagccctt ccaggtggcg  1380
gaggtattca ccggtcatgc tggcaagctg gtgccactca aggagaccat cagtggcttc  1440
cagagcattc taaatggtga gtacgatgcc ctgcccgagc aggctttcta catggttgga  1500
cccatcgagg aggtggttga gaaggctgca cagatggcca aggatctcgc a           1551

SEQ ID NO: 138          moltype = AA  length = 517
FEATURE                 Location/Qualifiers
REGION                  1..517
                        note = ATP synthase subunit beta, mitochondrial
source                  1..517
                        mol_type = protein
                        organism = synthetic construct
SEQUENCE: 138
MLGAVGRCCT GALQALKPGV QPLKALVGSP SVLGRRDYSA PAAAAAFAHG RIVAVIGAVV  60
DVQFDEGLPP ILNALEVAGR ESRLVLEVAQ HLGENTVRTI AMDGTEGLVR GQKVVDTGDP  120
IRIPVGPETL GRIMNVIGEP IDERGPISTK QTAAIHAEAP EFTDMSVEQE ILVTGIKVVD  180
LLAPYAKGGK IGLFGGAGVG KTVLIMELIN NVAKAHGGYS VFAGVGERTR EGNDLYHEMI  240
ESGVINLKDD TSKVALVYGQ MNEPPGARAR VALTGLTVAE YFRDQEGQDV LLFIDNIFRF  300
TQAGSEVSAL LGRIPSAVGY QPTLATDMGT MQERITTTKK GSITSVQAIY VPADDLTDPA  360
PATTFAHLDA TTVLSRAIAE LGIYPAVDPL DSTSRIMDPN IVGAEHYDVA RGVQKILQDY  420
KSLQDIIAIL GMDELSEEDK LIVSRARKIQ RFLSQPFQVA EVFTGHAGKL VPLKETISGF  480
QSILNGEYDA LPEQAFYMVG PIEEVVEKAA QMAKDLA                          517

SEQ ID NO: 139          moltype = AA  length = 11
FEATURE                 Location/Qualifiers
REGION                  1..11
                        note = ATP synthase subunit beta, mitochondrial fragment
source                  1..11
                        mol_type = protein
                        organism = synthetic construct
SEQUENCE: 139
IGLFGGAGVG K                                                      11

SEQ ID NO: 140          moltype = AA  length = 21
FEATURE                 Location/Qualifiers
REGION                  1..21
                        note = ATP synthase subunit beta, mitochondrial fragment
source                  1..21
                        mol_type = protein
                        organism = synthetic construct
SEQUENCE: 140
IQRFLSQPFQ VAEVFTGHAG K                                           21

SEQ ID NO: 141          moltype = AA  length = 13
FEATURE                 Location/Qualifiers
REGION                  1..13
                        note = ATP synthase subunit beta, mitochondrial fragment
source                  1..13
```

```
                        mol_type = protein
                        organism = synthetic construct
SEQUENCE: 141
TVLIMELINN VAK                                                      13

SEQ ID NO: 142          moltype = AA  length = 10
FEATURE                 Location/Qualifiers
REGION                  1..10
                        note = ATP synthase subunit beta, mitochondrial fragment
source                  1..10
                        mol_type = protein
                        organism = synthetic construct
SEQUENCE: 142
VVDLLAPYAK                                                          10

SEQ ID NO: 143          moltype = DNA  length = 996
FEATURE                 Location/Qualifiers
misc_feature            1..996
                        note = L-lactate dehydrogenase A chain-like
source                  1..996
                        mol_type = other DNA
                        organism = synthetic construct
SEQUENCE: 143
atgactacca aggagaagct gatcacccat gtgttggctg gtgagcctgt tggctcccgg  60
agcaaggtga cagttgttgg cgtcggcatg gttggcatgg cctccgcagt cagcgtcctg  120
ctcaaggacc tgtgcgatga gctgtgcctg attgacgtga tggaagataa actgaagggt  180
gaggtcatgg acctgcagca tggcagcctc ttctgcaaga ctcacaagat tgtgggcgac  240
aaggactaca gtacgactgc ccactccaag gtggtggtgg tcacagccgg tgctcgtcag  300
caagagggtg agagccgtct gaacctggtg cagcgtaacg tcaacatctt caaattcata  360
attccccaga tcgtcaagta cagccccaac gccatcctgc tggtcgtctc caatcctgtt  420
gacatcctaa cctacgtggc ttggaagctg agtggtttcc cccgtcaccg cgtcatcggt  480
tccggcacca acctggactc tggtcgtttc cgccacctga tgggcgagaa gctacacctt  540
cacccatcca gctgtcacgg ctggatcatt ggagaacacg gagactccag cgtgcccgta  600
tggagcggtg tgaatgttgc cggtgtttcc ctgaagggcc tgaacccaga catgggcaca  660
gacgcagaca aggaggactg gaagcacgtc cacaagatgg tggtcgacgg tgcctatgag  720
gtcatcaagc tgaagggtta cacctcctgg gctatcggca tgtccgtcgc tgacctggtt  780
gagagcatcc tgaagaacct ccacaaagtc caccctgtgt ccaccctggt caagggaatg  840
cacggtgtga aggaggaggt gtttctcagc gtgccctgcg tgctgggaaa cagcggtctg  900
accgacgtca tccacatgac tctgaagccc gaggaggaga agcagctgag caacagtgcc  960
gagaccctat ggggcgtaca gaaagagctc accttg                             996

SEQ ID NO: 144          moltype = AA  length = 332
FEATURE                 Location/Qualifiers
REGION                  1..332
                        note = L-lactate dehydrogenase A chain-like
source                  1..332
                        mol_type = protein
                        organism = synthetic construct
SEQUENCE: 144
MTTKEKLITH VLAGEPVGSR SKVTVVGVGM VGMASAVSVL LKDLCDELCL IDVMEDKLKG  60
EVMDLQHGSL FCKTHKIVGD KDYSTTAHSK VVVVTAGARQ QEGESRLNLV QRNVNIFKFI  120
IPQIVKYSPN AILLVVSNPV DILTYVAWKL SGFPRHRVIG SGTNLDSGRF RHLMGEKLHL  180
HPSSCHGWII GEHGDSSVPV WSGVNVAGVS LKGLNPDMGT DADKEDWKHV HKMVVDGAYE  240
VIKLKGYTSW AIGMSVADLV ESILKNLHKV HPVSTLVKGM HGVKEEVFLS VPCVLGNSGL  300
TDVIHMTLKP EEEKQLSNSA ETLWGVQKEL TL                                 332

SEQ ID NO: 145          moltype = AA  length = 8
FEATURE                 Location/Qualifiers
REGION                  1..8
                        note = L-lactate dehydrogenase A chain-like fragment
source                  1..8
                        mol_type = protein
                        organism = synthetic construct
SEQUENCE: 145
FIIPQIVK                                                            8

SEQ ID NO: 146          moltype = AA  length = 16
FEATURE                 Location/Qualifiers
REGION                  1..16
                        note = L-lactate dehydrogenase A chain-like fragment
source                  1..16
                        mol_type = protein
                        organism = synthetic construct
SEQUENCE: 146
LITHVLAGEP VGSRSK                                                   16

SEQ ID NO: 147          moltype = AA  length = 14
FEATURE                 Location/Qualifiers
REGION                  1..14
```

-continued

```
                        note = L-lactate dehydrogenase A chain-like fragment
source                  1..14
                        mol_type = protein
                        organism = synthetic construct
SEQUENCE: 147
THVLAGEPVG SRSK                                                14

SEQ ID NO: 148          moltype = AA  length = 9
FEATURE                 Location/Qualifiers
REGION                  1..9
                        note = L-lactate dehydrogenase A chain-like fragment
source                  1..9
                        mol_type = protein
                        organism = synthetic construct
SEQUENCE: 148
VHPVSTLVK                                                      9

SEQ ID NO: 149          moltype = AA  length = 28
FEATURE                 Location/Qualifiers
REGION                  1..28
                        note = L-lactate dehydrogenase A chain-like fragment
source                  1..28
                        mol_type = protein
                        organism = synthetic construct
SEQUENCE: 149
VVVVTAGARQ QEGESRLNLV QRNVNIFK                                 28
```

FISH ALLERGY ANTIGEN

CROSS-REFERENCE TO RELATED APPLICATIONS

This application is a divisional application of U.S. patent application Ser. No. 16/309,453 filed on Dec. 13, 2018, which is a U.S. national stage filing, under 35 U.S.C. § 371(c), of International Application No. PCT/JP2017/017018, filed on Apr. 28, 2017, which claims priority to Japanese Patent Application No. 2016-119919, filed on Jun. 16, 2016. The entire contents of each of the aforementioned applications, including drawings and sequence listings, are incorporated herein by reference.

REFERENCE TO SEQUENCE LISTING

The instant application contains a Sequence Listing XML file which has been submitted electronically in XML format and is hereby incorporated by reference in its entirety. Said XML file, created on Oct. 19, 2023 is named Seq_Listing_129249_00403. XML and is 235,242 bytes in size.

TECHNICAL FIELD

The present invention relates to a novel antigen of an allergy to fish. The present invention also relates to a kit, a composition, and a method for diagnosing allergy to fish. The present invention also relates to a pharmaceutical composition comprising the antigen and fish or fish eggs in which the antigen is eliminated or reduced, a processed product of the fish or the fish eggs or fish which lay the fish eggs or have hatched from the eggs. The present invention further relates to a tester for determining the presence or absence of a fish antigen in an object of interest.

BACKGROUND ART

In blood and tissues of allergic patients, IgE antibodies specific to particular antigens are produced. Physiological consequences caused by interaction between such IgE antibodies and such particular antigens elicit allergic reactions.

In the process of production of conventional allergy testing agents, antigen reagents are commonly prepared simply by grinding a candidate allergenic food, food material or the like (Patent Literature 1). Therefore, numerous proteins were contained in a reagent and there the content of each protein was very little. For this reason, the only case where conventional allergy tests have permitted detection of a positive allergic reaction is when in a conventional antigen reagent containing many proteins, a particular antigen protein which causes the allergic reaction (allergen component) is present in an amount exceeding a threshold that allows determination of a positive reaction for binding to an IgE antibody. However, no determination of a positive reaction was possible and diagnosis efficiency was not sufficiently high when using a conventional allergy testing agent in patients possessing an IgE antibody binding to an allergen component present in small amounts in an allergen such as food, food material or the like.

The severity and symptoms of an allergic reaction do not necessarily correlate with the content of an allergen component. Even when a patient's IgE antibody reacts with an allergen component present in trace amounts in a candidate allergic food and food material, the allergic reaction may develop allergic symptoms or may affect the severity of those symptoms.

An attempt to increase the diagnostic efficiency is being made by examining IgE antibodies to each protein composing food and food material to distinguish sensitization that directly contributes to a diagnosis from sensitization based on cross-antigenicity by a pan-allergen or the like. The allergens set forth in Table below are currently known as fish allergens (Non Patent Literature 1).

TABLE 1

| Species | Allergen | Biochemical name | MW(SDS-PAGE) | Food Allergen | Entry Date | Modified Date |
|---|---|---|---|---|---|---|
| *Clupea harengus* (Atlantic herring) | | | | | | |
| | Clu h 1 | Beta-parvalbumin | 12 kDa | Yes | 2016 Apr. 4 | 2014 Nov. 3 |
| *Cyprinus carpio* (Common carp) | | | | | | |
| | Cyp c 1 | beta-parvalbumin | 12 | Yes | 2016 Apr. 4 | 2013 Sep. 10 |
| *Gadus callarias* (Baltic cod) | | | | | | |
| | Gad c 1 | Beta-parvalbumin | 12 | Yes | 2016 Apr. 4 | 2010 Apr. 29 |
| *Gadus morhua* (Atlantic cod) | | | | | | |
| | Gad m 1 | Beta-parvalbumin | 12 | Yes | 2016 Apr. 4 | 2011 Jan. 25 |
| | Gad m 2 | Beta-enolase | 47.3 kDa | Yes | 2016 Apr. 4 | 2012 Jul. 30 |
| | Gad m 3 | Aldolase A | 40 kDa | Yes | 2016 Apr. 4 | 2012 Jul. 30 |
| *Lates calcarifer* (Barramundi) | | | | | | |
| | Lat c 1 | Beta-parvalbumin | 11.5 kDa | Yes | 2016 Apr. 4 | 2014 Nov. 13 |
| *Lepidorhombus whiffiagonis* (Megrim, Whiff, Gallo) | | | | | | |
| | Lep w 1 | Beta-parvalbumin | 11.5 kDa | Yes | 2016 Apr. 4 | 2010 Apr. 29 |
| *Oncorhynchus keta* (Chum salmon) | | | | | | |
| | Onc k 5 | beta-prime-component of vitellogenin | 18 kDa | Yes | 2016 Apr. 4 | 2012 Dec. 18 |
| *Oncorhynchus mykiss* (Rainbow trout) | | | | | | |
| | Onc m 1 | Beta-parvalbumin | 12 kDa | Yes | 2016 Apr. 4 | 2011 Apr. 14 |
| *Oreochromis mossambicus* (Mozambique tilapia) | | | | | | |
| | Ore m 4 | Tropomyosin | 33 kDa | Yes | 2016 Apr. 4 | 2012 Jul. 30 |

TABLE 1-continued

| Species | Allergen | Biochemical name | MW(SDS-PAGE) | Food Allergen | Entry Date | Modified Date |
|---|---|---|---|---|---|---|
| *Salmo salar* (Atlantic salmon) | | | | | | |
| | Sal s 1 | Beta-parvalbumin 1 | 12 | Yes | 2016 Apr. 4 | 2010 Apr. 29 |
| | Sal s 2 | Beta-Enolase | 47.3 kDa | Yes | 2016 Apr. 4 | 2011 Aug. 26 |
| | Sal s 3 | Aldolase A | 40 | Yes | 2016 Apr. 4 | 2012 Jul. 30 |
| *Sardinops sagax* (Pacific pilchard) | | | | | | |
| | Sar sa 1 | Beta-parvalbumin | 12 kDa | Yes | 2016 Apr. 4 | 2010 Apr. 29 |
| *Sebastes marinus* (Ocean perch, redfish, snapper) | | | | | | |
| | Seb m 1 | Beta-parvalbumin | 11 kDa | Yes | 2016 Apr. 4 | 2010 Apr. 29 |
| *Thunnus albacares* (Yellowfin tuna) | | | | | | |
| | Thu a 1 | Beta-parvalbumin | 11 kDa | Yes | 2016 Apr. 4 | 2010 Apr. 29 |
| | Thu a 2 | Beta-enolase | 50 | Yes | 2016 Apr. 4 | 2012 Jul. 30 |
| | Thu a 3 | Aldolase A | 40 | Yes | 2016 Apr. 4 | 2012 Jul. 30 |
| *Xiphias gladius* (Swordfish) | | | | | | |
| | Xip g 1 | Beta-parvalbumin | 11.5 kDa | Yes | 2016 Apr. 4 | 2010 Apr. 29 |

However, while it is necessary to exhaustively identify allergen components in candidate allergic foods and food materials in order to enhance the reliability of allergy tests, the patient detection rate by the measurement of such allergen components is far from sufficient. Identification of novel allergens in fish is very important not only for increasing the precision of diagnosis, but also for determining targets of therapeutic agents and low allergenic foods and low allergenic food materials.

Meanwhile, in the field of protein separation and purification, various efforts have conventionally been made to develop methods for separating and purifying a protein or nucleic acid of interest from cell extracts or the like. Such methods may well be exemplified by dialysis based on salt concentration, and centrifugal separation.

Other efforts have been made to develop many purification methods based on electric charges of protein or nucleic acid residues or on the difference in molecular weight. Electric charge-based purification methods can be exemplified by column chromatography using ion exchange resins, and isoelectric focusing. Purifications based on molecular weight difference can be exemplified by centrifugal separation, molecular-sieve column chromatography, and SDS-PAGE (sodium dodecyl sulfate-polyacrylamide gel electrophoresis).

In recent years, a method for separating and purifying many different proteins from a small amount of sample has been used, which is more specifically a two-dimensional electrophoresis consisting of isoelectric focusing in the first dimension, followed by SDS-PAGE in the second dimension. The present applicant has conventionally developed some 2D electrophoresis methods with high separation ability (Patent Literature 2-5).

CITATION LIST

Patent Literature

PTL1: Japanese Patent Application Publication No. JP 2002-286716

PTL2: Japanese Patent Application Publication No. JP 2011-33544

PTL3: Japanese Patent Application Publication No. JP 2011-33546

PTL4: Japanese Patent Application Publication No. JP 2011-33547

PTL5: Japanese Patent Application Publication No. JP 2011-33548

Non-Patent Literature

NPTL1: Allergen Nomenclature, WHO/IUIS Allergen Nomenclature Sub-Committee, [searched on Jun. 9, 2016], internet<URL: http://www.allergen.org/search.php?allergenname=&allergensource=&TaxSource=Animalia+Chordata&TaxOrder=&foodallerg=1&bioname=>

SUMMARY OF INVENTION

Technical Problem

The present invention provides novel antigens of an allergy to fish. The present invention also provides methods and kits for diagnosing allergy to fish. The present invention also provides pharmaceutical compositions comprising such an antigen and fish or fish eggs in which such an antigen is eliminated or reduced, a processed product of the fish or the fish eggs or fish which lay the fish eggs or have hatched from the eggs.

Solution to Problem

In order to solve the aforementioned problems, the present inventors had made intensive studies to identify causative antigens of an allergy to fish. As a result, the inventors succeeded in identifying novel antigens to which an IgE antibody in the serum of a fish-allergic patient specifically binds. The present invention has been completed based on this finding.

Thus, in one embodiment, the present invention can be as defined below.

[1] A kit for diagnosing a fish allergy, the kit comprising, as an antigen, at least one protein defined in any one of the following (1) to (9):

(1) (1A) Alpha-actinin-3 or a variant thereof, which is a protein defined below in any of (1A-a) to (1A-e) which is an antigen for the fish allergy:

(1A-a) a protein comprising an amino acid sequence with deletion, substitution, insertion or addition of one or several amino acids in SEQ ID NO: 2;

(1A-b) a protein comprising an amino acid sequence having at least 70% identity to the amino acid sequence of SEQ ID NO: 2;

(1A-c) a protein comprising an amino acid sequence encoded by a nucleotide sequence with deletion, substitution, insertion or addition of one or several nucleotides in SEQ ID NO: 1;

(1A-d) a protein comprising an amino acid sequence encoded by a nucleotide sequence having at least 70% identity to the nucleotide sequence of SEQ ID NO: 1; or (1A-e) a protein comprising an amino acid sequence encoded by a nucleic acid that hybridizes under stringent conditions with a nucleic acid having a nucleotide sequence complementary to the nucleotide sequence of SEQ ID NO: 1; or (1B) a protein comprising an amino acid sequence of SEQ ID NO: 2 or 3;

(2) (2A) EEF1A2 binding protein-like or a variant thereof, which is a protein defined below in any of (2A-a) to (2A-e) which is an antigen for the fish allergy:

(2A-a) a protein comprising an amino acid sequence with deletion, substitution, insertion or addition of one or several amino acids in SEQ ID NO: 5;

(2A-b) a protein comprising an amino acid sequence having at least 70% identity to the amino acid sequence of SEQ ID NO: 5;

(2A-c) a protein comprising an amino acid sequence encoded by a nucleotide sequence with deletion, substitution, insertion or addition of one or several nucleotides in SEQ ID NO: 4;

(2A-d) a protein comprising an amino acid sequence encoded by a nucleotide sequence having at least 70% identity to the nucleotide sequence of SEQ ID NO: 4; or (2A-e) a protein comprising an amino acid sequence encoded by a nucleic acid that hybridizes under stringent conditions with a nucleic acid having a nucleotide sequence complementary to the nucleotide sequence of SEQ ID NO: 4; or (2B) a protein comprising at least one amino acid sequence selected from the group consisting of SEQ ID NOs: 5-8;

(3) (3A) Alpha-1,4-glucan phosphorylase or a variant thereof, which is a protein defined below in any of (3A-a) to (3A-e) which is an antigen for the fish allergy:

(3A-a) a protein comprising an amino acid sequence with deletion, substitution, insertion or addition of one or several amino acids in SEQ ID NO: 10;

(3A-b) a protein comprising an amino acid sequence having at least 70% identity to the amino acid sequence of SEQ ID NO: 10;

(3A-c) a protein comprising an amino acid sequence encoded by a nucleotide sequence with deletion, substitution, insertion or addition of one or several nucleotides in SEQ ID NO: 9;

(3A-d) a protein comprising an amino acid sequence encoded by a nucleotide sequence having at least 70% identity to the nucleotide sequence of SEQ ID NO: 9; or (3A-e) a protein comprising an amino acid sequence encoded by a nucleic acid that hybridizes under stringent conditions with a nucleic acid having a nucleotide sequence complementary to the nucleotide sequence of SEQ ID NO: 9; or (3B) a protein comprising at least one amino acid sequence selected from the group consisting of SEQ ID NOs: 10-16;

(4) (4A) Elongation factor 2 or a variant thereof, which is a protein defined below in any of (4A-a) to (4A-e) which is an antigen for the fish allergy:

(4A-a) a protein comprising an amino acid sequence with deletion, substitution, insertion or addition of one or several amino acids in SEQ ID NO: 19;

(4A-b) a protein comprising an amino acid sequence having at least 70% identity to the amino acid sequence of SEQ ID NO: 19;

(4A-c) a protein comprising an amino acid sequence encoded by a nucleotide sequence with deletion, substitution, insertion or addition of one or several nucleotides in SEQ ID NO: 18;

(4A-d) a protein comprising an amino acid sequence encoded by a nucleotide sequence having at least 70% identity to the nucleotide sequence of SEQ ID NO: 18; or (4A-e) a protein comprising an amino acid sequence encoded by a nucleic acid that hybridizes under stringent conditions with a nucleic acid having a nucleotide sequence complementary to the nucleotide sequence of SEQ ID NO: 18; or (4B) a protein comprising at least one amino acid sequence selected from the group consisting of SEQ ID NOs: 19-24;

(5) (5A) Heat shock cognate 70 kDa protein or a variant thereof, which is a protein defined below in any of (5A-a) to (5A-e) which is an antigen for the fish allergy:

(5A-a) a protein comprising an amino acid sequence with deletion, substitution, insertion or addition of one or several amino acids in SEQ ID NO: 26;

(5A-b) a protein comprising an amino acid sequence having at least 70% identity to the amino acid sequence of SEQ ID NO: 26;

(5A-c) a protein comprising an amino acid sequence encoded by a nucleotide sequence with deletion, substitution, insertion or addition of one or several nucleotides in SEQ ID NO: 25;

(5A-d) a protein comprising an amino acid sequence encoded by a nucleotide sequence having at least 70% identity to the nucleotide sequence of SEQ ID NO: 25; or (5A-e) a protein comprising an amino acid sequence encoded by a nucleic acid that hybridizes under stringent conditions with a nucleic acid having a nucleotide sequence complementary to the nucleotide sequence of SEQ ID NO: 25; or (5B) a protein comprising at least one amino acid sequence selected from the group consisting of SEQ ID NOs: 26-31;

(6) (6A) Serotransferrin or a variant thereof, which is a protein defined below in any of (6A-a) to (6A-e) which is an antigen for the fish allergy:

(6A-a) a protein comprising an amino acid sequence with deletion, substitution, insertion or addition of one or several amino acids in SEQ ID NO: 33;

(6A-b) a protein comprising an amino acid sequence having at least 70% identity to the amino acid sequence of SEQ ID NO: 33;

(6A-c) a protein comprising an amino acid sequence encoded by a nucleotide sequence with deletion, substitution, insertion or addition of one or several nucleotides in SEQ ID NO: 32;

(6A-d) a protein comprising an amino acid sequence encoded by a nucleotide sequence having at least 70% identity to the nucleotide sequence of SEQ ID NO: 32; or (6A-e) a protein comprising an amino acid sequence encoded by a nucleic acid that hybridizes under stringent conditions with a nucleic acid having a nucleotide sequence complementary to the nucleotide sequence of SEQ ID NO: 32; or (6B) a protein comprising at least one amino acid sequence selected from the group consisting of SEQ ID NOs: 33-41;

(7) (7A) Myosin binding protein H-like or a variant thereof, which is a protein defined below in any of (7A-a) to (7A-e) which is an antigen for the fish allergy:

(7A-a) a protein comprising an amino acid sequence with deletion, substitution, insertion or addition of one or several amino acids in SEQ ID NO: 43;

(7A-b) a protein comprising an amino acid sequence having at least 70% identity to the amino acid sequence of SEQ ID NO: 43;

(7A-c) a protein comprising an amino acid sequence encoded by a nucleotide sequence with deletion, substitution, insertion or addition of one or several nucleotides in SEQ ID NO: 42;

(7A-d) a protein comprising an amino acid sequence encoded by a nucleotide sequence having at least 70% identity to the nucleotide sequence of SEQ ID NO: 42; or (7A-e) a protein comprising an amino acid sequence encoded by a nucleic acid that hybridizes under stringent conditions with a nucleic acid having a nucleotide sequence complementary to the nucleotide sequence of SEQ ID NO: 42; or (7B) a protein comprising at least one amino acid sequence selected from the group consisting of SEQ ID NOs: 43-54, (8) (8A) Desmin (Fragment) or a variant thereof, which is a protein defined below in any of (8A-a) to (8A-e) which is an antigen for the fish allergy:

(8A-a) a protein comprising an amino acid sequence with deletion, substitution, insertion or addition of one or several amino acids in SEQ ID NO: 56;

(8A-b) a protein comprising an amino acid sequence having at least 70% identity to the amino acid sequence of SEQ ID NO: 56;

(8A-c) a protein comprising an amino acid sequence encoded by a nucleotide sequence with deletion, substitution, insertion or addition of one or several nucleotides in SEQ ID NO: 55;

(8A-d) a protein comprising an amino acid sequence encoded by a nucleotide sequence having at least 70% identity to the nucleotide sequence of SEQ ID NO: 55; or (8A-e) a protein comprising an amino acid sequence encoded by a nucleic acid that hybridizes under stringent conditions with a nucleic acid having a nucleotide sequence complementary to the nucleotide sequence of SEQ ID NO: 55; or (8B) a protein comprising at least one amino acid sequence selected from the group consisting of SEQ ID NOs: 56-59;

(9) (9A) Capping protein (Actin filament) muscle Z-line beta or a variant thereof, which is a protein defined below in any of (9A-a) to (9A-e) which is an antigen for the fish allergy:

(9A-a) a protein comprising an amino acid sequence with deletion, substitution, insertion or addition of one or several amino acids in SEQ ID NO: 61;

(9A-b) a protein comprising an amino acid sequence having at least 70% identity to the amino acid sequence of SEQ ID NO: 61;

(9A-c) a protein comprising an amino acid sequence encoded by a nucleotide sequence with deletion, substitution, insertion or addition of one or several nucleotides in SEQ ID NO: 60;

(9A-d) a protein comprising an amino acid sequence encoded by a nucleotide sequence having at least 70% identity to the nucleotide sequence of SEQ ID NO: 60; or (9A-e) a protein comprising an amino acid sequence encoded by a nucleic acid that hybridizes under stringent conditions with a nucleic acid having a nucleotide sequence complementary to the nucleotide sequence of SEQ ID NO: 60; or (9B) a protein comprising at least one amino acid sequence selected from the group consisting of SEQ ID NOs: 61-68.

[2] A composition for diagnosing a fish allergy, the composition comprising, as an antigen, at least one of proteins as defined above in any of (1) to (9) of [1].

[3] A method for providing an indicator for diagnosing a fish allergy in a subject, the method comprising the steps of:

(i) contacting a sample obtained from the subject with an antigen, wherein the sample is a solution comprising an IgE antibody;

(ii) detecting binding between an IgE antibody present in the sample from the subject and the antigen; and (iii) when the binding between the IgE antibody in the subject and the antigen is detected, an indicator of the fact that the subject has a fish allergy is provided;

wherein the antigen is at least one of proteins as defined above in any of (1) to (9) of [1].

[4] A pharmaceutical composition comprising at least one of proteins as defined above in any of (1) to (9) of [1].

[5] The pharmaceutical composition as set forth in [4] for the treatment of a fish allergy.

[6] A fish or a processed product of fish, in which an antigen is eliminated or reduced, wherein the antigen is at least one of proteins as defined above in any of (1) to (9) of [1].

[7] A tester for determining the presence or absence of a fish antigen in an object of interest, the tester comprising an antibody that binds to at least one of proteins as defined above in any of (1) to (9) of [1].

[8] A tester for determining the presence or absence of an antigen causing an allergy to fish in an object of interest, the tester comprising a primer having a nucleotide sequence complementary to at least one part of one of the nucleotide sequences set forth in SEQ ID NO: 1, 4, 9, 18, 25, 32, 42, 55, or 60.

[9] A kit for diagnosing a fish allergy, the kit comprising, as an antigen, at least one protein defined in any one of the following (10) to (14):

(10) (10A) Myosin heavy chain, fast skeletal muscle-like or a variant thereof, which is a protein defined below in any of (10A-a) to (10A-e) which is an antigen for the fish allergy:

(10A-a) a protein comprising an amino acid sequence with deletion, substitution, insertion or addition of one or several amino acids in SEQ ID NO: 70;

(10A-b) a protein comprising an amino acid sequence having at least 70% identity to the amino acid sequence of SEQ ID NO: 70;

(10A-c) a protein comprising an amino acid sequence encoded by a nucleotide sequence with deletion, substitution, insertion or addition of one or several nucleotides in SEQ ID NO: 69;

(10A-d) a protein comprising an amino acid sequence encoded by a nucleotide sequence having at least 70% identity to the nucleotide sequence of SEQ ID NO: 69; or (10A-e) a protein comprising an amino acid sequence encoded by a nucleic acid that hybridizes under stringent conditions with a nucleic acid having a nucleotide sequence complementary to the nucleotide sequence of SEQ ID NO: 69; or (10B) a protein comprising at least one amino acid sequence selected from the group consisting of SEQ ID NOs: 70-108;

(11) (11A) Glycogen phosphorylase, muscle form-like or a variant thereof, which is a protein defined below in any of (11A-a) to (11A-e) which is an antigen for the fish allergy:

(11A-a) a protein comprising an amino acid sequence with deletion, substitution, insertion or addition of one or several amino acids in SEQ ID NO: 110;

(11A-b) a protein comprising an amino acid sequence having at least 70% identity to the amino acid sequence of SEQ ID NO: 110;

(11A-c) a protein comprising an amino acid sequence encoded by a nucleotide sequence with deletion, substitution, insertion or addition of one or several nucleotides in SEQ ID NO: 109;

(11A-d) a protein comprising an amino acid sequence encoded by a nucleotide sequence having at least 70% identity to the nucleotide sequence of SEQ ID NO: 109; or (11A-e) a protein comprising an amino acid sequence encoded by a nucleic acid that hybridizes under stringent conditions with a nucleic acid having a nucleotide sequence complementary to the nucleotide sequence of SEQ ID NO: 109; or (11B) a protein comprising at least one amino acid sequence selected from the group consisting of SEQ ID NOs: 110-119;

(12) (12A) Myosin-binding protein C, fast-type-like or a variant thereof, which is a protein defined below in any of (12A-a) to (12A-e) which is an antigen for the fish allergy:

(12A-a) a protein comprising an amino acid sequence with deletion, substitution, insertion or addition of one or several amino acids in SEQ ID NO: 121;

(12A-b) a protein comprising an amino acid sequence having at least 70% identity to the amino acid sequence of SEQ ID NO: 121;

(12A-c) a protein comprising an amino acid sequence encoded by a nucleotide sequence with deletion, substitution, insertion or addition of one or several nucleotides in SEQ ID NO: 120;

(12A-d) a protein comprising an amino acid sequence encoded by a nucleotide sequence having at least 70% identity to the nucleotide sequence of SEQ ID NO: 120; or (12A-e) a protein comprising an amino acid sequence encoded by a nucleic acid that hybridizes under stringent conditions with a nucleic acid having a nucleotide sequence complementary to the nucleotide sequence of SEQ ID NO: 120; or (12B) a protein comprising at least one amino acid sequence selected from the group consisting of SEQ ID NOs: 121-136;

(13) (13A) ATP synthase subunit beta, mitochondrial or a variant thereof, which is a protein defined below in any of (13A-a) to (13A-e) which is an antigen for the fish allergy:

(13A-a) a protein comprising an amino acid sequence with deletion, substitution, insertion or addition of one or several amino acids in SEQ ID NO: 138;

(13A-b) a protein comprising an amino acid sequence having at least 70% identity to the amino acid sequence of SEQ ID NO: 138;

(13A-c) a protein comprising an amino acid sequence encoded by a nucleotide sequence with deletion, substitution, insertion or addition of one or several nucleotides in SEQ ID NO: 137;

(13A-d) a protein comprising an amino acid sequence encoded by a nucleotide sequence having at least 70% identity to the nucleotide sequence of SEQ ID NO: 137; or (13A-e) a protein comprising an amino acid sequence encoded by a nucleic acid that hybridizes under stringent conditions with a nucleic acid having a nucleotide sequence complementary to the nucleotide sequence of SEQ ID NO: 137; or (13B) a protein comprising at least one amino acid sequence selected from the group consisting of SEQ ID NOs: 138-142;

(14) (14A) L-lactate dehydrogenase A chain-like or a variant thereof, which is a protein defined below in any of (14A-a) to (14A-e) which is an antigen for the fish allergy:

(14A-a) a protein comprising an amino acid sequence with deletion, substitution, insertion or addition of one or several amino acids in SEQ ID NO: 144;

(14A-b) a protein comprising an amino acid sequence having at least 70% identity to the amino acid sequence of SEQ ID NO: 144;

(14A-c) a protein comprising an amino acid sequence encoded by a nucleotide sequence with deletion, substitution, insertion or addition of one or several nucleotides in SEQ ID NO: 143;

(14A-d) a protein comprising an amino acid sequence encoded by a nucleotide sequence having at least 70% identity to the nucleotide sequence of SEQ ID NO: 143; or (14A-e) a protein comprising an amino acid sequence encoded by a nucleic acid that hybridizes under stringent conditions with a nucleic acid having a nucleotide sequence complementary to the nucleotide sequence of SEQ ID NO: 143; or (14B) a protein comprising at least one amino acid sequence selected from the group consisting of SEQ ID NOs: 144-149.

[10] A composition for diagnosing a fish allergy, the composition comprising, as an antigen, at least one of proteins as defined above in any of (10) to (14) of [9].

[11] A method for providing an indicator for diagnosing a fish allergy in a subject, the method comprising the steps of:

(i) contacting a sample obtained from the subject with an antigen, wherein the sample is a solution comprising an IgE antibody;

(ii) detecting binding between an IgE antibody present in the sample from the subject and the antigen; and (iii) when the binding between the IgE antibody in the subject and the antigen is detected, an indicator of the fact that the subject has a fish allergy is provided;

wherein the antigen is at least one of proteins as defined above in any of (10) to (14) of [9].

[12] A pharmaceutical composition comprising at least one of proteins as defined above in any of (10) to (14) of [9].

[13] The pharmaceutical composition as set forth in for the treatment of a fish allergy.

[14] A fish or a processed product of fish, in which an antigen is eliminated or reduced, wherein the antigen is at least one of proteins as defined above in any of (10) to (14) of [9].

[15] A tester for determining the presence or absence of a fish antigen in an object of interest, the tester comprising an antibody that binds to at least one of proteins as defined above in any of (10) to (14) of [9].

[16] A tester for determining the presence or absence of an antigen causing an allergy to fish in an object of interest, the tester comprising a primer having a nucleotide sequence complementary to at least one part of one of the nucleotide sequences set forth in SEQ ID NO: 69, 109, 120, 137, or 143.

[17] A fish-derived antigen which is at least one of proteins as defined above in any of (1) to (9) of [1] and causes an allergy to fish.

[18] A fish-derived antigen which is at least one of proteins as defined above in any of (10) to (14) of [9] and causes an allergy to fish.

Advantageous Effects of Invention

The present invention can provide novel antigens of an allergy to fish. Since the novel antigens (allergen components) that trigger a fish allergy were identified in the present invention, it is possible to provide highly sensitive methods and kits for diagnosing an allergy to fish, pharmaceutical compositions comprising such an antigen, fish or fish eggs in which the antigen is eliminated or reduced, a processed product of the fish or the fish eggs or fish which lay the fish eggs or have hatched from the eggs, and testers for determining the presence or absence of a fish antigen in an object of interest.

BRIEF DESCRIPTION OF DRAWINGS

FIG. 1B is a photograph of an immunoblot obtained from the two-dimensional electrophoretic pattern of the proteins contained in the extract of the flesh of salmon by using a serum of Fish-allergic patient 2 (left panel) and a photograph of an immunoblot of the proteins stained with serum of Fish-allergic patient 3 (right panel). The numbers on the upper side of each photograph indicate isoelectric points.

DESCRIPTION OF EMBODIMENTS

Figure 1A:
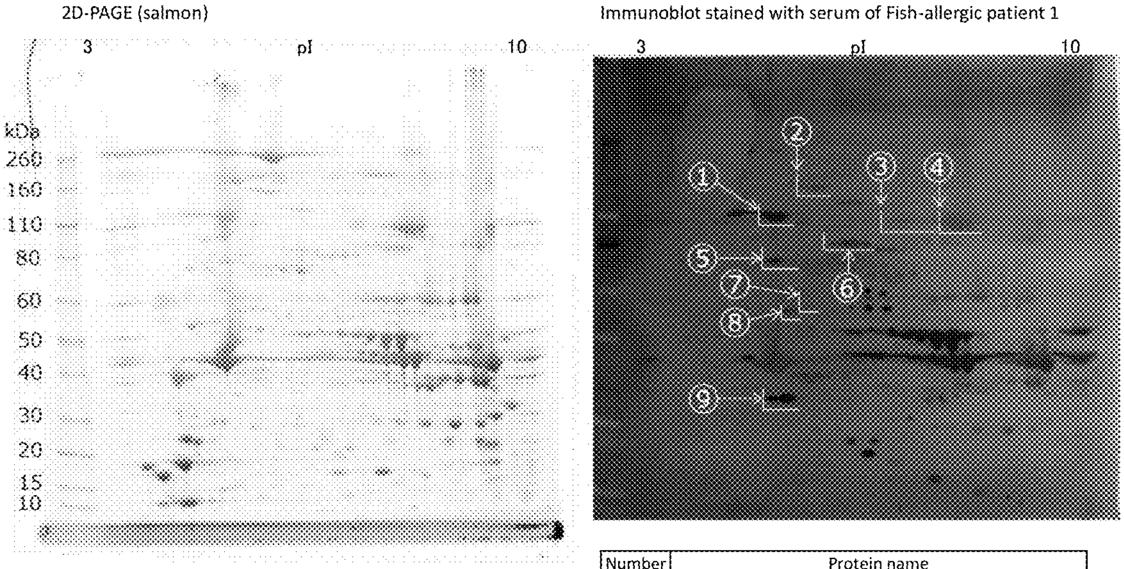
FIG. 1A is a photograph of a gel showing a protein electrophoretic pattern in two-dimensional electrophoresis of proteins contained in an extract of flesh of salmon (left panel) and a photograph of an immunoblot obtained from the two-dimensional electrophoretic pattern by using a serum of Fish-allergic patient 1 (right panel). The bands at the left of the photograph of the gel are bands of molecular weight markers and the numbers on the left side of the photograph of the gel are molecular weights of respective molecular weight markers (KDa). The numbers on the upper side of the photograph indicate isoelectric points.

The present invention will be described in detail below, but the present invention is not limited to them.

Unless otherwise defined herein, all scientific and technical terms used in relation to the present invention shall have meanings commonly understood by those skilled in the art.

As referred to herein, the "allergy" refers to the state in which, when a certain antigen reenters a living organism sensitized to said antigen, the living organism shows a hypersensitive reaction detrimental to the living organism. In blood and tissues of individuals with many food-allergic diseases, IgE antibodies specific to antigens are produced. IgE antibodies bind to mast cells or basophils. When an antigen specific to such an IgE antibody reenters the body of a patient with an allergic disease, said antigen combines with the IgE antibody bound to mast cells or basophils, and the IgE antibody crosslinks said antigen on the cell surface, resulting in physiological effects of IgE antibody-antigen interaction. Examples of such physiological effects include release of histamine, serotonin, heparin, eosinophil chemotactic factors, leucotrienes, or the like. These released substances provoke an allergic reaction resulting from the combination of an IgE antibody with particular antigens. Such allergic reactions caused by particular antigens occur through the aforementioned pathway.

As used herein, the term fish means teleost and elasmobranch among fishes, preferably teleost, more preferably those belonging to Salmoniformes, Perciformes, Anguilliformes, Gadiformes, and Pleuronectiformes, further preferably those belonging to Salmonidae, Carangidae, Congridae, Sparidae, Scombridae, Gadidae, Anguillidae, and Paralichthyidae, and even preferably salmon, horse mackerel, sea eel, black porgy, mackerel, sea bream, cod, young yellowtail, eel, and flatfish. The fish may be edible.

As used herein, the term fish eggs means eggs of fish. The fish eggs may be edible.

As referred to herein, the "allergy to fish" refers to the state in which an individual has an allergic reaction caused by proteins, etc. present in fish which act as an antigen. The allergy to fish can produce an allergic reaction upon contact with, or consumption of, an antigen present in fish. In general, allergic reactions caused by consumption of foods are particularly referred to as "food allergies". The allergy to fish may be a food allergy.

As referred to herein, the "antigen" refers to a substance that provokes an allergic reaction, and is also referred to as an "allergen component". The antigen is preferably a protein.

As referred to herein, the "protein" refers to a molecule having a structure in which naturally occurring amino acids are joined together by peptide bond. The number of amino acids present in a protein is not particularly limited, but proteins having about 2 to 50 amino acids joined together by peptide bond are in some cases called "peptides". In the case where amino acids can form different enantiomers, the amino acids are understood to form an L-enantiomer, unless otherwise indicated. The amino acid sequences of proteins or peptides as used herein are represented by one-letter symbols of amino acids in accordance with standard usage and the notational convention commonly used in the art. The leftward direction represents the amino-terminal direction, and the rightward direction represents the carboxy-terminal direction.

Identification of Antigens

Proteins contained in fish were analyzed by the aforementioned technique to identify antigens of an allergy to fish. To be specific, proteins were extracted from the flesh of fish and subjected to two-dimensional electrophoresis under the conditions described below.

The electrophoresis in the first dimension was isoelectric focusing, which was performed using isoelectric focusing gels with a gel-strip length of 5 to 10 cm and a gel pH range of 3 to 10. The pH gradient of the gels in the direction of electrophoresis was as follows: when the total gel-strip length is taken as 1, the gel-strip length up to pH 5 is taken as "a", the gel-strip length from pH 5 to 7 is taken as "b", and the gel-strip length above pH 7 is taken as "c", "a" is in the range of 0.15 to 0.3, "b" is in the range of 0.4 to 0.7, and "c" is in the range of 0.15 to 0.3. More specifically, the isoelectric focusing was performed using the IPG gels, Immobiline Drystrip (pH3-10NL), produced by GE Healthcare Bio-Sciences Corporation (hereinafter abbreviated as "GE"). The electrophoresis system used was IPGphor produced by GE. The maximum current of the electrophoresis system was limited to 75 μA per gel strip. The voltage program adopted to perform the first-dimensional isoelectric focusing was as follows: (1) a constant voltage step was performed at a constant voltage of 300 V until the volt-hours reached 750 Vhr (the current variation width during electrophoresis for 30 minutes before the end of this step was 5 μA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

The electrophoresis in the second dimension was SDS-PAGE, which was performed using polyacrylamide gels whose gel concentration at the distal end in the direction of electrophoresis was set to 3 to 6% and whose gel concentration at the proximal end was set to a higher value than that at the distal end. More specifically, the SDS-PAGE was performed using NuPAGE 4-12% Bris-Tris Gels (IPG well, Mini, 1 mm) produced by Life Technologies. The electrophoresis system used was XCell SureLock Mini-Cell produced by Life Technologies. The electrophoresis was run at a constant voltage of 200 V for about 45 minutes using an electrophoresis buffer composed of 50 mM MOPS, 50 mM Tris base, 0.1% (w/v) SDS and 1 mM EDTA.

As a result, the following spots in a two-dimensional electrophoresis gel run under the conditions described above for fish proteins have been revealed to exhibit specific binding to IgE antibodies from patients having an allergy to fish and being diagnosed as having immediate-type allergy.

Spot 1: Molecular weight 80 to 160 kDa, pI 3.0 to 7.0
Spot 2: Molecular weight 110 to 260 kDa, pI 4.0 to 8.0
Spot 3: Molecular weight 80 to 160 kDa, pI 4.0 to 10.0
Spot 4: Molecular weight 80 to 160 kDa, pI 5.0 to 11.0
Spot 5: Molecular weight 50 to 110 kDa, pI 3.0 to 7.0
Spot 6: Molecular weight 60 to 110 kDa, pI 4.0 to 8.0
Spot 7: Molecular weight 40 to 80 kDa, pI 4.0 to 8.0
Spot 8: Molecular weight 40 to 80 kDa, pI 3.0 to 7.0
Spot 9: Molecular weight 20 to 50 kDa, pI 3.0 to 7.0
Spot 10: Molecular weight 160 to 300 kDa, pI 3.0 to 7.0
Spot 11: Molecular weight 80 to 160 kDa, pI 4.0 to 8.0
Spot 12: Molecular weight 100 to 160 kDa, pI 4.0 to 7.0
Spot 13: Molecular weight 30 to 70 kDa, pI 3.0 to 7.0
Spot 14: Molecular weight 20 to 50 kDa, pI 5.0 to 9.0

Antigen (1) Antigen in Spot 1

As the result of sequence identification of the antigen in spot 1 by mass spectroscopy, the following amino acid sequences of SEQ ID NO: 3 were detected.

Also, the mass spectroscopic data (SEQ ID NO: 3) obtained for spot 1 on a mass spectrometer was analyzed by comparing the data against the NCB1 protein data, and as a result, the antigen in question was identified as Alpha-actinin-3 (amino acid sequence: SEQ ID NO: 2, encoding nucleotide sequence: SEQ ID NO: 1). SEQ ID NO: 3 corresponds to amino acid 572 to 585 in SEQ ID NO: 2.

Accordingly, in the present invention, the antigen in spot 1 can be any of (1A-a) to (1A-e) and (1B) as defined below:

(1A-a) a protein comprising an amino acid sequence with deletion, substitution, insertion or addition of one or several amino acids in SEQ ID NO: 2;

(1A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 2;

(1A-c) a protein comprising an amino acid sequence encoded by a nucleotide sequence with deletion, substitution, insertion or addition of one or several nucleotides in SEQ ID NO: 1;

(1A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 1;

(1A-e) a protein comprising an amino acid sequence encoded by a nucleic acid that hybridizes under stringent conditions with a nucleic acid having a nucleotide sequence complementary to the nucleotide sequence of SEQ ID NO: 1;

(1B) a protein comprising at least one amino acid sequence of SEQ ID NO: 2 or 3, preferably a protein comprising all sequences of the amino acid sequences. As referred to above, the amino acid sequence of SEQ ID NO: 2 or 3 may be an amino acid sequence derived therefrom by deletion, substitution, insertion or addition of one or several amino acids.

The proteins of (1A-a) to (1A-e) and (1B) as defined above also include those proteins whose amino acid residues are modified by phosphorylation, sugar chain modification, aminoacylation, ring-opening, deamination or the like.

The proteins of (1A-a) to (1A-e) and (1B) as defined above can be proteins that are found in a protein spot with a molecular weight of around 80 to 160 kDa, preferably around 90 to 120 kDa and an isoelectric point of 3.0 to 7.0, preferably an isoelectric point of 3.0 to 6.0 on gels used in the two-dimensional electrophoresis performed under the conditions described above in the subsection titled "Identification of antigens".

Preferably, a protein that is an antigen in spot 1 is an antigen of an allergy to fish.

(2) Antigen in Spot 2

As the result of sequence identification of the antigen in spot 2 by mass spectroscopy, the following amino acid sequences of SEQ ID NOs: 6-8 were detected.

Also, the mass spectroscopic data obtained for spot 2 (SEQ ID NOs: 6-8) on a mass spectrometer was analyzed by comparing the data against the UniProt protein data, and as a result, the antigen in question was identified as EEF1A2 binding protein-like (amino acid sequence: SEQ ID NO: 5, encoding nucleotide sequence: SEQ ID NO: 4). SEQ ID NO: 6 corresponds to amino acid 143-159 in SEQ ID NO: 5, SEQ ID NO: 7 corresponds to amino acid 395-404 in SEQ ID NO: 5, and SEQ ID NO: 8 corresponds to amino acid 427-447 in SEQ ID NO: 5.

Accordingly, in the present invention, the antigen in spot 2 can be any of (2A-a) to (2A-e) and (2B) as defined below:

(2A-a) a protein comprising an amino acid sequence with deletion, substitution, insertion or addition of one or several amino acids in SEQ ID NO: 5;

(2A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 5;

(2A-c) a protein comprising an amino acid sequence encoded by a nucleotide sequence with deletion, substitution, insertion or addition of one or several nucleotides in SEQ ID NO: 4;

(2A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 4;

(2A-e) a protein comprising an amino acid sequence encoded by a nucleic acid that hybridizes under stringent conditions with a nucleic acid having a nucleotide sequence complementary to the nucleotide sequence of SEQ ID NO: 4;

(2B) a protein comprising at least one amino acid sequence selected from the group consisting of SEQ ID NOs: 5-8, preferably a protein comprising at least 2, 3, or all sequences of the amino acid sequences. As referred to above, the amino acid sequence of any of SEQ ID NOs: 5-8 may be an amino acid sequence derived therefrom by deletion, substitution, insertion or addition of one or several amino acids.

The proteins of (2A-a) to (2A-e) and (2B) as defined above also include those proteins whose amino acid residues are modified by phosphorylation, sugar chain modification, aminoacylation, ring-opening, deamination or the like.

The proteins of (2A-a) to (2A-e) and (2B) as defined above can be proteins that are found in a protein spot with a molecular weight of around 110 to 260 kDa, preferably around 120 to 160 kDa and an isoelectric point of 4.0 to 8.0, preferably an isoelectric point of 4.0 to 7.0 on gels used in the two-dimensional electrophoresis performed under the conditions described above in the subsection titled "Identification of antigens".

Preferably, a protein that is an antigen in spot 2 is an antigen of an allergy to fish.

(3) Antigen in Spot 3

As the result of sequence identification of the antigen in spot 3 by mass spectroscopy, the following amino acid sequences of SEQ ID NOs: 11-16 were detected.

Also, the mass spectroscopic data (SEQ ID NOs: 11-17) obtained for spot 3 on a mass spectrometer was analyzed by comparing the data against the Uniprot protein data, and as a result, the antigen in question was identified as Alpha-1, 4-glucan phosphorylase (amino acid sequence: SEQ ID NO: 10, encoding nucleotide sequence: SEQ ID NO: 9). SEQ ID NO: 11 corresponds to amino acid 836-844 in SEQ ID NO: 10, SEQ ID NO: 12 corresponds to amino acid 13-29 in SEQ ID NO: 10, SEQ ID NO: 13 corresponds to amino acid 657-681 in SEQ ID NO: 10, SEQ ID NO: 14 corresponds to amino acid 471-479 in SEQ ID NO: 10, SEQ ID NO: 15 corresponds to amino acid 546-555 in SEQ ID NO: 10, and SEQ ID NO: 16 corresponds to amino acid 727-741 in SEQ ID NO: 10.

Accordingly, in the present invention, the antigen in spot 3 can be any of (3A-a) to (3A-e) and (3B) as defined below:

(3A-a) a protein comprising an amino acid sequence with deletion, substitution, insertion or addition of one or several amino acids in SEQ ID NO: 10;

(3A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 10;

(3A-c) a protein comprising an amino acid sequence encoded by a nucleotide sequence with deletion, substitution, insertion or addition of one or several nucleotides in SEQ ID NO: 9;

(3A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 9.

(3A-e) a protein comprising an amino acid sequence encoded by a nucleic acid that hybridizes under stringent conditions with a nucleic acid having a nucleotide sequence complementary to the nucleotide sequence of SEQ ID NO: 9;

(3B) a protein comprising at least one amino acid sequence selected from the group consisting of SEQ ID NOs: 10-16, preferably a protein comprising at least 2, 3, 4, 5, 6 or all sequences of the amino acid sequences. More preferably, a protein comprising at least one amino acid sequence selected from the group consisting of SEQ ID NOs: 10, 12, 13, 15, and 16, preferably a protein comprising at least 2, 3, 4, or all sequences of the amino acid sequences. As referred to above, the amino acid sequence of any of SEQ ID NOs: 10-16 may be an amino acid sequence derived therefrom by deletion, substitution, insertion or addition of one or several amino acids.

The proteins of (3A-a) to (3A-e) and (3B) as defined above also include those proteins whose amino acid residues are modified by phosphorylation, sugar chain modification, aminoacylation, ring-opening, deamination or the like.

The proteins of (3A-a) to (3A-e) and (3B) as defined above can be proteins that are found in a protein spot with a molecular weight of around 80 to 160 kDa, preferably around 90 to 120 kDa and an isoelectric point of 4.0 to 10.0, preferably an isoelectric point of 5.0 to 8.0 on gels used in the two-dimensional electrophoresis performed under the conditions described above in the subsection titled "Identification of antigens".

Preferably, a protein that is an antigen in spot 3 is an antigen of an allergy to fish.

(4) Antigen in Spot 4

As the result of sequence identification of the antigen in spot 4 by mass spectroscopy, the following amino acid sequences of SEQ ID NOs: 20-24 were detected.

Also, the mass spectroscopic data (SEQ ID NOs: 20-24) obtained for spot 4 on a mass spectrometer was analyzed by comparing the data against the Uniprot protein data, and as a result, the antigen in question was identified as Elongation factor 2 (amino acid sequence: SEQ ID NO: 19, encoding nucleotide sequence: SEQ ID NO: 18). SEQ ID NO: 20 corresponds to amino acid 831-840 in SEQ ID NO: 19, SEQ ID NO: 21 corresponds to amino acid 560-571 in SEQ ID NO: 19, SEQ ID NO: 22 corresponds to amino acid 560-572 in SEQ ID NO: 19, SEQ ID NO: 23 corresponds to amino acid 677-688 in SEQ ID NO: 19, and SEQ ID NO: 24 corresponds to amino acid 620-629 in SEQ ID NO: 19.

Accordingly, in the present invention, the antigen in spot 4 can be any of (4-a) to (4-e) and (4B) as defined below:

(4A-a) a protein comprising an amino acid sequence with deletion, substitution, insertion or addition of one or several amino acids in SEQ ID NO: 19;

(4A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 19;

(4A-c) a protein comprising an amino acid sequence encoded by a nucleotide sequence with deletion, substitution, insertion or addition of one or several nucleotides in SEQ ID NO: 18;

(4A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 18;

(4A-e) a protein comprising an amino acid sequence encoded by a nucleic acid that hybridizes under stringent conditions with a nucleic acid having a nucleotide sequence complementary to the nucleotide sequence of SEQ ID NO: 18;

(4B) a protein comprising at least one amino acid sequence selected from the group consisting of SEQ ID NOs: 19-24, preferably a protein comprising at least 2, 3, 4, 5, 6 or all sequences of the amino acid sequences. As referred to above, the amino acid sequence of any of SEQ ID NOs: 19-24 may be an amino acid sequence derived therefrom by deletion, substitution, insertion or addition of one or several amino acids.

The proteins of (4A-a) to (4A-e) and (4B) as defined above also include those proteins whose amino acid residues are modified by phosphorylation, sugar chain modification, aminoacylation, ring-opening, deamination or the like.

The proteins of (4A-a) to (4A-e) and (4B) as defined above can be proteins that are found in a protein spot with a molecular weight of around 80 to 160 kDa, preferably around 90 to 120 kDa and an isoelectric point of 5.0 to 11.0, preferably an isoelectric point of 6.0 to 8.0 on gels used in the two-dimensional electrophoresis performed under the conditions described above in the subsection titled "Identification of antigens".

Preferably, a protein that is an antigen in spot 4 is an antigen of an allergy to fish.

(5) Antigen in Spot 5

As the result of sequence identification of the antigen in spot 5 by mass spectroscopy, the following amino acid sequences of SEQ ID NOs: 27-31 were detected.

Also, the mass spectroscopic data (SEQ ID NOs: 27-31) obtained for spot 5 on a mass spectrometer was analyzed by comparing the data against the Uniprot protein data, and as a result, the antigen in question was identified as Heat shock cognate 70 kDa protein (amino acid sequence: SEQ ID NO: 26, encoding nucleotide sequence: SEQ ID NO: 25). SEQ ID NO: 27 corresponds to amino acid 113-126 in SEQ ID NO: 26, SEQ ID NO: 28 corresponds to amino acid 513-526 in SEQ ID NO: 26, SEQ ID NO: 29 corresponds to amino acid 89-102 in SEQ ID NO: 26, SEQ ID NO: 30 corresponds to amino acid 584-597 in SEQ ID NO: 26, and SEQ ID NO: 31 corresponds to amino acid 138-159 in SEQ ID NO: 26.

Accordingly, in the present invention, the antigen in spot 5 can be any of (5A-a) to (5A-e) and (5B) as defined below:

(5A-a) a protein comprising an amino acid sequence with deletion, substitution, insertion or addition of one or several amino acids in SEQ ID NO: 26;

(5A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 26;

(5A-c) a protein comprising an amino acid sequence encoded by a nucleotide sequence with deletion, substitution, insertion or addition of one or several nucleotides in SEQ ID NO: 25;

(5A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 25;

(5A-e) a protein comprising an amino acid sequence encoded by a nucleic acid that hybridizes under stringent conditions with a nucleic acid having a nucleotide sequence complementary to the nucleotide sequence of SEQ ID NO: 25;

(5B) a protein comprising at least one amino acid sequence selected from the group consisting of SEQ ID NOs: 26-31, preferably a protein comprising at least 2, 3, 4, 5 or all sequences of the amino acid sequences. As referred to above, the amino acid sequence of any of SEQ ID NOs: 26-31 may be an amino acid sequence derived therefrom by deletion, substitution, insertion or addition of one or several amino acids.

The proteins of (5A-a) to (5A-e) and (5B) as defined above also include those proteins whose amino acid residues are modified by phosphorylation, sugar chain modification, aminoacylation, ring-opening, deamination or the like.

The proteins of (5A-a) to (5A-e) and (5B) as defined above can be proteins that are found in a protein spot with a molecular weight of around 50 to 110 kDa, preferably around 60 to 90 kDa and an isoelectric point of 3.0 to 7.0, preferably an isoelectric point of 3.0 to 6.0 on gels used in the two-dimensional electrophoresis performed under the conditions described above in the subsection titled "Identification of antigens".

Preferably, a protein that is an antigen is an antigen of an allergy to fish.

(6) Antigen in Spot 6

As the result of sequence identification of the antigen in spot 6 by mass spectroscopy, the following amino acid sequences of SEQ ID NOs: 34-41 were detected.

Also, the mass spectroscopic data (SEQ ID NOs: 34-41) obtained for spot 6 on a mass spectrometer was analyzed by comparing the data against the Uniprot protein data, and as a result, the antigen in question was identified as Serotransferrin (amino acid sequence: SEQ ID NO: 33, encoding nucleotide sequence: SEQ ID NO: 32). SEQ ID NO: 34 corresponds to amino acid 330-341 in SEQ ID NO: 33, SEQ ID NO: 35 corresponds to amino acid 332-341 in SEQ ID NO: 33, SEQ ID NO: 36 corresponds to amino acid 264-274 in SEQ ID NO: 33, SEQ ID NO: 37 corresponds to amino acid 113-124 in SEQ ID NO: 33, SEQ ID NO: 38 corresponds to amino acid 112-124 in SEQ ID NO: 33, SEQ ID NO: 39 corresponds to amino acid 112-125 in SEQ ID NO: 33, SEQ ID NO: 40 corresponds to amino acid 275-292 in SEQ ID NO: 33, and SEQ ID NO: 41 corresponds to amino acid 436-446 in SEQ ID NO: 33.

Accordingly, in the present invention, the antigen in spot 6 can be any of (6A-a) to (6A-e) and (6B) as defined below:

(6A-a) a protein comprising an amino acid sequence with deletion, substitution, insertion or addition of one or several amino acids in SEQ ID NO: 33;

(6A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 33;

(6A-c) a protein comprising an amino acid sequence encoded by a nucleotide sequence with deletion, substitution, insertion or addition of one or several nucleotides in SEQ ID NO: 32;

(6A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 32;

(6A-e) a protein comprising an amino acid sequence encoded by a nucleic acid that hybridizes under stringent conditions with a nucleic acid having a nucleotide sequence complementary to the nucleotide sequence of SEQ ID NO: 32;

(6B) a protein comprising at least one amino acid sequence selected from the group consisting of SEQ ID NOs: 33-41, preferably a protein comprising at least 2, 3, 4, 5, 6, 7, 8 or all sequences of the amino acid sequences. As referred to above, the amino acid sequence of any of SEQ ID NOs: 33-41 may be an amino acid sequence derived therefrom by deletion, substitution, insertion or addition of one or several amino acids.

The proteins of (6A-a) to (6A-e) and (6B) as defined above also include those proteins whose amino acid residues are modified by phosphorylation, sugar chain modification, aminoacylation, ring-opening, deamination or the like.

The proteins of (6A-a) to (6A-e) and (6B) as defined above can be proteins that are found in a protein spot with a molecular weight of around 60 to 110 kDa, preferably around 70 to 100 kDa and an isoelectric point of 4.0 to 8.0, preferably an isoelectric point of 5.0 to 7.0 on gels used in the two-dimensional electrophoresis performed under the conditions described above in the subsection titled "Identification of antigens".

Preferably, a protein that is an antigen in spot 6 is an antigen of an allergy to fish.

(7) Antigen in Spot 7

As the result of sequence identification of the antigen in spot 7 by mass spectroscopy, the following amino acid sequences of SEQ ID NOs: 44-54 were detected.

Also, the mass spectroscopic data (SEQ ID NOs: 44-54) obtained for spot 7 on a mass spectrometer was analyzed by comparing the data against the Uniprot protein data, and as a result, the antigen in question was identified as Myosin binding protein H-like (amino acid sequence: SEQ ID NO: 43, encoding nucleotide sequence: SEQ ID NO: 42). SEQ ID NO: 44 corresponds to amino acid 275-292 in SEQ ID NO: 43, SEQ ID NO: 45 corresponds to amino acid 49-66 in SEQ ID NO: 43, SEQ ID NO: 46 corresponds to amino acid 67-77 in SEQ ID NO: 43, SEQ ID NO: 47 corresponds to amino acid 310-323 in SEQ ID NO: 43, SEQ ID NO: 48 corresponds to amino acid 382-401 in SEQ ID NO: 43, SEQ ID NO: 49 corresponds to amino acid 402-418 in SEQ ID NO: 43, SEQ ID NO: 50 corresponds to amino acid 210-219 in SEQ ID NO: 43, SEQ ID NO: 51 corresponds to amino acid 210-228 in SEQ ID NO: 43, SEQ ID NO: 52 corresponds to amino acid 152-183 in SEQ ID NO: 43, SEQ ID NO: 53 corresponds to amino acid 100-112 in SEQ ID NO: 43, and SEQ ID NO: 54 corresponds to amino acid 113-129 in SEQ ID NO: 43.

Accordingly, in the present invention, the antigen in spot 7 can be any of (7A-a) to (7A-e) and (7B) as defined below:

(7A-a) a protein comprising an amino acid sequence with deletion, substitution, insertion or addition of one or several amino acids in SEQ ID NO: 43;

(7A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 43;

(7A-c) a protein comprising an amino acid sequence encoded by a nucleotide sequence with deletion, substitution, insertion or addition of one or several nucleotides in SEQ ID NO: 42;

(7A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 42;

(7A-e) a protein comprising an amino acid sequence encoded by a nucleic acid that hybridizes under stringent conditions with a nucleic acid having a nucleotide sequence complementary to the nucleotide sequence of SEQ ID NO: 42;

(7B) a protein comprising at least one amino acid sequence selected from the group consisting of SEQ ID NOs: 43-54, preferably a protein comprising at least 2, 3, 4, 5, 6, 7, 8, 9, 10, 11 or all sequences of the amino acid sequences; As referred to above, the amino acid sequence of any of SEQ ID NOs: 43-54 may be an amino acid sequence derived therefrom by deletion, substitution, insertion or addition of one or several amino acids.

The proteins of (7A-a) to (7A-e) and (7B) as defined above also include those proteins whose amino acid residues are modified by phosphorylation, sugar chain modification, aminoacylation, ring-opening, deamination or the like.

The proteins of (7A-a) to (7A-e) and (7B) as defined above can be proteins that are found in a protein spot with a molecular weight of around 40 to 80 kDa, preferably around 50 to 60 kDa and an isoelectric point of 4.0 to 8.0, preferably an isoelectric point of 4.0 to 7.0 on gels used in the two-dimensional electrophoresis performed under the conditions described above in the subsection titled "Identification of antigens".

Preferably, a protein that is an antigen in spot 7 is an antigen of an allergy to fish.

(8) Antigen in Spot 8

As the result of sequence identification of the antigen in spot 8 by mass spectroscopy, the following amino acid sequences of SEQ ID NOs: 57-59 were detected.

Also, the mass spectroscopic data (SEQ ID NOs: 57-59) obtained for spot 8 on a mass spectrometer was analyzed by comparing the data against the Uniprot protein data, and as a result, the antigen in question was identified as Desmin (Fragment) (amino acid sequence: SEQ ID NO: 56, encoding nucleotide sequence: SEQ ID NO: 55). SEQ ID NO: 57 corresponds to amino acid 364-380 in SEQ ID NO: 56, SEQ ID NO: 58 corresponds to amino acid 74-94 in SEQ ID NO: 56, and SEQ ID NO: 59 corresponds to amino acid 273-282 in SEQ ID NO: 56.

Accordingly, in the present invention, the antigen in spot 8 can be any of (8A-a) to (8A-e) and (8B) as defined below:

(8A-a) a protein comprising an amino acid sequence with deletion, substitution, insertion or addition of one or several amino acids in SEQ ID NO: 56;

(8A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 56;

(8A-c) a protein comprising an amino acid sequence encoded by a nucleotide sequence with deletion, substitution, insertion or addition of one or several nucleotides in SEQ ID NO: 55;

(8A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 55;

(8A-e) a protein comprising an amino acid sequence encoded by a nucleic acid that hybridizes under stringent conditions with a nucleic acid having a nucleotide sequence complementary to the nucleotide sequence of SEQ ID NO: 55;

(8B) a protein comprising at least one amino acid sequence selected from the group consisting of SEQ ID NOs: 56-59, preferably a protein comprising at least 2, 3, or all sequences of the amino acid sequences. As referred to above, the amino acid sequence of any of SEQ ID NOs: 56-59 may be an amino acid sequence derived therefrom by deletion, substitution, insertion or addition of one or several amino acids.

The proteins of (8A-a) to (8A-e) and (8B) as defined above also include those proteins whose amino acid residues are modified by phosphorylation, sugar chain modification, aminoacylation, ring-opening, deamination or the like.

The proteins of (8A-a) to (8A-e) and (8B) as defined above can be proteins that are found in a protein spot with a molecular weight of around 40 to 80 kDa, preferably around 50 to 60 kDa and an isoelectric point of 3.0 to 7.0, preferably an isoelectric point of 4.0 to 6.0 on gels used in the two-dimensional electrophoresis performed under the conditions described above in the subsection titled "Identification of antigens".

Preferably, a protein that is an antigen in spot 8 is an antigen of an allergy to fish.

(9) Antigen in Spot 9

As the result of sequence identification of the antigen in spot 9 by mass spectroscopy, the following amino acid sequences of SEQ ID NOs: 62-68 were detected.

Also, the mass spectroscopic data (SEQ ID NOs: 62-68) obtained for spot 9 on a mass spectrometer was analyzed by comparing the data against the UniProt protein data, and as a result, the antigen in question was identified as Capping protein (Actin filament) muscle Z-line beta (amino acid sequence: SEQ ID NO: 61, encoding nucleotide sequence: SEQ ID NO: 60). SEQ ID NO: 62 corresponds to amino acid 200-223 in SEQ ID NO: 61, SEQ ID NO: 63 corresponds to amino acid 238-254 in SEQ ID NO: 61, SEQ ID NO: 64 corresponds to amino acid 261-274 in SEQ ID NO: 61, SEQ ID NO: 65 corresponds to amino acid 224-235 in SEQ ID NO: 61, SEQ ID NO: 66 corresponds to amino acid 169-181 in SEQ ID NO: 61, SEQ ID NO: 67 corresponds to amino acid 245-254 in SEQ ID NO: 61, and SEQ ID NO: 68 corresponds to amino acid 79-95 in SEQ ID NO: 61.

Accordingly, the antigen in spot 9 in the present invention can be any of the proteins as defined below in (9A-a) to (9A-e), and (9B):

(9A-a) a protein comprising an amino acid sequence with deletion, substitution, insertion or addition of one or several amino acids in SEQ ID NO: 61;

(9A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 61;

(9A-c) a protein comprising an amino acid sequence encoded by a nucleotide sequence with deletion, substitution, insertion or addition of one or several nucleotides in SEQ ID NO: 60;

(9A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 60;

(9A-e) a protein comprising an amino acid sequence encoded by a nucleic acid that hybridizes under stringent conditions with a nucleic acid having a nucleotide sequence complementary to the nucleotide sequence of SEQ ID NO: 60;

(9B) a protein comprising at least one amino acid sequence selected from the group consisting of SEQ ID NOs: 61-68, preferably a protein comprising at least 2, 3, 4, 5, 6, 7 or all sequences of the amino acid sequences. As referred to above, the amino acid sequence of any of SEQ ID NOs: 61-68 may be an amino acid sequence derived therefrom by deletion, substitution, insertion or addition of one or several amino acids;

The proteins as defined above in (9A-a) to (9A-e), and (9B) also include those proteins whose amino acid residues are modified by phosphorylation, sugar chain modification, aminoacylation, ring-opening, deamination or the like.

The proteins as defined above in (9A-a) to (9A-e), and (9B) can be proteins that are found in a protein spot with a molecular weight of around 20 to 50 kDa, preferably around 30 to 40 kDa, and an isoelectric point of 3.0 to 7.0, preferably an isoelectric point of 4.0 to 6.0 on gels used in the two-dimensional electrophoresis performed under the conditions described above in the subsection titled "Identification of antigens".

Preferably, a protein that is an antigen in spot 9 is an antigen of an allergy to fish.

(10) Antigen in Spot 10

As the result of sequence identification of the antigen in spot 10 by mass spectroscopy, the following amino acid sequences of SEQ ID NOs: 71-108 were detected.

Also, the mass spectroscopic data (SEQ ID NOs: 71-108) obtained for spot 10 on a mass spectrometer was analyzed by comparing the data against the NCBI protein data, and as a result, the antigen in question was identified as myosin heavy chain, fast skeletal muscle-like (amino acid sequence: SEQ ID NO: 70, encoding nucleotide sequence: SEQ ID NO: 69). SEQ ID NO: 71 corresponds to amino acid 13-19 in SEQ ID NO:70, SEQ ID NO: 72 corresponds to amino acid 262-271 in SEQ ID NO: 70, SEQ ID NO: 73 corresponds to amino acid 996-1014 in SEQ ID NO: 70, SEQ ID NO: 74 corresponds to amino acid 951-961 in SEQ ID NO: 70, SEQ ID NO: 75 corresponds to amino acid 1293-1303 in SEQ ID NO: 70, SEQ ID NO: 76 corresponds to amino acid 1082-1091 in SEQ ID NO: 70, SEQ ID NO: 77 corresponds to amino acid 1847-1856 in SEQ ID NO:70, SEQ ID NO: 78 corresponds to amino acid 172-186 in SEQ ID NO: 70, SEQ ID NO: 79 corresponds to amino acid 919-937 in SEQ ID NO: 70, SEQ ID NO: 80 corresponds to amino acid 249-258 in SEQ ID NO: 70, SEQ ID NO: 81 corresponds to amino acid 706-717 in SEQ ID NO: 70, SEQ ID NO: 82 corresponds to amino acid 50-59 in SEQ ID NO: 70, SEQ ID NO: 83 corresponds to amino acid 415-430 in SEQ ID NO:70, SEQ ID NO: 84 corresponds to amino acid 834-845 in SEQ ID NO: 70, SEQ ID NO: 85 corresponds to amino acid 617-630 in SEQ ID NO: 70, SEQ ID NO: 86 corresponds to amino acid 1556-1567 in SEQ ID NO: 70, SEQ ID NO: 87 corresponds to amino acid 1391-1408 in SEQ ID NO: 70, SEQ ID NO: 88 corresponds to amino acid 1025-1040 in SEQ ID NO: 70, SEQ ID NO: 89 corresponds to amino acid 1813-1836 in SEQ ID NO:70, SEQ ID NO: 90 corresponds to amino acid 743-755 in SEQ ID NO: 70, SEQ ID NO: 91 corresponds to amino acid 1172-1192 in SEQ ID NO: 70, SEQ ID NO: 92 corresponds to amino acid 353-364 in SEQ ID NO: 70, SEQ ID NO: 93 corresponds to amino acid 1261-1292 in SEQ ID NO: 70, SEQ ID NO: 94 corresponds to amino acid 1783-1789 in SEQ ID NO: 70, SEQ ID NO: 95 corresponds to amino acid 1502-1519 in SEQ ID NO: 70, SEQ ID NO: 96 corresponds to amino acid 1484-1497 in SEQ ID NO:70, SEQ ID NO: 97 corresponds to amino acid 1194-1212 in SEQ ID NO: 70, SEQ ID NO: 98 corresponds to amino acid 1304-1314 in SEQ ID NO: 70, SEQ ID NO: 99 corresponds to amino acid 369-384 in SEQ ID NO: 70, SEQ ID NO: 100 corresponds to amino acid 1315-1322 in SEQ ID NO: 70, SEQ ID NO: 101 corresponds to amino acid 1536-1555 in SEQ ID NO: 70, SEQ ID NO: 102 corresponds to amino acid 237-248 in SEQ ID NO:70, SEQ ID NO: 103 corresponds to amino acid 1699-1725 in SEQ ID NO: 70, SEQ ID NO: 104 corresponds to amino acid 1092-1104 in SEQ ID NO: 70, SEQ ID NO: 105 corresponds to amino acid 407-414 in SEQ ID NO: 70, SEQ ID NO: 106 corresponds to amino acid 1897-1917 in SEQ ID NO: 70, SEQ ID NO:107 corresponds to amino acid 1458-1470 in SEQ ID NO: 70, and SEQ ID NO: 108 corresponds to amino acid 1373-1388 in SEQ ID NO: 70.

Accordingly, the antigen in spot 10 in the present invention can be any of the proteins as defined below in (10A-a) to (10A-e), and (10B):

(10A-a) a protein comprising an amino acid sequence with deletion, substitution, insertion or addition of one or several amino acids in SEQ ID NO: 70;

(10A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 70;

(10A-c) a protein comprising an amino acid sequence encoded by a nucleotide sequence with deletion, substitution, insertion or addition of one or several nucleotides in SEQ ID NO: 69;

(10A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 69;

(10A-e) a protein comprising an amino acid sequence encoded by a nucleic acid that hybridizes under stringent conditions with a nucleic acid having a nucleotide sequence complementary to the nucleotide sequence of SEQ ID NO: 69;

(10B) a protein comprising at least one amino acid sequence selected from the group consisting of SEQ ID NOs: 70-108, preferably a protein comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or all sequences of the amino acid sequences. As referred to above, the amino acid sequence of any of SEQ ID NOs: 70-108 may be an amino acid sequence derived therefrom by deletion, substitution, insertion or addition of one or several amino acids;

The proteins as defined above in (10A-a) to (10A-e), and (10B) also include those proteins whose amino acid residues are modified by phosphorylation, sugar chain modification, aminoacylation, ring-opening, deamination or the like.

The proteins as defined above in (10A-a) to (10A-e), and (10B) can be proteins that are found in a protein spot with a molecular weight of around 160 to 300 kDa, preferably around 160 to 260 kDa, more preferably around 200 to 230 kDa, and an isoelectric point of 3.0 to 7.0, preferably an isoelectric point of 4.0 to 6.0, more preferably an isoelectric point of 4.5 to 5.5 on gels used in the two-dimensional electrophoresis performed under the conditions described above in the subsection titled "Identification of antigens".

Preferably, a protein that is an antigen in spot 10 is an antigen of an allergy to fish.

(11) Antigen in Spot 11

As the result of sequence identification of the antigen in spot 11 by mass spectroscopy, the following amino acid sequences of SEQ ID NOs: 111-119 were detected.

Also, the mass spectroscopic data (SEQ ID NOs: 111-119) obtained for spot 11 on a mass spectrometer was analyzed by comparing the data against the NCBI protein data, and as a result, the antigen in question was identified as glycogen phosphorylase, muscle form-like (amino acid sequence: SEQ ID NO: 110, encoding nucleotide sequence: SEQ ID NO: 109). SEQ ID NO: 111 corresponds to amino acid 471-479 in SEQ ID NO: 110, SEQ ID NO: 112 corresponds to amino acid 547-555 in SEQ ID NO: 110, SEQ ID NO: 113 corresponds to amino acid 203-215 in SEQ ID NO:110, SEQ ID NO: 114 corresponds to amino acid 727-741 in SEQ ID NO: 110, SEQ ID NO: 115 corresponds to amino acid 508-520 in SEQ ID NO: 110, SEQ ID NO: 116 corresponds to amino acid 742-755 in SEQ ID NO: 110, SEQ ID NO: 117 corresponds to amino acid 13-29 in SEQ ID NO: 110, SEQ ID NO:118 corresponds to amino acid 775-784 in SEQ ID NO: 110, and SEQ ID NO: 119 corresponds to amino acid 643-656 in SEQ ID NO: 110.

Accordingly, the antigens in spot 11 in the present invention can be any of the proteins as defined below in (11A-a) to (11A-e) and (11B):

(11A-a) a protein comprising an amino acid sequence with deletion, substitution, insertion or addition of one or several amino acids in SEQ ID NO: 110;

(11A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 110;

(11A-c) a protein comprising an amino acid sequence encoded by a nucleotide sequence with deletion, substitution, insertion or addition of one or several nucleotides in SEQ ID NO: 109;

(11A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 109;

(11A-e) a protein comprising an amino acid sequence encoded by a nucleic acid that hybridizes under stringent conditions with a nucleic acid having a nucleotide sequence complementary to the nucleotide sequence of SEQ ID NO: 109;

(11B) a protein comprising at least one amino acid sequence selected from the group consisting of SEQ ID NOs: 110-119, preferably a protein comprising at least 2, 3, 4, 5, 6, 7, 8, 9 or all sequences of the amino acid sequences. As referred to above, the amino acid sequence of any of SEQ ID NOs: 110-119 may be an amino acid sequence derived therefrom by deletion, substitution, insertion or addition of one or several amino acids.

The proteins of (11A-a) to (11A-e) and (11B) as defined above also include those proteins whose amino acid residues are modified by phosphorylation, sugar chain modification, aminoacylation, ring-opening, deamination or the like.

The proteins of (11A-a) to (11A-e) and (11B) as defined above can be proteins that are found in a protein spot with a molecular weight of around 80 to 160 kDa, preferably around 80 to 110 kDa, more preferably around 90 to 110 kDa and an isoelectric point of 4.0 to 8.0, preferably an isoelectric point of 5.0 to 7.5, more preferably an isoelectric point of 6.5 to 7.0 on gels used in the two-dimensional electrophoresis performed under the conditions described above in the subsection titled "Identification of antigens".

Preferably, a protein that is an antigen in spot 11 is an antigen of an allergy to fish.

(12) Antigen in Spot 12

As the result of sequence identification of the antigen in spot 12 by mass spectroscopy, the following amino acid sequences of SEQ ID NOs: 122-136 were detected.

Also, the mass spectroscopic data (SEQ ID NOs: 122-136) obtained for spot 12 on a mass spectrometer was analyzed by comparing the data against the NCBI protein data, and as a result, the antigen in question was identified as myosin-binding protein C, fast-type-like (amino acid sequence: SEQ ID NO: 121, encoding nucleotide sequence: SEQ ID NO: 120). SEQ ID NO: 122 corresponds to amino acid 197-204 in SEQ ID NO: 121, SEQ ID NO: 123 corresponds to amino acid 421-434 in SEQ ID NO: 121, SEQ ID NO: 124 corresponds to amino acid 329-336 in SEQ ID NO:121, SEQ ID NO: 125 corresponds to amino acid 413-420 in SEQ ID NO: 121, SEQ ID NO:126 corresponds to amino acid 240-246 in SEQ ID NO: 121, SEQ ID NO: 127 corresponds to amino acid 214-228 in SEQ ID NO: 121, SEQ ID NO: 128 corresponds to amino acid 1014-1024 in SEQ ID NO: 121, SEQ ID NO: 129 corresponds to amino acid 842-855 in SEQ ID NO: 121, SEQ ID NO: 130 corresponds to amino acid 260-274 in SEQ ID NO:121, SEQ ID NO: 131 corresponds to amino acid 672-685 in SEQ ID NO: 121, SEQ ID NO: 132 corresponds to amino acid 506-512 in SEQ ID NO: 121, SEQ ID NO: 133 corresponds to amino acid 205-213 in SEQ ID NO: 121, SEQ ID NO: 134 corresponds to amino acid 165-182 in SEQ ID NO: 121, SEQ ID NO:135 corresponds to amino acid 321-328 in SEQ ID NO: 121, and SEQ ID NO: 136 corresponds to amino acid 70-82 in SEQ ID NO: 121.

Accordingly, the antigens in spot 12 in the present invention can be any of the proteins as defined below in (12A-a) to (12A-e) and (12B):

(12A-a) a protein comprising an amino acid sequence with deletion, substitution, insertion or addition of one or several amino acids in SEQ ID NO: 121;

(12A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 121;

(12A-c) a protein comprising an amino acid sequence encoded by a nucleotide sequence with deletion, substitution, insertion or addition of one or several nucleotides in SEQ ID NO: 119;

(12A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 119;

(12A-e) a protein comprising an amino acid sequence encoded by a nucleic acid that hybridizes under stringent conditions with a nucleic acid having a nucleotide sequence complementary to the nucleotide sequence of SEQ ID NO: 119;

(12B) a protein comprising at least one amino acid sequence selected from the group consisting of SEQ ID NOs: 121-136, preferably a protein comprising at least 2, 3, 4, 5, 6, 7, 8, 9, 10, 11, 12, 13, 14, 15 or all sequences of the amino acid sequences. As referred to above, the amino acid sequence of any of SEQ ID NOs: 121-136 may be an amino acid sequence derived therefrom by deletion, substitution, insertion or addition of one or several amino acids.

The proteins of (12A-a) to (12A-e) and (12B) as defined above also include those proteins whose amino acid residues are modified by phosphorylation, sugar chain modification, aminoacylation, ring-opening, deamination or the like.

The proteins of (12A-a) to (12A-e) and (12B) as defined above can be proteins that are found in a protein spot with a molecular weight of around 100 to 160 kDa, preferably around 110 to 150 kDa, more preferably around 120 to 140 kDa and an isoelectric point of 4.0 to 7.0, preferably an isoelectric point of 4.0 to 6.0, more preferably an isoelectric point of 5.0 to 6.0 on gels used in the two-dimensional electrophoresis performed under the conditions described above in the subsection titled "Identification of antigens".

Preferably, a protein that is an antigen in spot 12 is an antigen of an allergy to fish.

(13) Antigen in Spot 13

As the result of sequence identification of the antigen in spot 13 by mass spectroscopy, the following amino acid sequences of SEQ ID NOs: 139-142 were detected.

Also, the mass spectroscopic data (SEQ ID NOs: 139-142) obtained for spot 13 on a mass spectrometer was analyzed by comparing the data against the NCBI protein data, and as a result, the antigen in question was identified as ATP synthase subunit beta, mitochondrial (amino acid sequence: SEQ ID NO: 138, encoding nucleotide sequence: SEQ ID NO: 137). SEQ ID NO: 139 corresponds to amino acid 191-201 in SEQ ID NO: 138, SEQ ID NO: 140 corresponds to amino acid 449-469 in SEQ ID NO: 138, SEQ ID NO:141 corresponds to amino acid 202-214 in SEQ ID NO: 138, and SEQ ID NO: 142 corresponds to amino acid 178-187 in SEQ ID NO: 138.

Accordingly, the antigen in spot 13 in the present invention can be any of the proteins as defined below in (13A-a) to (13A-e), and (13B):

(13A-a) a protein comprising an amino acid sequence with deletion, substitution, insertion or addition of one or several amino acids in SEQ ID NO: 138;

(13A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 138;

(13A-c) a protein comprising an amino acid sequence encoded by a nucleotide sequence with deletion, substitution, insertion or addition of one or several nucleotides in SEQ ID NO: 137;

(13A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 137;

(13A-e) a protein comprising an amino acid sequence encoded by a nucleic acid that hybridizes under stringent conditions with a nucleic acid having a nucleotide sequence complementary to the nucleotide sequence of SEQ ID NO: 137;

(13B) a protein comprising at least one amino acid sequence selected from the group consisting of SEQ ID NOs: 138-142, preferably a protein comprising at least 2, 3, 4 or all sequences of the amino acid sequences. As referred to above, the amino acid sequence of any of SEQ ID NOs: 138-142 may be an amino acid sequence derived therefrom by deletion, substitution, insertion or addition of one or several amino acids;

The proteins as defined above in (13A-a) to (13A-e), and (13B) also include those proteins whose amino acid residues are modified by phosphorylation, sugar chain modification, aminoacylation, ring-opening, deamination or the like.

The proteins as defined above in (13A-a) to (13A-e), and (13B) can be proteins that are found in a protein spot with a molecular weight of around 30 to 70 kDa, preferably around 40 to 60 kDa, more preferably around 45 to 55 kDa and an isoelectric point of 3.0 to 7.0, preferably an isoelectric point of 3.0 to 6.0, more preferably an isoelectric point of 4.0 to 5.5 on gels used in the two-dimensional electrophoresis performed under the conditions described above in the subsection titled “Identification of antigens”.

Preferably, a protein that is an antigen in spot 13 is an antigen of an allergy to fish.

(14) Antigen in Spot 14

As the result of sequence identification of the antigen in spot 14 by mass spectroscopy, the following amino acid sequences of SEQ ID NOs: 145-149 were detected.

Also, the mass spectroscopic data (SEQ ID NOs: 145-149) obtained for spot 14 on a mass spectrometer was analyzed by comparing the data against the NCBI protein data, and as a result, the antigen in question was identified as L-lactate dehydrogenase A chain-like (amino acid sequence: SEQ ID NO: 144, encoding nucleotide sequence: SEQ ID NO: 143). SEQ ID NO: 145 corresponds to amino acid 119-126 in SEQ ID NO: 144, SEQ ID NO: 146 corresponds to amino acid 7-22 in SEQ ID NO: 144, SEQ ID NO: 147 corresponds to amino acid 9-22 in SEQ ID NO: 144, SEQ ID NO: 148 corresponds to amino acid 270-278 in SEQ ID NO: 144, and SEQ ID NO: 149 corresponds to amino acid 91-118 in SEQ ID NO: 144.

Accordingly, the antigens in spot 14 in the present invention can be any of the proteins as defined below in (14A-a) to (14A-e) and (14B):

(14A-a) a protein comprising an amino acid sequence with deletion, substitution, insertion or addition of one or several amino acids in SEQ ID NO: 144;

(14A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 144;

(14A-c) a protein comprising an amino acid sequence encoded by a nucleotide sequence with deletion, substitution, insertion or addition of one or several nucleotides in SEQ ID NO: 143;

(14A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 143;

(14A-e) a protein comprising an amino acid sequence encoded by a nucleic acid that hybridizes under stringent conditions with a nucleic acid having a nucleotide sequence complementary to the nucleotide sequence of SEQ ID NO: 143;

(14B) a protein comprising at least one amino acid sequence selected from the group consisting of SEQ ID NOs: 144-149, preferably a protein comprising at least 2, 3, 4, 5 or all sequences of the amino acid sequences. As referred to above, the amino acid sequence of any of SEQ ID NOs: 144-149 may be an amino acid sequence derived therefrom by deletion, substitution, insertion or addition of one or several amino acids.

The proteins of (14A-a) to (14A-e) and (14B) as defined above also include those proteins whose amino acid residues are modified by phosphorylation, sugar chain modification, aminoacylation, ring-opening, deamination or the like.

The proteins of (14A-a) to (14A-e) and (14B) as defined above can be proteins that are found in a protein spot with a molecular weight of around 20 to 50 kDa, preferably around 30 to 50 kDa, more preferably around 30 to 40 kDa and an isoelectric point of 5.0 to 9.0, preferably an isoelectric point of 6.0 to 8.0, more preferably an isoelectric point of 6.5 to 7.5 on gels used in the two-dimensional electrophoresis performed under the conditions described above in the subsection titled “Identification of antigens”.

Preferably, a protein that is an antigen in spot 14 is an antigen of an allergy to fish.

By stating herein "deletion, substitution, insertion or addition of one or several amino acids" in relation to amino acid sequence, it is meant that in an amino acid sequence of interest, one or several amino acids (e.g., 30%, preferably 25%, 20%, 15%, 10%, 5%, 3%, 2%, or 1% of amino acids with respect to the total length of the amino acid sequence) are deleted, one or several amino acids are substituted by any other amino acids, any other amino acids are inserted, and/or any other amino acids are added.

Among the aforementioned modifications, substitution is preferably conservative substitution. The "conservative substitution" refers to the substitution of a certain amino acid residue by a different amino acid residue having similar physicochemical characteristics, and can be any type of substitution as long as it does not substantially change the characteristics of the structure of the original sequence for example, any type of substitution is acceptable as long as any substituted amino acids do not disrupt the helical structure of the original sequence or other secondary structures that characterize the original sequence. The following gives examples of separate groups of amino acid residues that are conservatively substitutable with each other, but substitutable amino acid residues are not limited to the examples given below.

Group A: leucine, isoleucine, valine, alanine, methionine
Group B: aspartic acid, glutamic acid
Group C: asparagine, glutamine
Group D: lysine, arginine
Group E: serine, threonine
Group F: phenylalanine, tyrosine In the case of non-conservative substitution, one member belonging to one of the aforementioned groups can be replaced with a member belong to any other group. For example, in order to eliminate the possibility of unwanted sugar-chain modification, amino acids of group B, D or E as listed above may be substituted by those of any other group. Also, cysteines may be deleted or substituted by any other amino acids to prevent them from being folded into a protein in its tertiary structure. Also, in order to maintain the balance between hydrophilicity and hydrophobicity or to increase hydrophilicity for the purpose of facilitating synthesis, any amino acids may be substituted in consideration of the hydropathy scales of amino acids, which are a measure of the hydrophilic and hydrophobic properties of amino acids (J. Kyte and R. Doolittle, J. Mol. Biol., Vol. 157, p. 105-132, 1982).

As referred to herein, the percent identity between two amino acid sequences can be determined by visual inspection and mathematical calculation. Alternatively, the percent identity can be determined using a computer program. Examples of such computer programs include BLAST and ClustalW. In particular, various conditions (parameters) for identity searches with the BLAST program are described in Altschul, et al. (Nucl. Acids. Res., 25, p. 3389-3402, 1997), and are publicly available on the websites of the National Center for Biotechnology Information (NCBI) and DNA Data Bank of Japan (DDBJ) (Altschul, et al., BLAST Manual, Altschul, et al., NCB/NLM/NIH Bethesda, MD 20894). Also, the percent identity can be determined using a genetic information processing software program, such as GENETYX Ver.7 (Genetyx Corporation), DINASIS Pro (Hitachi Software Engineering Co., Ltd.), or Vector NTI (Infomax Inc.).

By stating herein "deletion, substitution, insertion or addition of one or several nucleotides" in relation to nucleotide sequence, it is meant that in a nucleotide sequence of interest, one or several nucleotides (e.g., 30%, preferably 25%, 20%, 15%, 10%, 5%, 3%, 2% or 1%, of nucleotides with respect to the total length of the nucleotide sequence) are deleted, one or several nucleotides are substituted by any other nucleotides, any other nucleotides are inserted, and/or any other nucleotides are added. It is preferable that such a nucleotide deletion, substitution, insertion or addition should not give rise to a frame shift in an amino acid coding sequence.

As referred to herein, the percent identity between two nucleotide sequences can be determined by visual inspection and mathematical calculation. Alternatively, the percent identity can be determined using a computer program. Examples of such sequence comparison computer programs include the BLASTN program, version 2.2.7, available on the website of the National Library of Medicine (http://www.ncbi.nlm nih.gov/blast/b12seq/b1s.html) (Altschul, et al. (1990) J. Mol. Biol., 215: 403-10), or the WU-BLAST 2.0 algorithm. Standard default parameter settings for WU-BLAST 2.0 are found and available on the following website: http://blast.wustl.edu.

As referred to herein, "under stringent conditions" means that hybridization takes place under moderately or highly stringent conditions. To be specific, the moderately stringent conditions can be easily determined by those having ordinary skill in the art on the basis of, for example, the length of DNA. Basic conditions are described in Sambrook, et al., Molecular Cloning: A Laboratory Manual, 3rd ed., ch. 6-7, Cold Spring Harbor Laboratory Press, 2001. The moderately stringent conditions include hybridization under the conditions of preferably 1×SSC to 6×SSC at 42° C. to 55° C., more preferably 1×SSC to 3×SSC at 45° C. to 50° C., most preferably 2×SSC at 50° C. In the case of using a hybridization solution containing, for example, about 50% formamide, a temperature around 5 to 15° C. lower than the foregoing should be adopted. Washing is also carried out under the conditions of 0.5×SSC to 6×SSC at 40° C. to 60° C. In the process of hybridization and washing, generally 0.05% to 0.2% SDS, preferably about 0.1% SDS, may be added. Likewise, the highly stringent conditions can be easily determined by those having ordinary skill in the art on the basis of, for example, the length of DNA. Generally, the highly stringent (high stringent) conditions include hybridization and/or washing at a higher temperature and/or a lower salt concentration than those adopted under the moderately stringent conditions. For example, hybridization is carried out under the conditions of 0.1×SSC to 2×SSC at 55° C. to 65° C., more preferably 0.1×SSC to 1×SSC at 60° C. to 65° C., most preferably 0.2×SSC at 63° C. Washing is carried out under the conditions of 0.2×SSC to 2×SSC at 50° C. to 68° C., more preferably 0.2×SSC at 60 to 65° C.

Antigens may be obtained by separating and purifying them from fish using a combination of protein purification methods well known to those skilled in the art. Also, antigens may be obtained by expressing them as recombinant proteins using a genetic recombination technique well known to those skilled in the art and by separating and purifying them using protein purification methods well known to those skilled in the art.

Exemplary protein purification methods include: solubility-based purification methods such as salt precipitation and solvent precipitation; purification methods based on molecular weight difference, such as dialysis, ultrafiltration, gel filtration and SDS-PAGE; charge-based purification methods such as ion exchange chromatography and hydroxylapatite chromatography; specific affinity-based purification methods such as affinity chromatography; purification methods based on hydrophobicity difference, such as reverse-phase high-performance liquid chromatography; and purification methods based on isoelectric point difference, such as isoelectric focusing.

Preparation of a protein by a genetic recombination technique is carried out by preparing an expression vector comprising an antigen-encoding nucleic acid, introducing the expression vector into appropriate host cells by gene transfer or genetic transformation, culturing the host cells under suitable conditions for expression of a recombinant protein, and recovering the recombinant protein expressed in the host cells.

The "vector" refers to a nucleic acid that can be used to introduce a nucleic acid attached thereto into host cells. The "expression vector" is a vector that can induce the expression of a protein encoded by a nucleic acid introduced thereby. Exemplary vectors include plasmid vectors, viral vectors, and the like. Those skilled in the art can select an appropriate expression vector for the expression of a recombinant protein depending on the type of host cells to be used. To facilitate purification, an affinity tags such as 6 His residues may be included. Moreover, a protein may be synthesized so that a signal sequence is included and the protein is secreted out of cells.

The "host cells" refers to cells that undergo gene transfer or genetic transformation by a vector. The host cells can be appropriately selected by those skilled in the art depending on the type of the vector to be used. The host cells can be derived from prokaryotes such as *Escherichia coli* (*E. coli*). When prokaryotic cells like *E. coli* are used as host cells, the antigen of the present invention may be designed to contain an N-terminal methionine residue in order to facilitate the expression of a recombinant protein in the prokaryotic cells. The N-terminal methionine can be cleaved from the recombinant protein after expression. Also, the host cells may be cells derived from eukaryotes, such as single-cell eukaryotes like yeast, plant cells and animal cells (e.g., human cells, monkey cells, hamster cells, rat cells, murine cells or insect cells) or silkworm.

Gene transfer or genetic transformation of an expression vector into host cells can be carried out as appropriate by following a technique known to those skilled in the art. Those skilled in the art can make possible the expression of a recombinant protein by selecting suitable conditions for the expression of the recombinant protein as appropriate depending on the type of host cells and culturing the host cells under the selected conditions. Then, those skilled in the art can homogenize the host cells having the expressed recombinant protein, and separate and purify an antigen expressed as the recombinant protein from the resulting homogenate by using an appropriate combination of such protein purification methods as mentioned above.

Diagnostic Kit and Method

The present invention provides a method for providing an indicator for diagnosing a fish allergy in a subject, the method comprising the steps of:

(i) contacting a sample obtained from the subject with an antigen, wherein the sample is a solution comprising an IgE antibody;

(ii) detecting binding between an IgE antibody present in the sample obtained from the subject and the antigen; and (iii) when the binding between the IgE antibody in the subject and the antigen is detected, an indicator of the fact that the subject has a fish allergy is provided;

wherein the antigen is at least one of the proteins identified as the aforementioned antigens (1) to (9) or at least one of the proteins identified as the aforementioned antigens (10) to (14).

The sample obtained from a subject is a solution containing an IgE antibody, as collected from the subject. Examples of such solutions include blood, saliva, sputum, snivel, urine, sweat, and tear. The sample obtained from the subject may be subjected to pretreatment for increasing the concentration of an IgE antibody in the sample before being contacted with an antigen. The pretreatment of a sample may involve, for example, collection of the serum and the plasma from the blood. Furthermore, Fab portions that are binding portions with the antigens may be purified. In a particularly preferred embodiment, the step (i) mentioned above is carried out by contacting an IgE antibody present in the serum obtained from a subject with an antigen.

The IgE antibody may be the IgE antibody itself or mast cells or the like to which the IgE antibody is bound.

Detection of contact and binding between the sample obtained from a subject and an antigen can be carried out by using a known method. Examples of such methods that can be used include detection by ELISA (Enzyme-Linked Immunosorvent Assay), sandwich immunoassay, immunoblotting, immunoprecipitation, or immunochromatography. These are all techniques involving contacting and binding an IgE antibody from a subject with an antigen and detecting the IgE antibody specifically bound to the antigen. Examples thereof include methods involving bringing an enzyme-labeled secondary antibody in contact, adding a substrate (usually a chromogenic or luminescent reagent) of the enzyme, and detecting the product of the enzymatic reaction; methods involving bringing a biotinylated secondary antibody in contact, adding an avidin-conjugated dye, and detecting the dye; and methods involving detecting a fluorescently labeled secondary antibody. Also, detection by a measurement method that permits the evaluation of binding between an antigen and an IgE antibody, such as surface plasmon resonance (SPR), can be used. A plurality of antigen-specific IgE antibodies may be mixed.

The antigen may be provided as an isolated antigen in a state immobilized on a carrier. In this case, the steps (i) and (ii) mentioned above can be carried out using ELISA, sandwich immunoassay, immunochromatography, surface plasmon resonance, or the like. Also, the step (i) mentioned above is carried out by contacting the sample obtained from a subject with an antigen-immobilized surface. The isolated antigen may be obtained by separating and purifying it from fish using a combination of protein purification methods well known to those skilled in the art, or by preparing it using a genetic recombination technique. Moreover, the antibody that binds to the antigen may be in an immobilized state.

The antigen may be in an unimmobilized state to a carrier. In this case, the steps (i) and (ii) mentioned above can be carried out by flow cytometry or the like and the presence of the antigen bound to an antibody may be confirmed using a laser beam. Examples include basophil activation test (BAT) in which an antigen binds to an antibody and the amount of the surface antigen CD203c which is expressed when basophils in the sample are activated is measured, and the like. Another example is histamine release test (HRT) in which it is examined whether histamine is released or not by bringing an antigen in contact with hemocytes via the binding to an antibody in a sample.

The antigen may be transferred from a state separated by two-dimensional electrophoresis and detected by immunoblotting. The two-dimensional electrophoresis is a technique for separating a protein sample by performing isoelectric focusing in the first dimension and performing SDS-PAGE (SDS-polyacrylamide gel electrophoresis) in the second dimension. The conditions for two-dimensional electrophoresis are not particularly limited as long as the conditions permit the separation of the antigen of the present invention. For example, the conditions for two-dimensional electrophoresis as described above in the subsection titled "Identification of antigens" can be adopted. Also, the electrophoresis conditions may be determined by reference to the descriptions in PTLs 1 to 4 mentioned above. For example, two-dimensional electrophoresis can be carried out under the conditions that satisfy at least one selected from the group consisting of the following requirements:

(A) the isoelectric focusing gels used in the first dimension should have a gel-strip length of 5 to 10 cm and a gel pH range of 3 to 10, and the pH gradient of the gels in the direction of electrophoresis should be as follows: where the gel-strip length up to pH 5 is taken as "a", that length from pH 5 to 7 as "b", and that length above pH 7 as "c", the relations "a<b" and "b>c" are satisfied;

(B) in the case of (A), when the total gel-strip length is taken as 1, "a" should be in the range of 0.15 to 0.3, "b" should be in the range of 0.4 to 0.7, and "c" should be in the range of 0.15 to 0.3;

(C) in the first dimensional isoelectric focusing, a constant voltage step should be performed by applying a constant voltage ranging from 100 V to 600 V per gel strip containing a sample, and after the electrophoresis variation width during electrophoresis for 30 minutes falls within the range of 5 μA, a voltage-increasing step should be started at which the voltage is increased from the aforementioned constant voltage;

(D) in the case of (C), the final voltage at the voltage-increasing step should be in the range of 3000 V to 6000 V;

(E) the isoelectric focusing gels used in the first dimension should have a longitudinal gel-strip length of 5 to 10 cm, and the electrophoresis gels used in the second dimension should have a gel concentration at the distal end in the direction of electrophoresis, which is in the range of 3 to 6%; and (F) in the case of (E), the electrophoresis gels used in the second dimension should have a gel concentration at the proximal end in the direction of electrophoresis, which is set to a higher value than that at the distal end in the direction of electrophoresis.

The aforementioned antigens (1) to (9) and the aforementioned antigens (10) to (14) are antigens which specifically bind to IgE antibodies in patients with an allergy to fish. Therefore, when binding between an IgE antibody from a subject and the antigen is detected, an indicator of the fact that the subject has a fish allergy is provided.

The present invention further provides a kit for diagnosing an allergy to a fish, comprising at least one of the aforementioned antigens (1) to (9) or at least one of the aforementioned antigens (10) to (14). The diagnostic kit of this invention may be used in the aforementioned method for providing an indicator for diagnosing an allergy to a fish or in a diagnostic method as described later. The diagnostic kit of this invention comprises at least one of the aforementioned antigens (1) to (9) or at least one of the aforementioned antigens (10) to (14) and may comprise a chromogenic substrate or luminescent substrate serving as a substrate of an enzyme-labeled anti-IgE antibody and the enzyme or a biotinylated anti-IgE antibody and an avidin-conjugated dye that binds to the biotin. Also, a fluorescent-labeled anti-IgE antibody may be used. In the diagnostic kit of this invention, the antigen may be provided in a state immobilized on a carrier. The diagnostic kit of this invention may also be provided together with instructions on the procedure for diagnosis or a package containing said instructions.

In another embodiment, the diagnostic kit comprises a companion diagnostic agent for an allergy to fish. The companion diagnostic agent is used to analyze the reactivity of a pharmaceutical product for the purpose of identifying a patient in which the pharmaceutical product is expected to work or a patient at risk for serious side effects from the pharmaceutical product, or optimizing a therapy using the pharmaceutical product. Here, examples of optimizing a therapy include determination of the dosage and administration, decision of stopping the administration, determination of the allergen component to be used for the induction of immune tolerance, and the like.

The present invention further provides a composition for diagnosing an allergy to a fish, comprising at least one of the aforementioned antigens (1) to (9) or at least one of the aforementioned antigens (10) to (14). The diagnostic composition of this invention can be used in a diagnostic method as described below. The diagnostic composition of this invention may further comprise a pharmaceutically acceptable carrier and/or additives commonly used with the antigen of this invention depending on the need.

In one embodiment, the present invention provides a method for diagnosing an allergy to a fish in a subject, the method comprising:

(i) contacting a sample obtained from the subject with an antigen;

(ii) detecting binding between an IgE antibody present in the sample obtained from the subject and the antigen; and (iii) when the binding between the IgE antibody in the subject and the antigen is detected, diagnosing the subject as being allergic to a fish;

wherein the antigen is at least one of the proteins identified as the aforementioned antigens (1) to (9) or at least one of the proteins identified as the aforementioned antigens (10) to (14). In this method, each of the steps (i) and (ii) is performed as described above regarding each of the corresponding steps of the method for providing an indicator for diagnosing an allergy to a fish.

In another embodiment, the present invention provides a method for diagnosing an allergy to a fish in a subject, the method comprising administering to the subject at least one of the aforementioned antigens (1) to (9) or at least one of the aforementioned antigens (10) to (14). This method may be performed in the form of a skin test characterized by applying the antigen onto the skin Examples of the skin test include various forms of tests, such as: a prick test in which a diagnostic composition is applied onto the skin and then a tiny prick to such an extent as not to provoke bleeding is made in the skin to allow an antigen to infiltrate into the skin, thereby observing a skin reaction; a scratch test in which a diagnostic composition is applied onto the skin and then the skin is lightly scratched to observe a reaction; a patch test in which a diagnostic composition in the form of cream, ointment, etc. is applied onto the skin to observe a reaction; and an intracutaneous test in which an antigen is administered intracutaneously to observe a reaction. The method for infiltrating a diagnostic composition into the skin in a prick test or a scratch test may be a method involving bringing a tip of a lancet in contact with a diagnostic composition and wounding the skin by pricking the skin with the contact site to infiltrate the composition. If a skin reaction such as swelling occurs in a skin portion to which the antigen has been applied, the subject of interest is diagnosed as having an allergy to a fish. The amount of the antigen to be applied to the skin in such tests can be, for example, not more than 100 μg per dose.

In the allergic diagnosis, a load test for the purpose of identifying the antigen is often performed. At least one of the aforementioned antigens (1) to (9) or at least one of the aforementioned antigens (10) to (14) may be used as an active ingredient of a load test for diagnosing an allergy to fish. Here, the antigen protein to be used in the load test may be a protein that has been expressed and purified and may be a protein that has been expressed in a food and a food material, for example, rice-based vaccine produced by transforming rice with a gene of a cedar pollen antigen to express the antigen protein therein.

In yet another embodiment, the present invention provides at least one of the aforementioned antigens (1) to (9) or at least one of the aforementioned antigens (10) to (14) for use in the diagnosis of an allergy to a fish. Here, the present invention encompasses the provision of at least one of the aforementioned antigens (1) to (9) or (10) to (14) mixed with a known antigen.

In still another embodiment, the present invention provides a use of at least one of the aforementioned antigens (1) to (9) or at least one of the aforementioned antigens (10) to (14) for the production of a diagnostic agent for an allergy to a fish.

Pharmaceutical Composition and Treatment Method

The present invention provides a pharmaceutical composition comprising at least one of the aforementioned antigens (1) to (9) or at least one of the aforementioned antigens (10) to (14).

In one embodiment, the aforementioned pharmaceutical composition is used for the treatment of an allergy to fish.

The present invention also provides a method for treating an allergy to fish, the method comprising administering at least one of the aforementioned antigens (1) to (9) or at least one of the aforementioned antigens (10) to (14) to a patient in need of a treatment for an allergy to a fish.

In another embodiment, the present invention provides at least one of the aforementioned antigens (1) to (9) or at least one of the aforementioned antigens (10) to (14) for use in the treatment of an allergy to fish. In yet another embodiment, the present invention provides use of at least one of the aforementioned antigens (1) to (9) or at least one of the aforementioned antigens (10) to (14) for the production of a therapeutic agent for an allergy to fish.

In the process of allergy treatment, a hyposensitization therapy aiming at inducing immunological tolerance by administering an antigen to a patient is often adopted. At least one of the aforementioned antigens (1) to (9) or at least one of the aforementioned antigens (10) to (14) can be used as an active ingredient for a hyposensitization therapy for allergy to fish. Here, the antigen protein to be used in the hyposensitization therapy may be a protein that has been expressed and purified and may be a protein that has been expressed in a food and a food material, for example, rice-based vaccine produced by transforming rice with a gene of a cedar pollen antigen to express the antigen protein therein.

The pharmaceutical composition of the present invention can be administered by common administration routes. Examples of common administration routes include oral, sublingual, percutaneous, intracutaneous, subcutaneous, intravascular, intranasal, intramuscular, intraperitoneal, and intrarectal administrations.

The pharmaceutical composition of the present invention can be used as a pharmaceutical composition to which a commonly used pharmaceutically acceptable adjuvant or excipient or any other additives (e.g., stabilizer, solubilizer, emulsifier, buffer, preservative, colorant) are added by a conventional method together with the antigen of this invention depending on the need. The dosage form of the pharmaceutical composition can be selected by those skilled in the art as appropriate depending on the administration route. The pharmaceutical composition can be in the form of, for example, tablet, capsule, troche, sublingual tablet, parenteral injection, intranasal spray, poultice, solution, cream, lotion, or suppository. The administration dose, frequency and/or period of the pharmaceutical composition of this invention can be selected by a physician as appropriate depending on the administration route and the patient's condition and characteristics such as age and body weight. For example, the pharmaceutical composition may be administered to an adult patient at a dose of not more than 100 μg per dose. The administration interval can be, for example, once daily, once weekly, twice monthly, once per three months or so. The administration period can be, for example, several weeks to several years. The pharmaceutical composition may be administered in such a manner that the dose is increased in incremental steps over the administration period.

Tester

The present invention provides a tester comprising an antibody for at least one of the aforementioned antigens (1) to (9) or at least one of the aforementioned antigens (10) to (14).

The antibody can be prepared by a conventional method. For example, the antibody may be prepared by immunizing a mammal such as rabbit with one of the aforementioned antigens (1) to (9) or one of the aforementioned antigens (10) to (14). The antibody may be an IgE antibody, a polyclonal antibody, a monoclonal antibody, or an antigen-binding fragment thereof (e.g., Fab, F(ab')2, Fab').

Further, in the aforementioned tester, the antibody may be provided in a form bound to a carrier. The type of the carrier is not particularly limited as long as it is usable for detection of binding between an antibody and an antigen. Any given carrier known to those skilled in the art can be used.

Examples of a method for determining the presence or absence of an antigen include:

A method in which a prepared tester comprising an IgE antibody is contacted with a sample obtained from a food or food material, and ELISA or the like method is, for example, used to detect whether there is a binding between the IgE antibody and an antigen in the sample, and if the binding between the IgE antibody and the antigen is detected, it is determined that the antibody remains in the food or food material, of interest.

A method in which proteins are extracted from a food or food material, and the proteins are subjected to electrophoresis, and it is detected with an antibody whether there is a spot band of the antigen.

A method in which a food or food material is infiltrated into a filter paper or the like and an antibody solution is reacted with the filter paper to detect an antigen present in the food.

The present invention encompasses, in another embodiment, a tester for determining the presence or absence of an antigen for an allergy to fish in an object of interest, the tester comprising a primer having a nucleotide sequence complementary to at least one part of one of the nucleotide sequences set forth in SEQ ID NO: 1, 4, 9, 18, 25, 32, 42, 55, 60, 69, 109, 120, 137, or 143. Without limiting, the primer has a nucleotide sequence complementary to preferably 12 residues, 15 nucleotides, 20 nucleotides, or 25 nucleotides in the sequence of a 3' terminal or middle portion of at least one part of one sequence of the nucleotide sequences set forth in, for example, SEQ ID NO: 1, 4, 9, 18, 25, 32, 42, 55, 60, 69, 109, 120, 137, or 143. Particularly when mRNA is targeted, the tester comprises a poly A tail-complementarity primer. In a preferred embodiment, the tester comprising the primer may further comprise a primer comprising a nucleotide sequence of a 5' terminal portion of at least one sequence of the nucleotide sequences set forth in SEQ ID NO: 1, 4, 9, 18, 25, 32, 42, 55, 60, 69, 109, 120, 137, or 143, preferably a nucleotide sequence consisting of 12 nucleotides, 15 nucleotides, 20 nucleotides, 25 nucleotides.

For example, the presence or absence of the antigen is determined by amplifying DNA or cDNA by polymerase chain reaction (PCR) including RT-PCR by using the aforementioned primer with DNA or mRNA obtained from fish as a template and comparing the amplified DNA or cDNA sequence(s) with SEQ ID NO: 1, 4, 9, 18, 25, 32, 42, 55, 60, 69, 109, 120, 137, or 143. Examples of the method of the amplification of mRNA by PCR include RACE and the like. In the determination, the antigen is determined to be present when the comparison between the amplified DNA or cDNA and SEQ ID NO: 1, 4, 9, 18, 25, 32, 42, 55, 60, 69, 109, 120, 137, or 143 indicates the presence of point mutation(s) encoding the same amino acid(s), or when the amino acid sequence encoded by the amplified DNA or cDNA has 70% or more, preferably 80, 90, 95, 98, or 99% or more identity with an amino acid sequence of SEQ ID NO: 2, 5, 10, 19, 26, 33, 43, 56, 61, 70, 110, 121, 138, or 144, even if the nucleotide sequence of the amplified DNA or cDNA is modified from any of the nucleotide sequences of SEQ ID NO: 1, 4, 9, 18, 25, 32, 42, 55, 60, 69, 109, 120, 137, or 143 by insertion, deletion, substitution, or addition of nucleotide(s).

In one embodiment, the aforementioned tester is used to determine the presence or absence of an antigen in food materials (fish or fish eggs) or in products of interest in a food production line. The tester may also be used for quality inspection of production lines and pre-shipment products by manufacturers, or may be used for self-checking of the presence or absence of an antigen in a food or food material of interest by consumers.

Allergen-Free Food and the Like

The present invention provides fish or fish eggs in which at least one of the aforementioned antigens (1) to (9) or at least one of the aforementioned antigens (10) to (14) is eliminated or reduced, a processed product of the fish or the fish eggs or fish which lay the fish eggs or have hatched from the eggs.

The method for eliminating or reducing the antigen of the present invention in fish, fish eggs, the processed product of the fish or the fish eggs or the fish which lay the fish eggs or have hatched from the eggs is not limited. The elimination or reduction of the antigen of the present invention may be conducted by any method, as long as the method permits the elimination or reduction of the antigen.

For example, the fish or fish eggs in which the antigen of the present invention is eliminated or reduced may be obtained by preparing fish or fish eggs in which the expression of the antigen of the present invention is knocked out, using a gene knock-out technique.

As the gene knock-out technique, there can be used any methods known to those skilled in the art. For example, Oishi, et al. (Scientific Reports, Vol. 6, Article number: 23980, 2016, doi:10.1038/srep23980) describes that the genome editing technique CRISPER/Cas9 is applied to primordial germ cells to obtain individual animals deficient in an allergen gene. The fish or fish eggs devoid of the antigen of this invention may also be obtained by using the same technique. Moreover, fish or fish eggs in which the antigen of the present invention is eliminated or reduced may be obtained by mating by artificial insemination with fish or fish eggs that do not contain the antigen or contains a low content of the antigen. The artificial mating of fish or fish eggs can be performed by a conventional method.

The processed product of the fish or fish eggs in which the antigen of the present invention is eliminated or reduced may be a processed product made from fish in which the antigen of the present invention is eliminated or reduced. In the case of using ordinary fish or fish eggs as a source ingredient, a treatment for removing or reducing the antigen of the present invention is performed before or after preparation of a processed product of fish or fish eggs. Examples of a method of eliminating or reducing the antigen of the present invention in a processed product of fish or fish eggs made from ordinary fish or fish eggs include methods for eliminating the protein component in a food or a food material, such as elution with a high pressure treatment and a neutral salt solution and hot steam and methods for hydrolysis, denaturation, or amino acid modification (chemical modification or elimination of side chains) by heat treatment and acid treatment. The fish in which the antigen of the present invention is eliminated or reduced may be fish that have hatched and grown from the aforementioned fish eggs in which the antigen of the present invention is eliminated or reduced. Moreover, the fish eggs in which the antigen of the present invention is eliminated or reduced may be those obtained from the aforementioned fish in which the antigen of the present invention is eliminated or reduced.

EXAMPLES

The following describes examples of the present invention. The technical scope of this invention is not limited by these examples.

Example 1: Confirmation of a Protein Pattern

Proteins contained in salmon were investigated using a two-dimensional electrophoresis method described below.

Protein Extraction

The extraction and the purification of proteins contained in salmon were performed as follows. A solubilization agent (Mammalian Lysis Buffer (MCLI), SIGMA) was added to flesh of salmon and proteins were extracted, and then a urea buffer was added to obtain a protein extract. The composition of the urea buffer is as follows.

30 mM Tris

2 M Thiourea

7 M Urea

4% (w/v) CHAPS:

3-[(3-cholamidopropyl)dimethylammonio]propanesulfonate

Moderate Amount of Dilute Hydrochloric Acid

Distilled water was added and the total volume was adjusted to 100 mL. pH was 8.5.

Subsequently, 25 μg each in terms of protein weight was mixed to obtain an extract.

Thereafter, the precipitation procedure was repeated twice using a 2D-CleanUP Kit (produced by GE). In the first round of precipitation, the collected liquid protein extract was precipitated by adding TCA (trichloroacetic acid) thereto and the precipitated product produced by this procedure (TCA-precipitated product) was collected. In the second round of precipitation, the TCA-precipitated product collected above was further precipitated by adding acetone thereto and the precipitated product (sample) produced by this procedure was collected.

Preparation of a Sample Solution

Part of the collected sample (40 μg on a protein weight basis) was dissolved in 150 μL of a DeStreak Rehydration Solution (produced by GE), which is a swelling buffer for first-dimensional isoelectric focusing gels, thereby obtaining a sample solution for first-dimensional isoelectric focusing (sample solution for swelling). The constituents of the DeStreak Rehydration Solution are as mentioned below.

7M thiourea 2M urea

4% (w/v) of CHAPS 0.5% (v/v) IPG buffer; produced by GE

Moderate amount of BPB (bromophenol blue)

Impregnation of the Sample into First-Dimensional Isoelectric Focusing Gels

First-dimensional isoelectric focusing gel strips (Immobiline Drystrip IPG gels (pH3-10NL); produced by GE) were immersed in 140 μL of the foregoing sample solution for first-dimensional isoelectric focusing (sample solution for swelling) and impregnated with the solution at room temperature overnight.

In this example, an IPGphor electrophoresis system produced by GE was used.

An electrophoresis tray was filled with silicone oil. Filter paper moisten with water was positioned at both ends of the gel strips impregnated with the sample, and the gel strips were set in the electrophoresis tray such that the gel strips were covered with silicone oil. Electrodes were placed on the gel strips with the filter paper intervening therebetween.

The maximum current of the isoelectric focusing system was set to 75 μA per gel strip, and the first-dimensional isoelectric focusing was carried out according to the following voltage program: (1) a constant voltage step was performed at a constant voltage of 300 V until the volt-hours reached 750 Vhr (the current variation width during electrophoresis for 30 minutes before the end of this step was 5 μA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

SDS Equilibration of Isoelectric Focusing Gels

After the aforementioned first-dimensional isoelectric focusing was done, the gel strips were taken out of the isoelectric focusing system, immersed in an equilibration buffer containing a reducing agent, and shaken at room temperature for 15 minutes. The constituents of the equilibration buffer containing the reducing agent are as mentioned below.

100 mM Tris-HCl (pH 8.0)

6M urea

30% (v/v) glycerol

2% (w/v) SDS

1% (w/v) DTT

Next, the equilibration buffer containing the reducing agent was removed, and then the gel strips were immersed in an equilibration buffer containing an alkylating agent and shaken at room temperature for 15 minutes to obtain SDS-equilibrated gels. The constituents of the equilibration buffer containing the alkylating agent are as mentioned below.

100 mM Tris-HCl (pH 8.0)

6M urea

30% (v/v) glycerol

2% (w/v) SDS 2.5% (w/v) iodoacetamide

Second-Dimensional SDS-PAGE

In this example, the XCell SureLock Mini-Cell electrophoresis system produced by Life Technologies was used. The second-dimensional electrophoresis gels used were NuPAGE 4-12% Bis-Tris Gels produced by Life Technologies. Also, an electrophoresis buffer composed of the following constituents was prepared and used.

50 mM MOPS 50 mM Tris base 0.1% (w/v) SDS 1 mM EDTA

Further, an agarose solution for gel adhesion was used in this example, which was prepared by dissolving 0.5% (w/v) Agarose S (produced by Nippon Gene Co., Ltd.) and a moderate amount of BPB (bromophenol blue) in the electrophoresis buffer.

SDS-PAGE wells were washed well with the electrophoresis buffer, and then the buffer used for the washing was removed. Next, the washed wells were charged with the fully dissolved agarose solution for gel adhesion. Next, the SDS-equilibrated gel strips were immersed in agarose and closely adhered to second-dimensional electrophoresis gels using tweezers. After it was confirmed that agarose was fully fixed with the gels being closely adhered to each other, electrophoresis was performed at a constant voltage of 200 V for about 45 minutes.

Fluorescent Staining of Gels

The gels were fluorescently stained with SYPRO Ruby (produced by Life Technologies).

First, an airtight container to be used was washed well in advance with 98% (v/v) ethanol. The electrophoresed second-dimensional electrophoresis gel strips were taken out of the SDS-PAGE system, placed onto the washed airtight container, and treated twice by immersion in 50% (v/v) methanol and 7% (v/v) aqueous solution containing acetic acid for 30 minutes. Then, a further immersion treatment was done for 10 minutes, with the solution being replaced by water. Next, the second-dimensional electrophoresis gel strips were immersed in 40 mL of SYPRO Ruby and shaken at room temperature overnight.

Thereafter, the SYPRO Ruby was removed, and then the second-dimensional electrophoresis gel strips were washed with water and shaken in 10% (v/v) methanol and 7% (v/v) aqueous solution containing acetic acid for 30 minutes. Further shaking was done for at least 30 minutes, with the solution being replaced by water.

Analysis

The second-dimensional electrophoresis gels obtained through the foregoing series of treatments were subjected to fluorescent image scanning on Typhoon 9500 (produced by GE). The left panel of FIG. 1A illustrates the result of two-dimensional electrophoresis of proteins contained in flesh of salmon. Molecular weight marker bands are found at the left of the panels. The positions of the bands indicate particular molecular weights (KDa).

Example 2: Identification of Antigens by Immunoblotting (1)

Identification of antigens by immunoblotting was carried out by taking all the steps up to the step of "Second-dimensional SDS-PAGE" as described above in Example 1, followed by the steps of "Transfer to membrane", "Immunoblotting" and "Analysis" as described below.

Transfer to Membrane

Transfer to membrane was done using the following transfer system and transfer buffer.

Transfer system: XCell SureLock Mini-Cell and XCell II Blot Module (produced by Life Technologies)

Transfer buffer: NuPAGE Transfer Buffer (×20) (produced by Life Technologies), used in a form diluted 20-fold with milliQ water.

To be specific, proteins in the second-dimensional electrophoresis gels were transferred to a membrane (PVDF membrane) according to the following procedure.

(1) The PVDF membrane was immersed in 100% methanol followed by milliQ water, and then moved into the transfer buffer to hydrophilize the PVDF membrane.

(2) After sponge, filter paper, the second-dimensional electrophoresis gels prepared by second-dimensional SDS-PAGE, the hydrophilized PVDF membrane, filter paper, and sponge were put in place in this order, the transfer system was energized at a constant voltage of 30 V for one hour.

Immunoblotting

Immunoblotting of the membrane was carried out using, as a primary antibody, a serum sample from a patient 1 with a fish allergy or a serum sample from a non-fish-allergic subject. This Fish-allergic patient 1 is a patient diagnosed as immediate-type allergy to fish. This patient developed allergic symptoms to salmon, horse mackerel, sea eel, black porgy, mackerel, sea bream, cod, and young yellowtail and was positive in a prick test.

Immunoblotting of the membrane was carried out according to the following procedure.

(1) The transferred membrane was shaken in a 5% skim milk/PB ST solution (a PBS buffer containing 0.1% Tween 20 nonionic surfactant) at room temperature for one hour.

(2) The membrane was left to stand in a solution of 5% serum as a primary antibody in 5% skim milk/PBST at room temperature for one hour.

(3) The membrane was washed with a PBST solution (5 min×3 times).

(4) The membrane was left to stand in a solution of 1:5000 dilution of the secondary antibody, anti-human IgE-HRP (horseradish peroxidase), with a 5% skim milk/PBST solution at room temperature for one hour.

(5) The membrane was washed with a PBST solution (5 min×3 times).

(6) The membrane was left to stand in Pierce Western Blotting Substrate Plus (produced by Thermo Fisher Scientific) for 5 minutes.

Analysis

The membrane obtained through the foregoing series of treatments was subjected to fluorescent image scanning on Typhoon 9500 (produced by GE).

Figure 3:
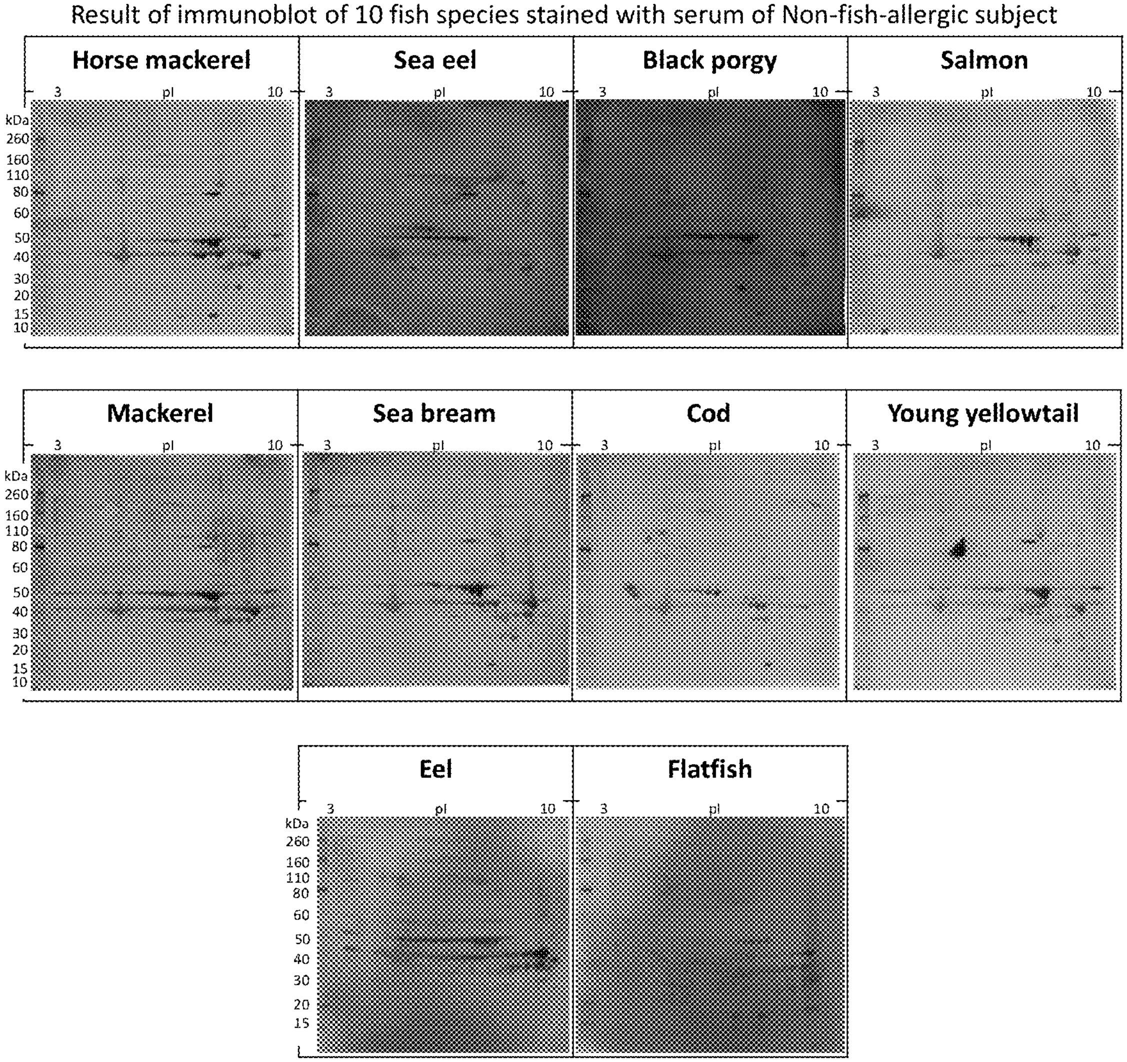
FIG. 3 is photographs of immunoblots obtained from two-dimensional electrophoretic patterns of proteins contained in extracts of the flesh of 10 species of fish stained with serum of a subject who does not exhibit fish allergic symptoms (Non-fish-allergic subject).

The immunoblot obtained with the serum from Fish-allergic patient 1 was compared with that obtained with the control serum from Non-fish-allergic subject. Nine spots that are different from those with the serum of Non-fish-allergic subject (FIG. 3) and different from the known salmon allergen proteins were detected on an immunoblot of the proteins contained in flesh of salmon with the serum of Fish-allergic patient 1 (FIG. 1A, right panel). The detected spots are indicated in the immunoblot (FIG. 1A, right panel).

The molecular weights and isoelectric points of the 9 spots are as follows.

Spot 1: Molecular weight 90 to 120 kDa, pI 3.0 to 6.0
Spot 2: Molecular weight 120 to 160 kDa, pI 4.0 to 7.0
Spot 3: Molecular weight 90 to 120 kDa, pI 5.0 to 8.0
Spot 4: Molecular weight 90 to 120 kDa, pI 6.0 to 8.0
Spot 5: Molecular weight 60 to 90 kDa, pI 3.0 to 6.0
Spot 6: Molecular weight 70 to 100 kDa, pI 5.0 to 7.0
Spot 7: Molecular weight 40 to 70 kDa, pI 4.0 to 7.0
Spot 8: Molecular weight 40 to 70 kDa, pI 4.0 to 7.0
Spot 9: Molecular weight 20 to 50 kDa, pI 4.0 to 7.0

Example 3: Mass Spectrometry and Identification of Antigens (1)

The amino acid sequences of the antigens that form the above nine protein spots were identified by mass spectroscopy.

To be specific, protein extraction and mass spectroscopy were done by the following procedure.

(1) Flesh of salmon was subjected to protein extraction, two-dimensional electrophoresis and transfer to membrane by following the procedures described in Example 1 and 2, and the resulting membrane was stained by shaking in a solution of 0.008% Direct blue in 40% ethanol and 10% acetic acid.

(2) Then, the membrane was decolorized by repeating a 5-minute treatment with 40% ethanol and 10% acetic acid three times, washed with water for 5 minutes, and then dried by air.

(3) A protein spot of interest was cut out with a clean cutter blade and put into a centrifugal tube. The cut membrane was subjected to hydrophilization with 50 μL of methanol, followed by washing with 100 μL of water twice and then centrifugal cleaning. Thereafter, 20 μL of 20 mM $NH_4HCO_3$ and 50% acetonitrile were added.

(4) 1 μL of 1 μmol/μL lysyl endopeptidase (produced by WAKO) was added, and the solution was left to stand at 37° C. for 60 minutes and then collected in a new centrifugal tube. After 20 μL of 20 mM $NH_4HCO_3$ and 70% acetonitrile were added to the membrane, the membrane was immersed therein at room temperature for 10 minutes, and the resulting solution was further collected. The solution was dissolved with 0.1% formic acid and 10 μL of 4% acetonitrile and transferred to a tube.

(5) The collected solution was dried under reduced pressure, dissolved with 15 μL of solution A (a 0.1% formic acid/4% acetonitrile solution), and analyzed by mass spectroscopy (ESI-TOF6600, produced by AB Sciex).

(6) Identification of proteins based on the MS data obtained with the mass spectrometer was done by searching NCBI or UniProt.

Results

The mass spectrometry of the spots resulted in the detection of the following amino acid sequences.

Spot 1: the amino acid sequences set forth in SEQ ID NO: 3

Spot 2: the amino acid sequences set forth in SEQ ID NO: 6 to 8

Spot 3: the amino acid sequences set forth in SEQ ID NO: 11 to 17

Spot 4: the amino acid sequences set forth in SEQ ID NO: 20 to 24

Spot 5: the amino acid sequences set forth in SEQ ID NO: 27 to 31

Spot 6: the amino acid sequences set forth in SEQ ID NO: 34 to 41

Spot 7: the amino acid sequences set forth in SEQ ID NO: 44 to 54

Spot 8: the amino acid sequences set forth in SEQ ID NO: 57 to 59

Spot 9: the amino acid sequences set forth in SEQ ID NO: 62 to 68

Furthermore, the spots were identified as the following proteins by the analysis of the MS data obtained from the mass spectrometer for spot 1 at NCBI and for spots 2 to 9 with UniProt.

Spot 1: Alpha-actinin-3 (NCBI protein accession number XP_014051545.1, DNA accession number XM_014196070.1) (amino acid sequence: SEQ ID NO: 2, encoding nucleotide sequence: SEQ ID NO: 1)

Spot 2: EEF1A2 binding protein-like (UniProt protein accession number B5RI29, DNA accession number ACH85270.1) (amino acid sequence: SEQ ID NO: 5, encoding nucleotide sequence: SEQ ID NO: 4)

Spot 3: Alpha-1,4-glucan phosphorylase (UniProt protein accession number B5DG55, DNA accession number ACH70729.1) (amino acid sequence: SEQ ID NO: 10, encoding nucleotide sequence: SEQ ID NO: 9)

Spot 4: Elongation factor 2 (UniProt protein accession number C0H9N2, DNA accession number ACN10751.1) (amino acid sequence: SEQ ID NO: 19, encoding nucleotide sequence: SEQ ID NO: 18)

Spot 5: Heat shock cognate 70 kDa protein (UniProt protein accession number B5X3U6, DNA accession number ACI33977.1) (amino acid sequence: SEQ ID NO: 26, encoding nucleotide sequence: SEQ ID NO: 25)

Spot 6: Serotransferrin (UniProt protein accession number P79815, DNA accession number BAA13759.1) (amino acid sequence: SEQ ID NO: 33, encoding nucleotide sequence: SEQ ID NO: 32)

Spot 7: Myosin binding protein H-like (UniProt protein accession number B5DG45, DNA accession number ACH70719.1) (amino acid sequence: SEQ ID NO: 43, encoding nucleotide sequence: SEQ ID NO: 42)

Spot 8: Desmin (Fragment) (UniProt protein accession number Q8UWF1, DNA accession number CAC83053.1) (amino acid sequence: SEQ ID NO: 56, encoding nucleotide sequence: SEQ ID NO: 55)

Spot 9: Capping protein (Actin filament) muscle Z-line beta (UniProt protein accession number B5DFX6, DNA accession number ACH70650.1) (amino acid sequence: SEQ ID NO: 61, encoding nucleotide sequence: SEQ ID NO: 60)

Example 4: Confirmation of Antigens in Other Fish Species (1)

Using flesh of the 9 fish species, horse mackerel, sea eel, black porgy, mackerel, sea bream, cod, young yellowtail, eel, and flatfish, other than salmon, antigens were confirmed by the same procedure as the procedure described in Example 1 and Example 2.

Figure 2:
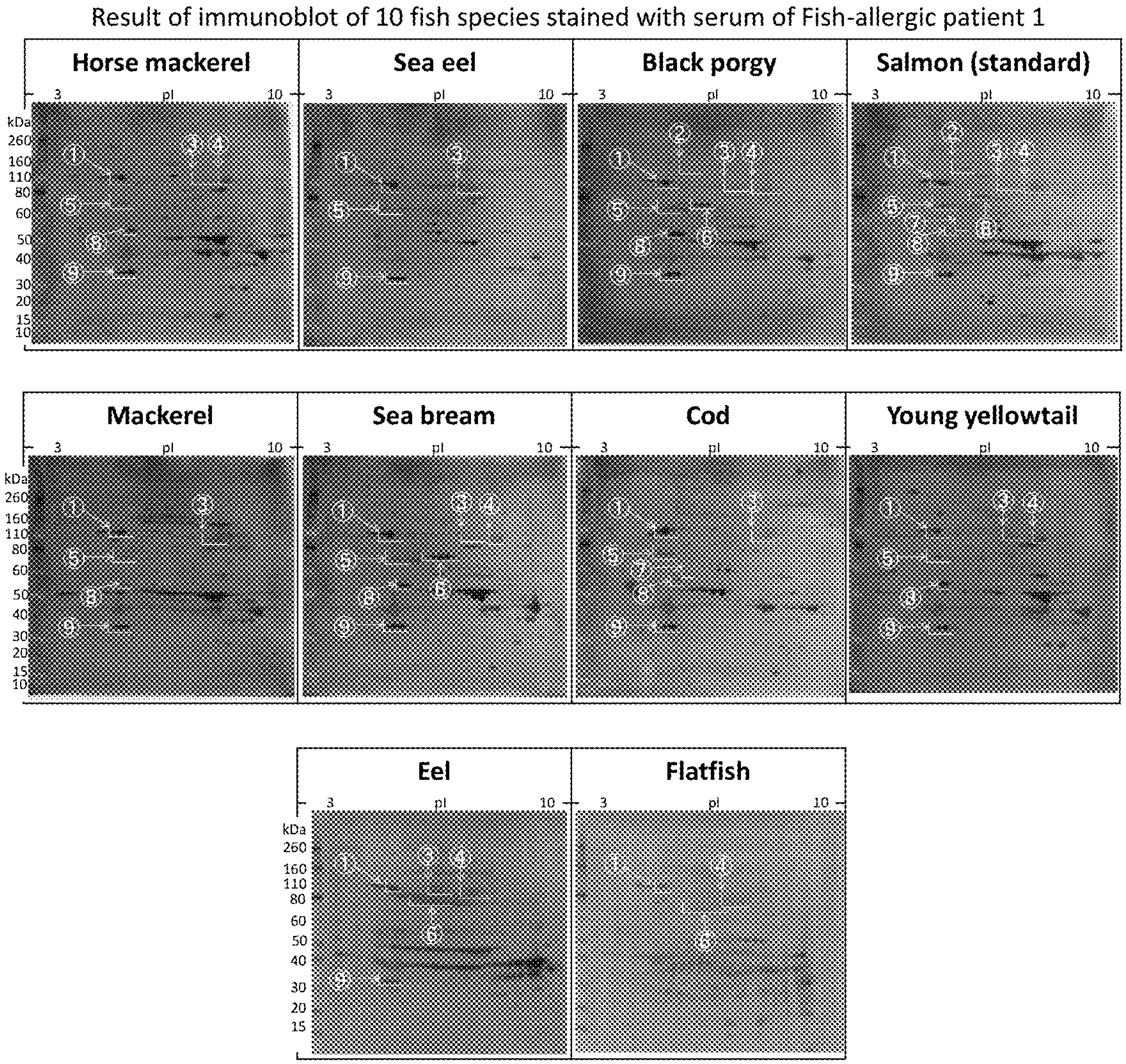
FIG. 2 is photographs of immunoblots obtained from two-dimensional electrophoretic patterns of proteins contained in extracts of the flesh of 10 species of fish stained with serum of Fish-allergic patient 1.

Immunoblots obtained with the serum from Fish-allergic patient 1 was compared with that obtained with the control serum from Non-fish-allergic subject. Spots that are different from those with the serum from Non-fish-allergic subject (FIG. 3) and correspond to a part of the 9 spots obtained in salmon were detected on immunoblots (FIG. 2) of proteins contained in flesh of each of the 9 fish species stained with the serum from Fish-allergic patient 1.

Spots detected in each fish species are as follows.

Horse mackerel: Spots 1, 3-5, 8, and 9

Sea eel: Spots 1, 3, 5, and 9

Black porgy: Spots 1-6, 8, and 9

Mackerel: Spots 1, 3, 5, 8, and 9

Sea bream: Spots 1, 3-6, 8, and 9

Cod: Spots 1, 3, 5, 7-9

Young yellowtail: Spots 1, 3-5, 8, 9

Eel: Spots 1, 3, 4, 6, 9

Flatfish: Spots 1, 4, 6

Example 5: Confirmation of Antigens by Immunoblotting (2)

An immunoblot obtained with serum from a fish-allergic patient was compared with that obtained with the control serum from Non-fish-allergic subject in the same way as in Example 2. Three new spots (Spots 11, 12, 14) that are different from those with the serum from Non-fish-allergic subject (FIG. 3) and different from the known salmon allergen proteins, other than 7 (spots 1-6, 9) of the 9 spots detected in Example 2, were detected on an immunoblot (FIG. 1B, left panel) of proteins contained in flesh of salmon stained with the serum from Fish-allergic patient 2. The total 10 spots detected are indicated in the immunoblot (FIG. 1B, left panel).

The molecular weights and isoelectric points of the 3 new spots detected are as follows.

Spot 11: Molecular weight 90 to 110, pI 6.5 to 7.0

Spot 12: Molecular weight 120 to 140, pI 5.0 to 6.0

Spot 14: Molecular weight 30 to 40, pI 6.5 to 7.5

Example 6: Mass Spectrometry and Identification of Antigens (2)

The amino acid sequences of the antigens that form the 3 spots newly detected were identified by mass spectroscopy in the same way as in Example 3.

The mass spectrometry of the spots resulted in the detection of the following amino acid sequences.

Spot 11: Amino acid sequences set forth in SEQ ID NOs: 111 to 119

Spot 12: Amino acid sequences set forth in SEQ ID NOs: 122 to 136

Spot 14: Amino acid sequences set forth in SEQ ID NOs: 145 to 149

Furthermore, the spots were identified as the following proteins by the analysis of the MS data obtained from the mass spectrometer for the spots at NCBI.

Spot 11: Glycogen phosphorylase, muscle form-like (NCBI protein accession number XP_013984904.1, DNA accession number XM_014129429.1) (amino acid sequence: SEQ ID NO: 110, encoding nucleotide sequence: SEQ ID NO: 109)

Spot 12: Myosin-binding protein C, fast-type-like (NCBI protein accession number XP_014014310.1, DNA accession number XM_014158835.1) (amino acid sequence: SEQ ID NO: 121, encoding nucleotide sequence: SEQ ID NO: 120)

Spot 14: L-lactate dehydrogenase A chain-like (NCBI protein accession number XP_014003141.1, DNA accession number XM_014147666.1) (amino acid sequence: SEQ ID NO: 144, encoding nucleotide sequence: SEQ ID NO: 143)

Example 7: Confirmation of Antigens by Immunoblotting (3)

An immunoblot obtained with the serum from a fish-allergic patient was compared with that obtained with the control serum from Non-fish-allergic subject, in the same way as in Example 2. Two new spots (Spots 10, 13) that are different from those with the serum from Non-fish-allergic subject (FIG. 3) and different from the known salmon allergen proteins, other than 2 (Spots 7, 8) of the 9 spots detected in Example 2, were detected on an immunoblot (FIG. 1B, right panel) of proteins contained in flesh of salmon stained with the serum from Fish-allergic patient 3. The total 4 spots detected are indicated in the immunoblot (FIG. 1B, right panel).

The molecular weights and isoelectric points of the 2 new spots detected are as follows.

Spot 10: Molecular weight 200 to 230, pI 4.5 to 5.5

Spot 13: Molecular weight 45 to 55, pI 4.0 to 5.5

Example 8: Mass Spectrometry and Identification of Antigens (3)

The amino acid sequences of the antigens that form the 2 spots newly detected were identified by mass spectroscopy in the same way as in Example 3.

The mass spectrometry of the spots resulted in the detection of the following amino acid sequences.

Spot 10: Amino acid sequences set forth in SEQ ID NOs: 71 to 108

Spot 13: Amino acid sequences set forth in SEQ ID NOs: 139 to 142

Furthermore, the spots were identified as the following proteins by the analysis of the MS data obtained from the mass spectrometer for the spots at NCBI.

Spot 10: Myosin heavy chain, fast skeletal muscle-like (NCBI protein accession number XP_014039990.1, DNA accession number XM_014184515.1) (amino acid sequence: SEQ ID NO: 70, encoding nucleotide sequence: SEQ ID NO: 69)

Spot 13: ATP synthase subunit beta, mitochondrial (NCBI protein accession number XP_014007238.1, DNA accession number XM_014151763.1) (amino acid sequence: SEQ ID NO: 138, encoding nucleotide sequence: SEQ ID NO: 137)

Example 9: Confirmation of Antigens in Other Fish Species (2)

Figure 4:
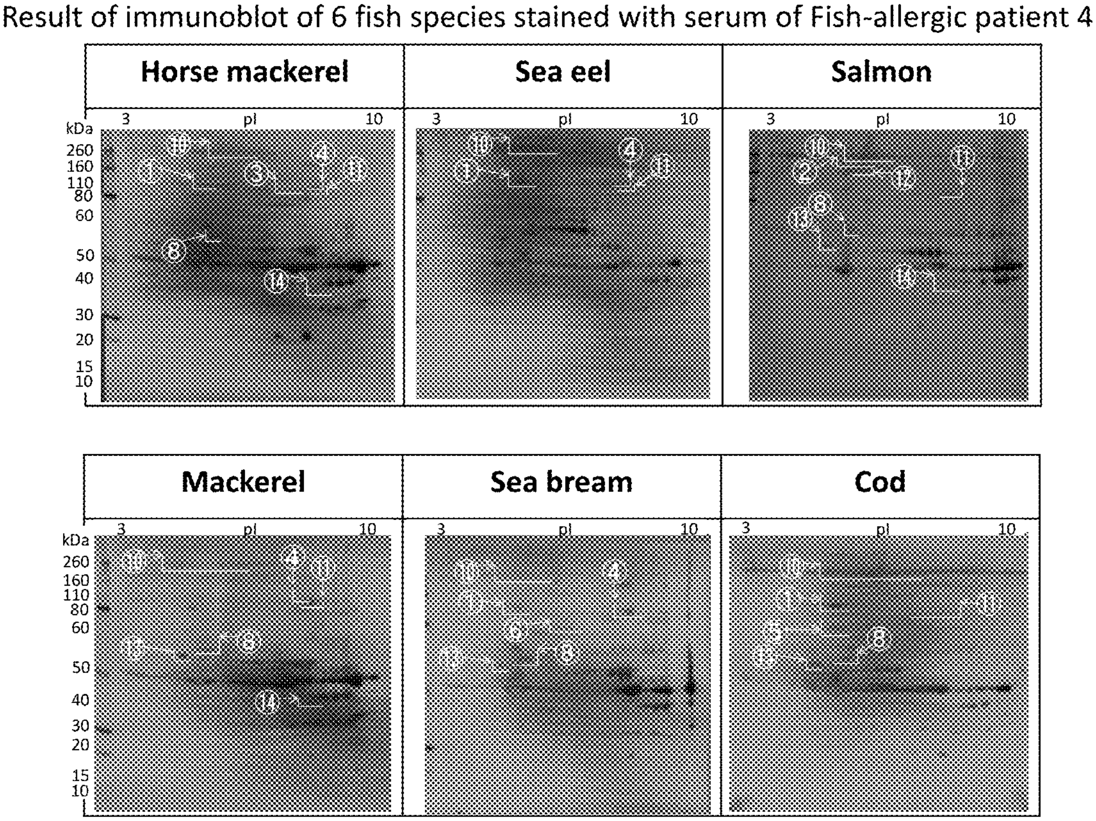
FIG. 4 is photographs of immunoblots obtained from two-dimensional electrophoretic patterns of proteins contained in extracts of the fish of 6 species of fish by using a serum of Fish-allergic patient 4.

Using flesh of the 6 fish species, horse mackerel, sea eel, salmon, mackerel, sea bream, and cod, the antigen was confirmed in the same way as in Example 4. Immunoblots obtained with the serum from Fish-allergic patient 4 was compared with that obtained with the control serum from Non-fish-allergic subject. Spots that are different from those with the serum from Non-fish-allergic subject (FIG. 3) and correspond to a part of the 14 spots obtained in salmon with the serum from Fish-allergic patients 1 to 3 were detected on immunoblots (FIG. 4) of proteins contained in flesh of each of the 6 fish species stained with the serum from Fish-allergic patient 4.

Spots detected in each fish species are as follows.

Horse mackerel: Spots 1, 3, 4, 8, 10, 11, and 14

Sea eel: Spots 1, 4, 10, and 11

Salmon: Spots 2, 8, and 10-14

Mackerel: Spots 4, 8, 10, 11, 13, and 14

Sea bream: Spots 1, 4, 6, 8, 10, and 13

Cod: Spots 1, 5, 8, 10, 11, and 13

INDUSTRIAL APPLICABILITY

The present invention can provide novel antigens of an allergy to fish, methods and kits for diagnosing an allergy to fish, a pharmaceutical composition comprising the antigen, and fish or fish eggs in which the antigen is eliminated or reduced, a processed product of the fish or fish eggs, or fish which lay the fish eggs or have hatched from the eggs. The present invention can further provide a tester for determining the presence or absence of a fish antigen in an object of interest.

The invention claimed is:

1. A method for detecting binding between an antigen and an IgE antibody present in a sample, comprising contacting the antigen with the IgE antibody, wherein the antigen is isolated and immobilized to a carrier or a surface and defined as: an Alpha-actinin-3 protein or a variant thereof, wherein said Alpha-actinin-3 protein or variant thereof is capable of binding specifically to an IgE antibody of a patient with an allergy to fish, and is defined below in any of (a) to (d):

(a) comprising the amino acid sequence of SEQ ID NO: 2, with or without a conserved amino acid substitution of a residue of SEQ ID NO: 2;

(b) having 100% identity to the full-length amino acid sequence of SEQ ID NO: 2;

(c) comprising an amino acid sequence encoded by a nucleotide sequence having 100% identity to the nucleotide sequence of SEQ ID NO: 1; or (d) encoded by a nucleic acid that hybridizes over its full length under high stringent conditions of 0.1×SSC to 2×SSC hybridization at 55° C. to 65° C. and/or 0.2×SSC to 2×SSC washing at 50° C. to 68° C., with the nucleic acid complementary to the nucleotide sequence of SEQ ID NO: 1.

2. A method for detecting binding between an antigen and an IgE antibody present in a sample, comprising contacting the antigen with the IgE antibody, wherein the antigen is isolated and immobilized to a carrier or a surface and defined as a Heat shock cognate 70 kDa protein or a variant thereof, wherein said Heat shock cognate 70 kDa protein or variant thereof is capable of binding specifically to an IgE antibody of a patient with an allergy to fish, and is defined below in any of (a) to (d):

(a) comprising the amino acid sequence of SEQ ID NO: 26, with or without a conserved amino acid substitution of a residue of SEQ ID NO: 26;

(b) having 100% identity to the full-length amino acid sequence of SEQ ID NO: 26;

(c) comprising an amino acid sequence encoded by a nucleotide sequence having 100% identity to the nucleotide sequence of SEQ ID NO: 25; or (d) encoded by a nucleic acid that hybridizes over its full length under high stringent conditions of 0.1×SSC to 2×SSC hybridization at 55° C. to 65° C. and/or 0.2×SSC to 2×SSC washing at 50° C. to 68° C., with the nucleic acid complementary to the nucleotide sequence of SEQ ID NO: 25.

3. A method for detecting binding between an antigen and an IgE antibody present in a sample, comprising contacting the antigen with the IgE antibody, wherein the antigen is isolated and immobilized to a carrier or a surface and defined as: a Capping protein (Actin filament) muscle Z-line beta protein or a variant thereof, wherein said Capping protein (Actin filament) muscle Z-line beta protein or variant thereof is capable of binding specifically to an IgE antibody of a patient with an allergy to fish, and is defined below in any of (a) to (d):

(a) comprising the amino acid sequence of SEQ ID NO: 61, with or without a conserved amino acid substitution of a residue of SEQ ID NO: 61;

(b) having 100% identity to the full-length amino acid sequence of SEQ ID NO: 61;

(c) comprising an amino acid sequence encoded by a nucleotide sequence having 100% identity to the nucleotide sequence of SEQ ID NO: 60; or (d) encoded by a nucleic acid that hybridizes over its full-length under high stringent conditions of 0.1×SSC to 2×SSC hybridization at 55° C. to 65° C. and/or 0.2×SSC to 2×SSC washing at 50° C. to 68° C., with the nucleic acid complementary to the nucleotide sequence of SEQ ID NO: 60.

* * * * *